(12) United States Patent
Mundorff et al.

(10) Patent No.: US 9,228,223 B2
(45) Date of Patent: Jan. 5, 2016

(54) STRUCTURE-ACTIVITY RELATIONSHIPS

(71) Applicant: Codexis, Inc., Redwood City, CA (US)

(72) Inventors: Emily Mundorff, Garden City, NY (US); Simon Christopher Davis, San Francisco, CA (US); Gjalt W. Huisman, Redwood City, CA (US); Anke Krebber, Palo Alto, CA (US); John H. Grate, Los Altos, CA (US); Richard Fox, Kirkwood, MO (US)

(73) Assignee: Codexis, Inc., Redwood City, CA (US)

( * ) Notice: Subject to any disclaimer, the term of this patent is extended or adjusted under 35 U.S.C. 154(b) by 4 days.

(21) Appl. No.: 13/757,554

(22) Filed: Feb. 1, 2013

(65) Prior Publication Data
US 2013/0165341 A1 Jun. 27, 2013

Related U.S. Application Data

(62) Division of application No. 12/069,869, filed on Feb. 12, 2008, now abandoned.

(60) Provisional application No. 60/901,349, filed on Feb. 12, 2007, provisional application No. 60/909,937, filed on Apr. 30, 2007.

(51) Int. Cl.
| | | |
|---|---|---|
| *C40B 30/04* | (2006.01) |
| *C40B 30/08* | (2006.01) |
| *G01N 33/68* | (2006.01) |
| *C12Q 1/00* | (2006.01) |
| *C12Q 1/25* | (2006.01) |
| *C12Q 1/26* | (2006.01) |
| *G06F 19/18* | (2011.01) |
| *C12N 9/00* | (2006.01) |
| *C12N 15/10* | (2006.01) |
| *C40B 10/00* | (2006.01) |
| *C40B 40/02* | (2006.01) |
| *C40B 40/10* | (2006.01) |

(52) U.S. Cl.
CPC .. *C12Q 1/25* (2013.01); *C12N 9/00* (2013.01); *C12N 15/1093* (2013.01); *C12Q 1/00* (2013.01); *C12Q 1/26* (2013.01); *C40B 10/00* (2013.01); *C40B 30/04* (2013.01); *C40B 40/02* (2013.01); *C40B 40/10* (2013.01); *G01N 33/6803* (2013.01); *G06F 19/18* (2013.01)

(58) Field of Classification Search
CPC ........ C40B 30/04; C40B 30/08; C40B 40/10; C12Q 1/00; C12Q 1/26; G06F 19/18; G01N 33/6803
USPC ............... 506/9, 11, 18; 435/4, 7.1
See application file for complete search history.

(56) References Cited

U.S. PATENT DOCUMENTS

| | | |
|---|---|---|
| 5,605,793 A | 2/1997 | Stemmer |
| 6,117,679 A | 9/2000 | Stemmer |
| 6,153,410 A | 11/2000 | Arnold et al. |
| 6,335,160 B1 | 1/2002 | Patten et al. |
| 6,376,246 B1 | 4/2002 | Crameri |
| 6,649,340 B1 | 11/2003 | Crea |
| 6,713,282 B2 | 3/2004 | Short et al. |
| 6,743,581 B1 | 6/2004 | Vo-Dinh |
| 6,773,900 B2 | 8/2004 | Short et al. |
| 6,917,882 B2 | 7/2005 | Selifonov et al. |
| 6,961,664 B2 | 11/2005 | Selifonov et al. |
| 7,024,312 B1 | 4/2006 | Selifonov et al. |
| 7,033,781 B1 | 4/2006 | Short |
| 7,058,515 B1 | 6/2006 | Selifonov et al. |
| 7,462,469 B2 | 12/2008 | Bass et al. |
| 2002/0119492 A1 | 8/2002 | Chirino et al. |
| 2002/0127623 A1 | 9/2002 | Minshull et al. |
| 2002/0177170 A1 | 11/2002 | Luo et al. |
| 2005/0196834 A1 | 9/2005 | Rao et al. |
| 2005/0202438 A1 | 9/2005 | Gantier et al. |
| 2006/0134086 A1 | 6/2006 | Chen et al. |
| 2006/0160138 A1 | 7/2006 | Church et al. |
| 2006/0194254 A1 | 8/2006 | Huse et al. |
| 2006/0223143 A1 | 10/2006 | Patten et al. |
| 2006/0234303 A1 | 10/2006 | Moore et al. |
| 2006/0257978 A1 | 11/2006 | Alexeeva et al. |
| 2006/0263800 A1 | 11/2006 | Shokat |

FOREIGN PATENT DOCUMENTS

| | | |
|---|---|---|
| EP | 1589463 A1 | 10/2005 |
| WO | WO 01/42455 A1 | 6/2001 |
| WO | WO 01/51663 | 7/2001 |
| WO | WO 01/59066 A2 | 8/2001 |
| WO | WO 01/64912 | 9/2001 |
| WO | WO 02/10750 | 2/2002 |
| WO | 02/45012 A2 | 6/2002 |
| WO | WO 03/048768 A2 | 6/2003 |
| WO | WO 03/075129 A2 | 9/2003 |
| WO | WO 2005/013090 A2 | 2/2005 |
| WO | WO 2006/023144 A2 | 3/2006 |
| WO | WO 2006/133013 A2 | 12/2006 |
| WO | 2009/008908 A2 | 1/2009 |
| WO | 2009/102899 A1 | 8/2009 |
| WO | 2009/102901 A1 | 8/2009 |

OTHER PUBLICATIONS

Raillard et al., "Novel enzyme activities and functional plasticity revealed by recombining highly homologous enzymes," Chem. Biol. 2001, 8:891-898.*

Templin et al., "Protein microarray technology," Drug Discov. Today 2002, 7:815-822.*

(Continued)

*Primary Examiner* — Samuel Woolwine
*Assistant Examiner* — Kaijiang Zhang
(74) *Attorney, Agent, or Firm* — Codexis, Inc.

(57) ABSTRACT

The present disclosure relates to compositions and methods for screening a plurality of polypeptide variants.

17 Claims, 16 Drawing Sheets

(56) References Cited

OTHER PUBLICATIONS

Horn, J., et al., "A Niched Pareto Genetic Algorithm for Multiobjective Optimization," Evolutionary Computation, IEEE World Congress on Computational Intelligence, Proceedings of the First IEEE Conference on Orlando, FL, USA, pp. 82-87, Jun. 1994.
Willett, P., "Genetic algorithms in molecular recognition and design," Trends in Biotechnology, 13(12):516-521, 1995.
Ness, et al., "DNA shuffling of subgenomic sequences of subtilisin," Nature Biotechnology, 17:893-896, 1999.
Arenkov, et al., 2000, "Protein Microchips: Use for Immunoassay and Enzymatic Reactions," Anal. Biochem., 278:123-131.
Fox, et al., 2007, "Improving catalytic function by ProSAR-driven enzyme evolution," Nat. Biotechnol., 25(3):338-344.
Houseman, et al., 2002, "Peptide chips for the quantitative evaluation of protein kinase activity," Nat. Biotechnol., 20:270-274.
MacBeath et al., 2000, "Printing Proteins as Microarrays for High-Throughput Function Determination," Science, 289:1760-1763.
Bornscheuer, 2002, "Methods to increase enantioselectivity of lipases and esterases," Curr. Opin. Biotechnol., 13(6):543-547.
Cherry et al., 2003, "Directed evolution of industrial enzymes: an update," Curr. Opin. Biotechnol., 14(4):438-443.
Chockalingam et al., 2005, "Directed evolution of specific receptor-ligand pairs for use in the creation of gene switches," Proc. Nat. Acad. Sci. U.S.A., 102(16)5691-5696.
Gupta et al., 2004, "Bacterial lipases: an oveniew of production, purification and biochemical properties," Appl. Microbiol. Biotechnol., 64(6)763-781.

PCT International Search Report from PCT/US2008/001907, dated Jan. 13, 2009.
Kazlauskas et al., 1998, "Improving hydrolases for organic synthesis," Curr. Opin. Chem. Biol., 2(1):121-126.
Kirk et al., 2002, "Industrial enzyme applications," Curr. Opin. Chem. Biol., 13(4):345-351.
Morley et al., 2005, "Improving enzyme properties: when are closer mutations better?", Trends Biotechnol., 23(5):231-237.
Turner, 2003, "Controlling Chirality," Curr. Opin. Chem. Biol., 14(4):401-406.
Wong et al., 2006, "A Statistical Analysis of Random Mutagenesis Methods Used for Directed Protein Evolution," J. Mol. Biol., 355(4):858-871.
Zhu et al., 2003, "Protein chip technology," Curr. Opin. Chem. Biol., 7(1)55-63).
Aharoni et al., 2005, Nature Genetics 37(1):73-76.
Copley, S.D., 2003, Curr.Opin.Chem. Biol. 7:265-272.
Gustafsson et al., 2003, Curr. Opin. Biotech. 14:366-370.
James, L.C. and Tawfik, D.D., Trends Biochem. Sci. 28(7):361-368, Jul. 2003.
O'Brien, P.J. and Herschlag, D., 1999, Chem.& Biol. 6(4):R91-R105.
Schneider et al., 1998, Proc. Natl. Acad. Sci. USA 95:12179-12184.
Wise, E.L., and Rayment, I, 2004, Acc Chem. Res. 37:149-158.
Yazbeck et al., 2003, Adv. Synth. Catal. 345(4):524-532.

\* cited by examiner

Generate Binding Pocket Diversity

Binding pocket

● Position of influence

- Identify positions with predicted influence on substrate specificity
  - Mutations re

STRUCTURE-ACTIVITY RELATIONSHIPS

1. CROSS REFERENCE TO RELATED APPLICATIONS

This application is a Divisional of co-pending U.S. patent application Ser. No. 12/069,869, filed Feb. 12, 2008, which claims benefit under 35 U.S.C. §119(e) to application U.S. Patent Application Ser. No. 60/901,349, filed Feb. 12, 2007 and U.S. Patent Application Ser. No. 60/909,937, filed Apr. 3, 2007, the disclosures of which are incorporated herein by reference in their entirety.

2. BACKGROUND

Methods for screening and identifying polypeptides having desired activities are useful in the preparation of new compounds such as enzymes, hormones, receptors and pharmaceutical compounds. Current methods for identifying novel polypeptides are often time-consuming and costly, requiring screening an enormous number of polypeptide variants, and it may take months or years to find a new polypeptide with the desired activity, if one is ever found. These limitations also make the known methods less than ideal for timely development of commercial products and processes. Thus, compositions and methods useful in accelerated identification of novel polypeptide variants having desired activities in a cost effective and time efficient manner would be highly desirable.

3. SUMMARY

The present disclosure provides compositions and methods involving a plurality of polypeptides having certain activities, which plurality aids in the identification of new polypeptides with desired or enhanced activities.

In some aspects of the disclosure, each polypeptide in the plurality reacts with at least one substrate to produce a product, and at least two members of the plurality are related to a parent polypeptide and react with differing levels of activity upon a given substrate. In some aspects of the disclosure, each polypeptide in the plurality reacts with at least one substrate to produce a product, and at least two members of the plurality are related to a parent polypeptide and react with different substrates. Also contemplated are compositions comprising pluralities of pluralities, in which each plurality acts on a different class of substrate, as well as methods of generating and screening these pluralities of pluralities.

In some aspects, a plurality of enzymes is made by generating variants of at least one parent enzyme wherein at least a portion of each variant is known and wherein each variant comprises at least one mutation known to affect reactivity with a substrate to produce a product, and selecting two or more variants wherein at least two of the selected variants react with differing levels of activity upon a given substrate. In some aspects, a plurality of enzymes is made by generating variants of at least one parent enzyme wherein at least a portion of each variant is known and wherein each variant comprises at least one mutation known to affect reactivity with a substrate to produce a product, and selecting two or more variants wherein at least two of the selected variants react with different substrates.

In some aspects, the methods involve screening a plurality of polypeptide variants against a ligand of interest, wherein each variant reacts with at least one ligand to produce a detectable signal, and wherein at least two members of the plurality are related to a parent polypeptide and react with differing levels of activity upon a given ligand, and identifying at least one variant that produces a signal upon reaction with the ligand of interest. In some aspects, the methods involve screening a plurality of polypeptide variants against a ligand of interest, wherein each variant reacts with at least one ligand to produce a detectable signal, and wherein at least two members of the plurality are related to a parent polypeptide and react with different ligands, and identifying at least one variant that produces a signal upon reaction with the ligand of interest.

In some aspects, the methods involve making a plurality of polypeptide variants by generating a plurality of polypeptide variants related to a parent polypeptide, a portion of each variant having known amino acid sequence, wherein each variant comprises at least one mutation that enhances reactivity with a substrate as compared to the reactivity of the parent polypeptide with said substrate, and wherein at least two members of the plurality react with differing levels of activity upon a given substrate; and assigning an address to each of the variants. In some aspects, the methods involve making a plurality of polypeptide variants by generating a plurality of polypeptide variants related to a parent polypeptide, a portion of each variant having known amino acid sequence, wherein each variant comprises at least one mutation that enhances reactivity with a substrate as compared to the reactivity of the parent polypeptide with said substrate, and wherein at least two members of the plurality react with different substrates; and assigning an address to each of the variants.

In some aspects, the methods involve making a plurality of pluralities by generating a first and a second addressable plurality of polypeptide variants, wherein the members of the first plurality are related to one parent polypeptide and the members of the second plurality are related to a second parent polypeptide, wherein at least a portion of the amino acid sequence of each variant is known, wherein each member of each plurality reacts with a substrate to produce a product, and wherein at least two members of the first plurality react with differing levels of activity upon a given substrate and at least one member of the first plurality and at least one member of the second plurality react with different substrates. In some aspects, the methods involve making a plurality of pluralities by generating a first and a second addressable plurality of polypeptide variants, wherein the members of the first plurality are related to one parent polypeptide and the members of the second plurality are related to a second parent polypeptide, wherein at least a portion of the amino acid sequence of each variant is known, wherein each member of each plurality reacts with a substrate to produce a product, and wherein at least one member of the first plurality and at least one member of the second plurality react with different substrates. Also contemplated are pluralities of host cell colonies and kits for identifying at least one polypeptide having a desired activity using the compositions and methods disclosed herein.

Virtually any enzyme/substrate or receptor/ligand combination can be used as the basis for making evolvants used in the compositions and methods disclosed. It is also contemplated that a substrate or ligand of unknown identity can be used to screen polypeptide evolvants of an ancestral or parent enzyme or receptor for a desired activity. In some embodiments, the plurality of polypeptides is a plurality of enzyme candidates. In some embodiments, the substrate screened is an unknown substrate. Also contemplated is a plurality, including members that act on different and diverse substrates, for carrying out different chemical conversions. In some embodiments, each member of a plurality acts on a different substrate. In some embodiments, some members of a plurality act on one substrate, and other members act on at least one other substrate. In some embodiments, at least two of the members of the plurality differ with respect to one or more of the following properties: substrate specificity, chemoselectivity, regioselectivity, stereoselectivity, stereospecificity, ligand specificity, receptor agonism, receptor antagonism, conversion of a cofactor. In some embodiments, members of the plurality that act on the same substrate differ with respect to one or more of the following properties: rate of product formation, percent conversion of a substrate to a product, or percent conversion of a cofactor. In some embodiments, the polypeptides of the plurality, each of which reacts with a substrate to produce a product, is operable under a wide range of conditions, such as high or low pH, high or low temperature, or the presence of organic solvents. In some embodiments, all members of the plurality are evolved variants (evolvants) of the same parent enzyme, each evolvant containing at least one mutation as compared to the parent enzyme. In some embodiments, the plurality comprises subsets of variants, and each subset comprises evolvants from a separate parent enzyme. These and other features of the present teachings are set forth herein.

4. BRIEF DESCRIPTION OF THE FIGURES

The skilled artisan will understand that the figures, described below, are not intended to limit the scope of the present disclosure, but are for illustration purposes only.

FIG. 2 illustrates a scheme for generating a plurality of polypeptide evolvants of an ancestral or parent enzyme;

Figure 7:
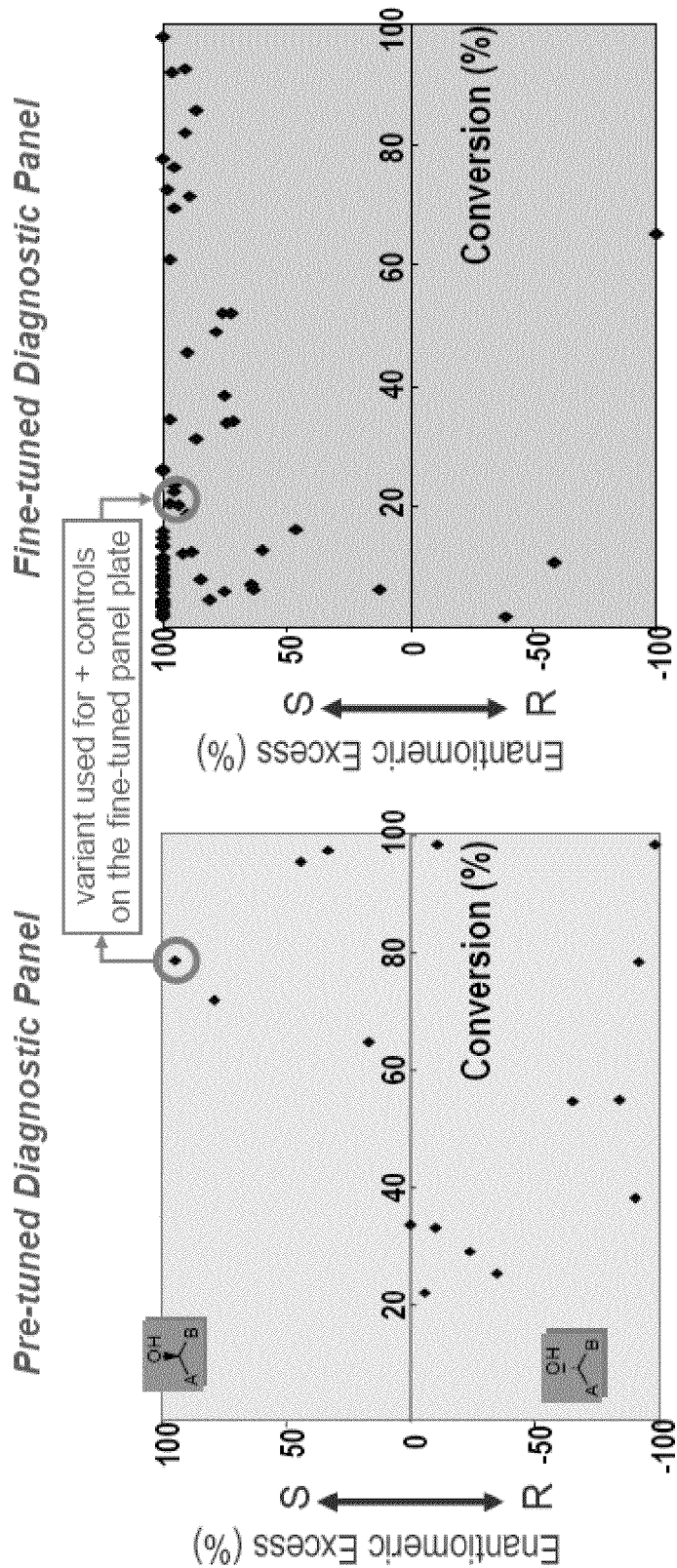
Figure 8:
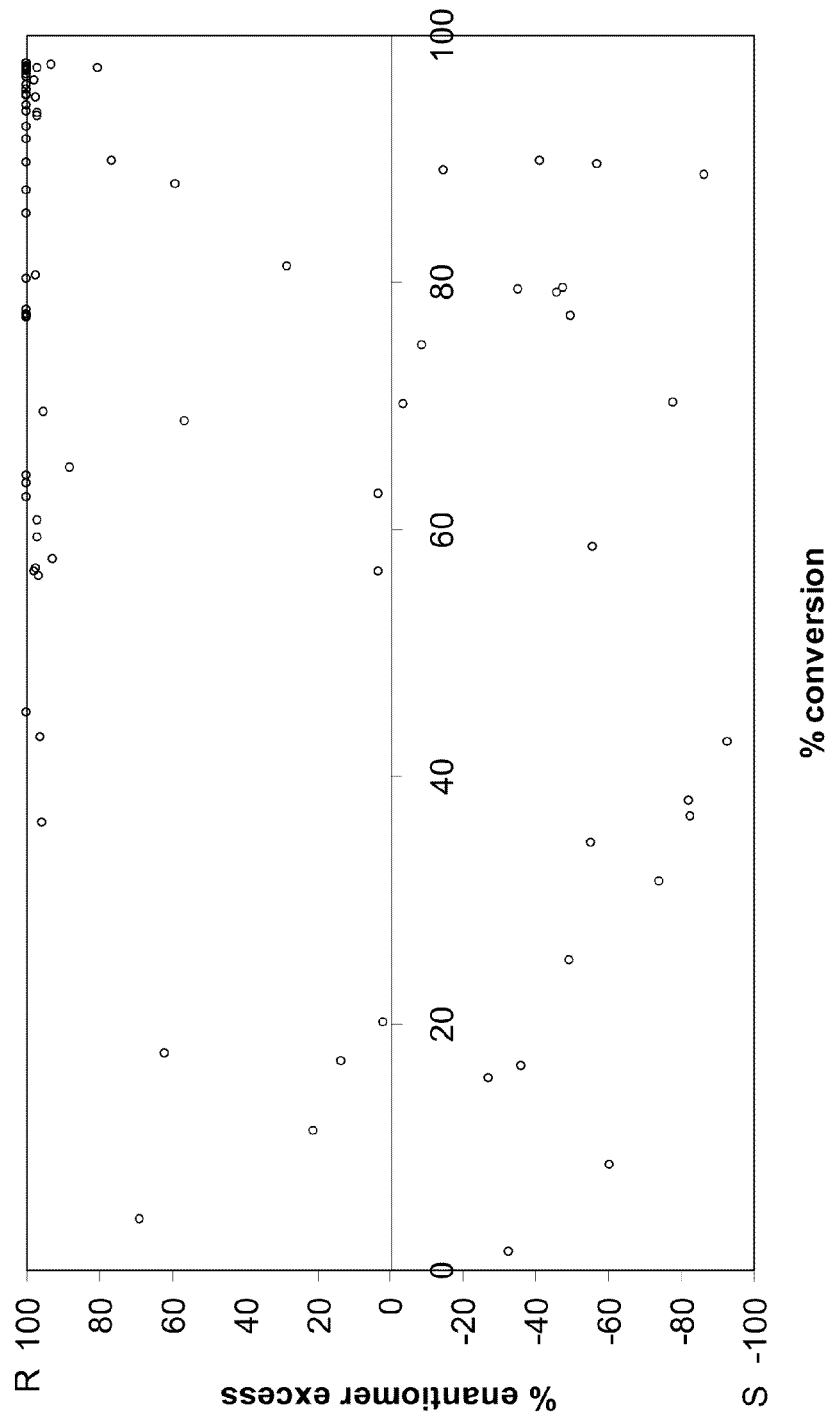
Figure 9:
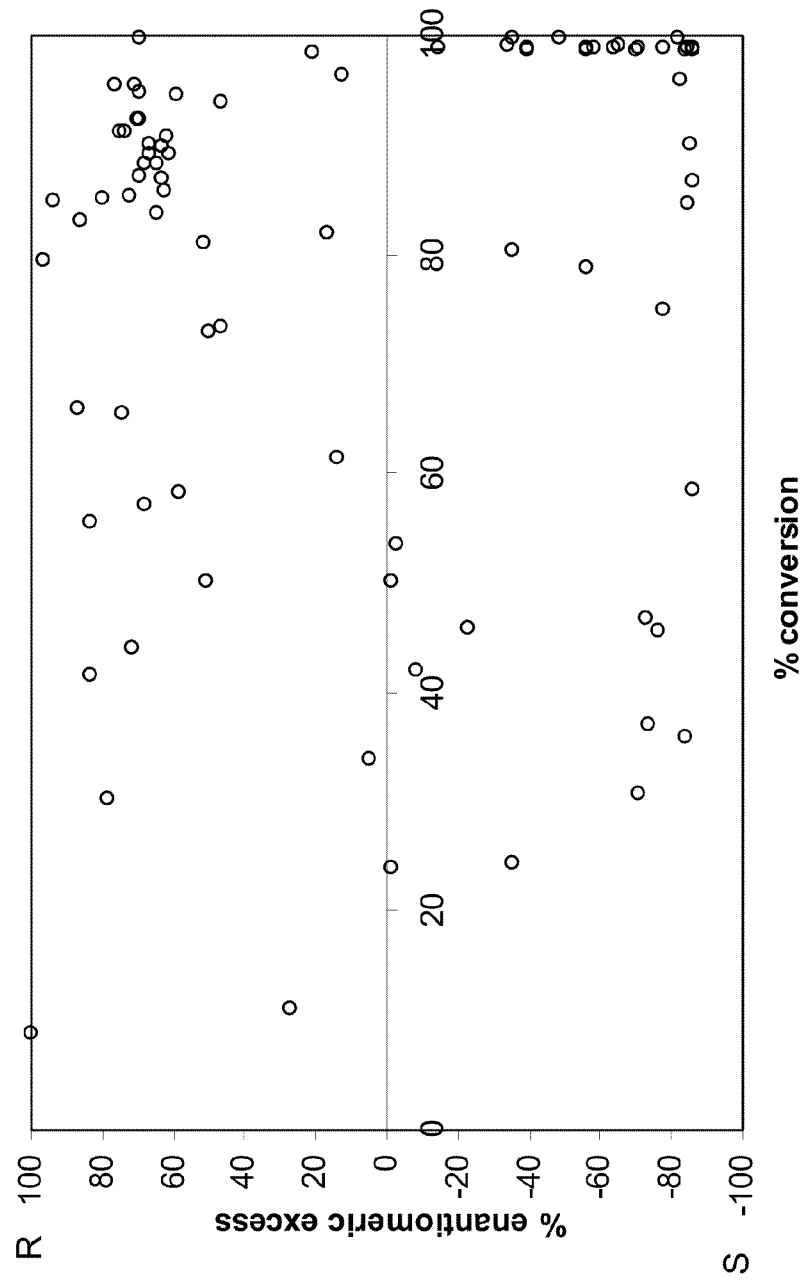
Figure 10:
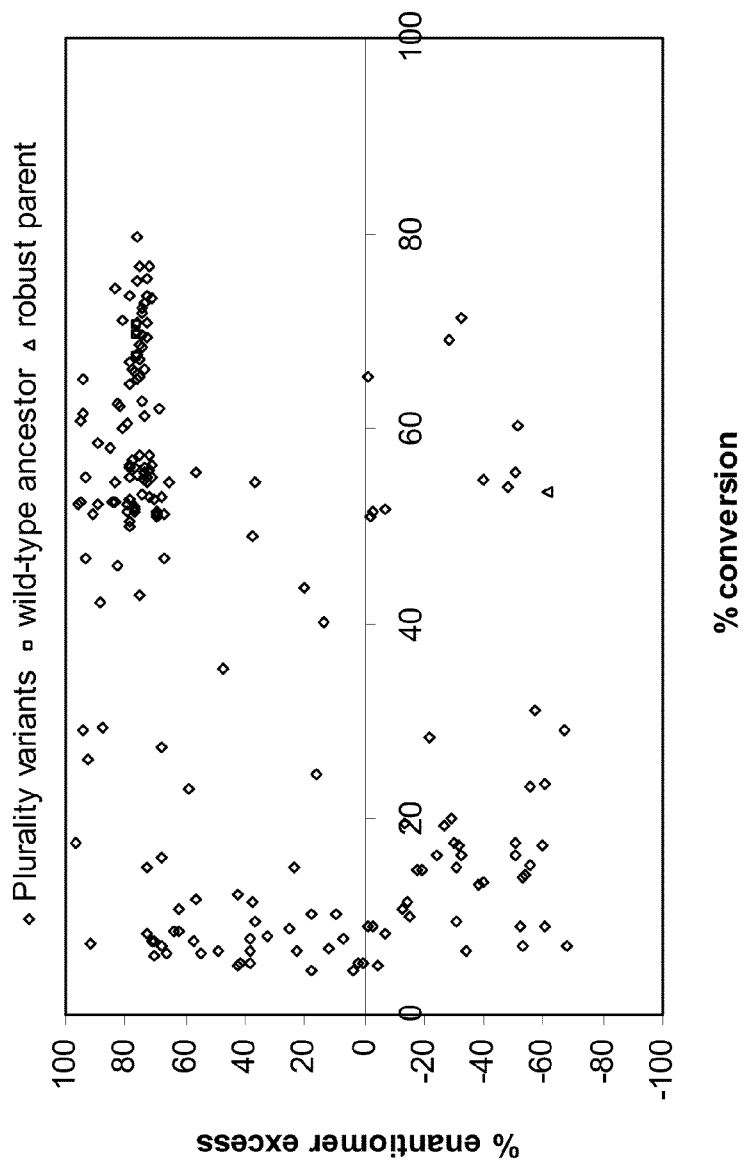
Figure 11:
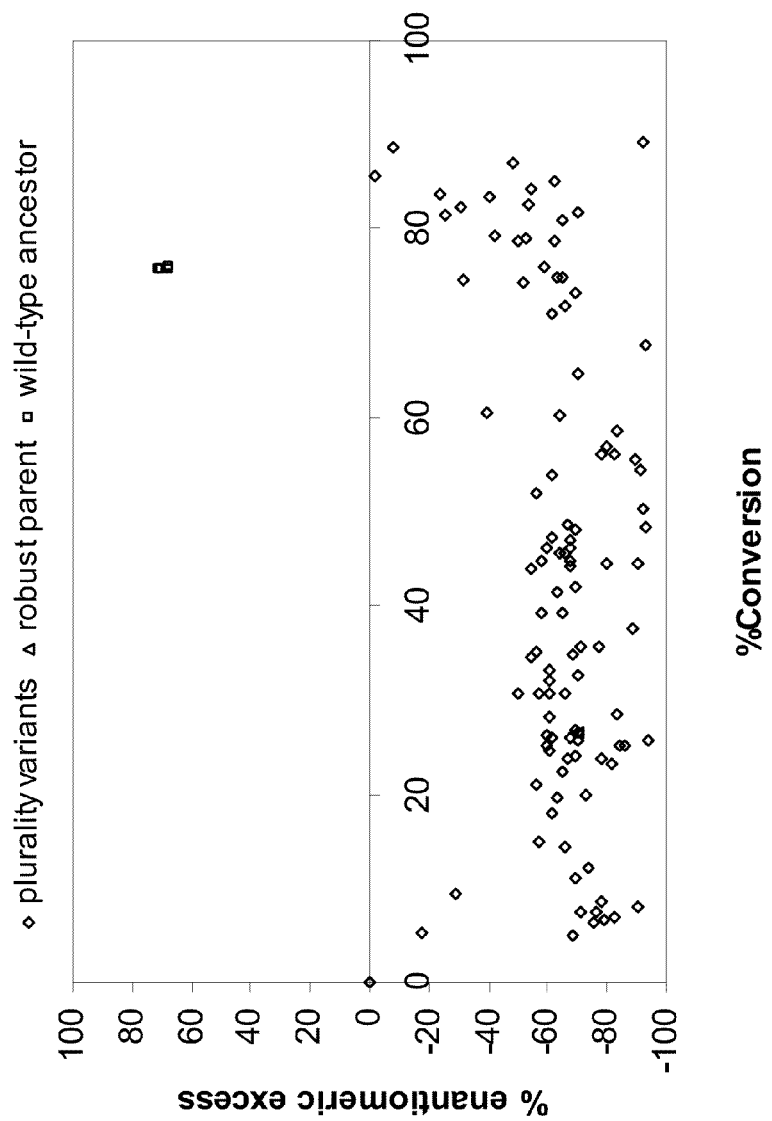
Figure 12:
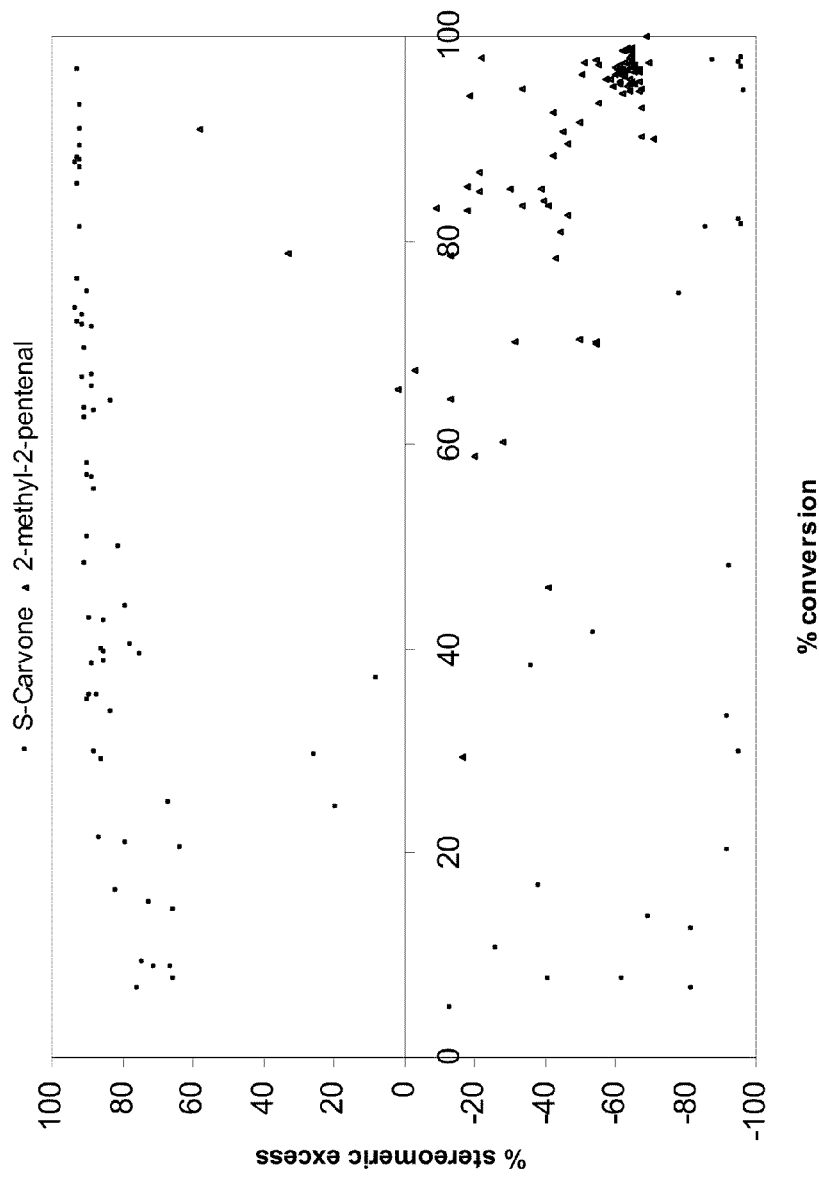
Figure 13:
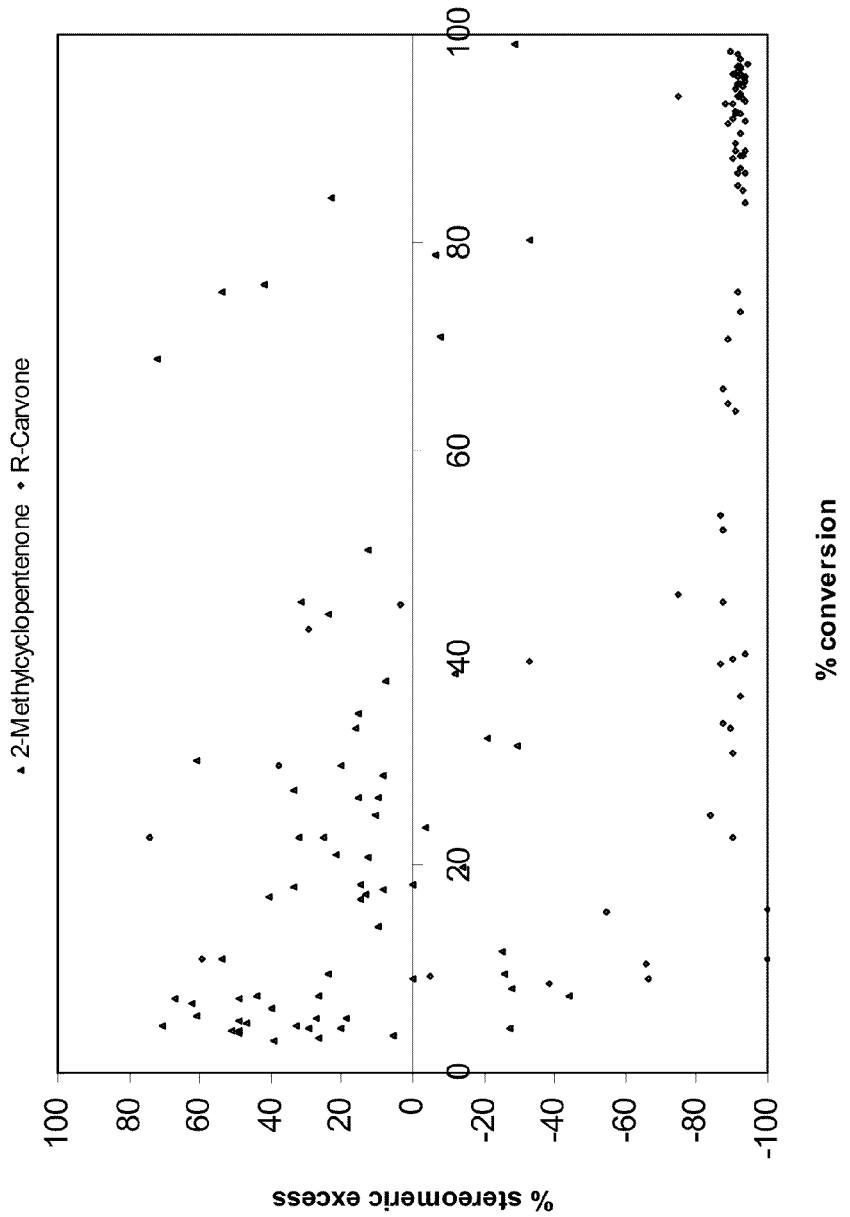

FIG. 7 illustrates an exemplary range of activities and enantioselectivities exhibited by a first plurality of polypeptide evolvants on a the new substrate, (S)-1-(4-Fluoro-phenyl)-5-(2-oxo-4-phenyl-oxazolidin-3-yl)-pentane-1,5-dione, not used in the generation and compilation of the plurality, and enhanced properties exhibited by a second plurality of polypeptide evolvants designed and generated based on the activities and enantioselectivities exhibited by the first plurality. See Example 6; and FIG. 8 illustrates a plot of the % conversion of acetophenone and the % enantiomeric excess (e.e.) of the resulting 1-phenethanol exhibited by a plurality of ketoreductase evolvants. See Example 4; and FIG. 9 illustrates a plot of the % conversion of 3-ketothiolane and the % enantiomeric excess (e.e.) of the resulting 3-hyroxythiolane exhibited by a plurality of ketoreductase evolvants. See Example 5; and FIG. 10 illustrates an exemplary range of activities and enantioselectivities exhibited by a pre-tuned plurality of ketoreductase polypeptide evolvants on a new substrate, 3-butyn-2-one, not tested during the generation and compilation of the plurality. See Example 7; and FIG. 11 illustrates an exemplary range of activities and enantioselectivities exhibited by a fine-tuned plurality of polypeptide evolvants on 3-butyn-2-one, generated based on the activities and enantioselectivities exhibited by the pre-tuned plurality. See Example 7; and FIG. 12 illustrates a plot of the % conversions of S-carvone and 2-methyl-2-pentenal and the % stereromeric excesses of the resulting (5S)-dihydrocarvone and 2-methyl pentanal, respectively, exhibited by a plurality of enone reductase evolvants. See Examples 9 and 10, respectively; and FIG. 13 illustrates a plot of the % conversions of R-carvone and 2-methyl-cyclopentenone and the % stereromeric excesses of the resulting (5R)-dihydrocarvone and 2-methyl-cyclopentanone, respectively, exhibited by a plurality of enone reductase evolvants. See Examples 11 and 12, respectively.

Figure 14:
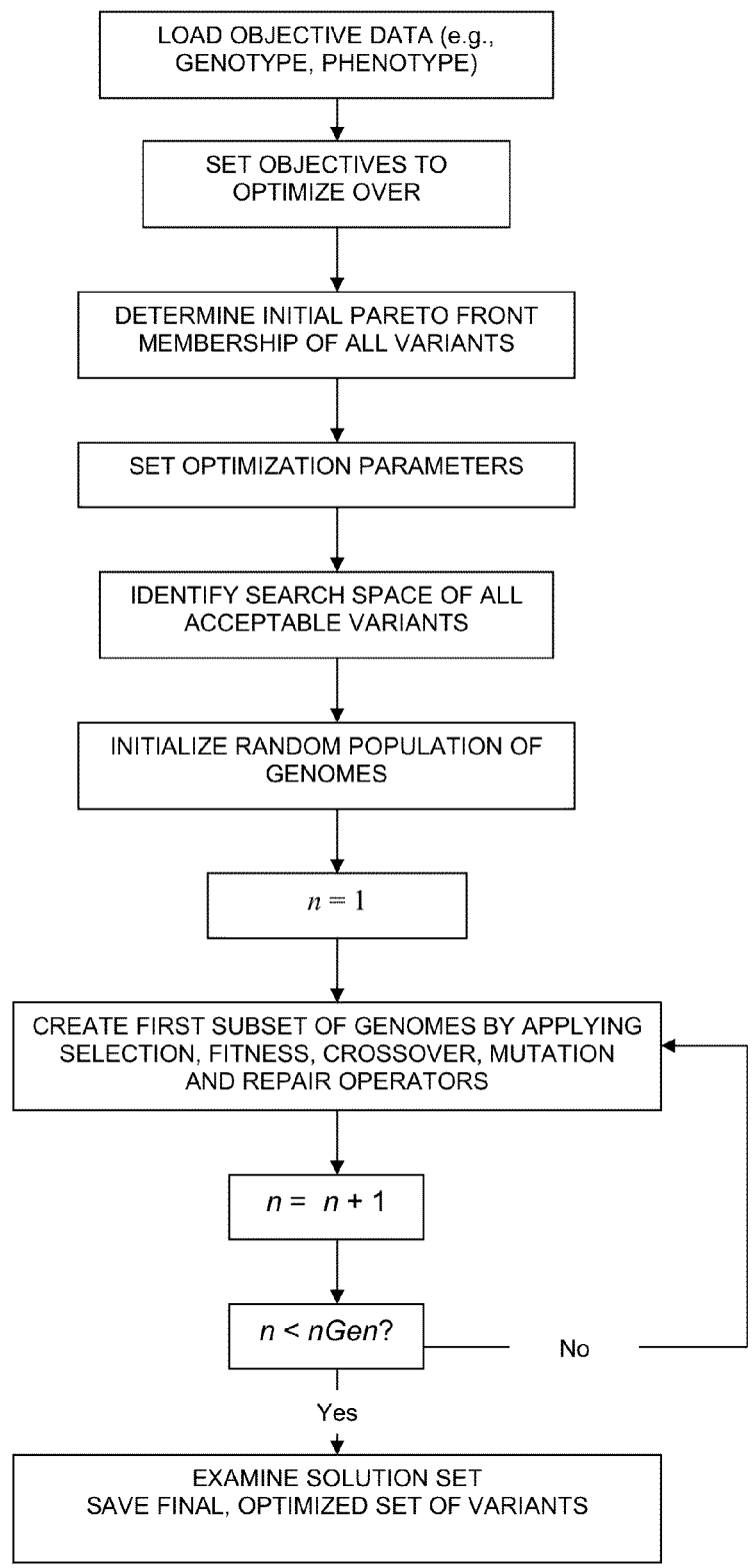

FIG. 14 shows a flow diagram for selecting an optimized, diverse set of polypeptide variants to initial screening for novel properties.

Figure 15:
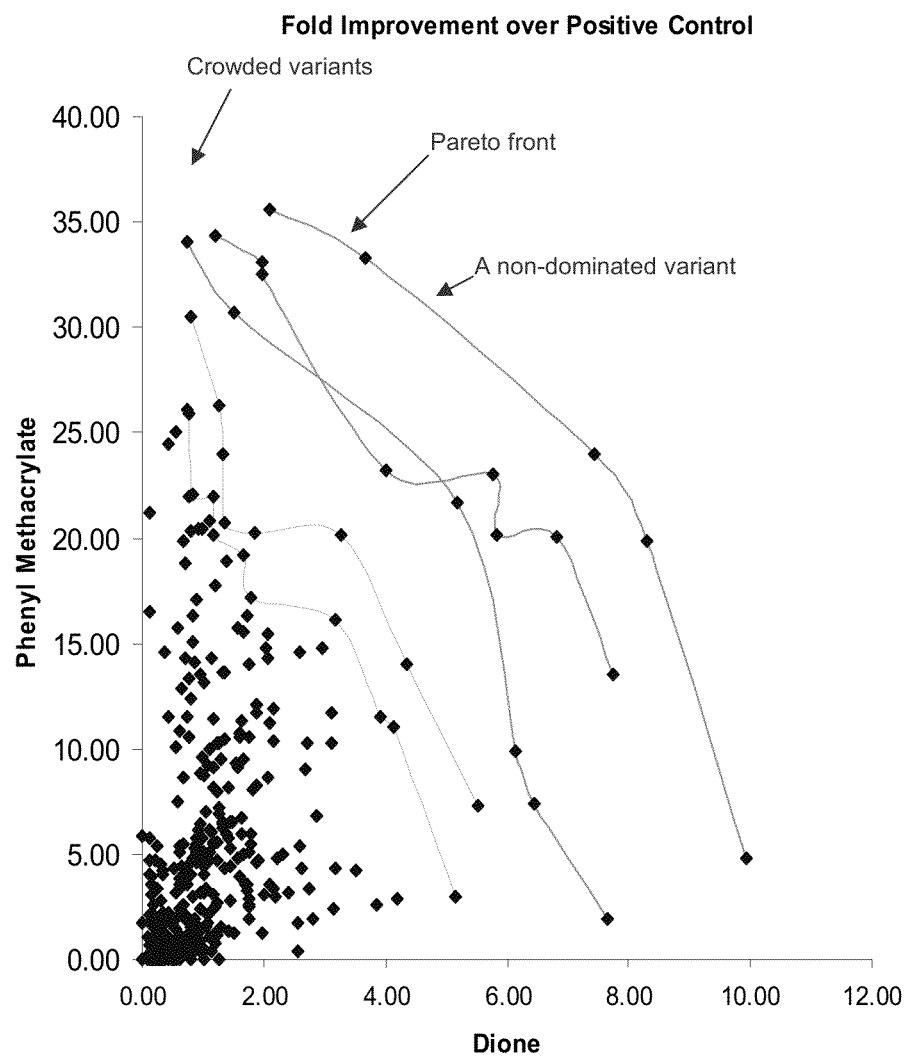

FIG. 15 shows a plot of the non-domination and the Pareto optimal front based on the fold improvement versus a positive control for enone-reductase enzyme (ERED) for two different substrates.

Figure 16:
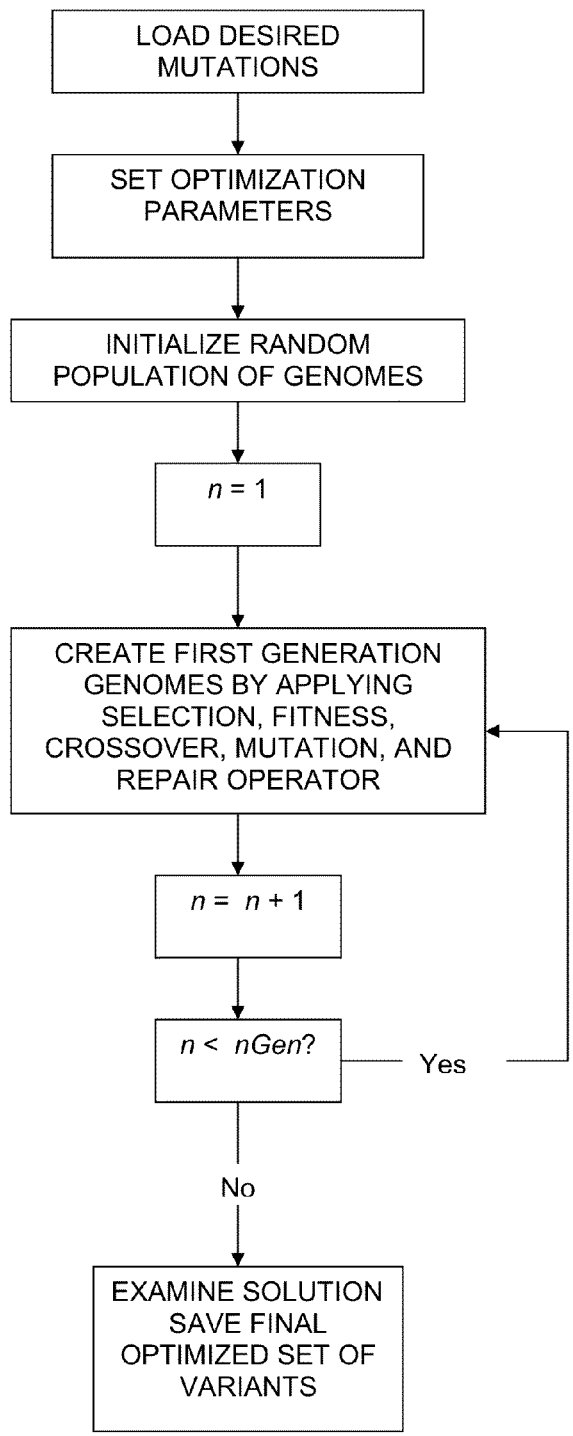

FIG. 16 shows a flow diagram of the method for creating a set of optimized diverse population of polypeptide variants based on a set of mutations identified from an initial screen.

5. DETAILED DESCRIPTION

5.1 General

It is to be understood that both the foregoing general description, including the figures, and the following detailed description are exemplary and explanatory only and are not restrictive of this disclosure. It is to be further understood that the section headings used herein are for organizational purposes only and not to be construed as limiting the subject matter described.

As used in this specification and the appended claims, the singular forms "a," "an" and "the" include plural referents unless the context clearly indicates otherwise. Thus, for example, reference to "a polypeptide" includes more than one polypeptide, and reference to "a plurality" refers to more than one plurality. In this disclosure, the use of "or" means "and/or" unless stated otherwise.

Similarly, "comprise," "comprises," "comprising," "include," "includes," and "including" are interchangeable and not intended to be limiting. It is to be further understood that where descriptions of various embodiments use the term "comprising," those skilled in the art would understand that in some specific instances, an embodiment can be alternatively described using language "consisting essentially of" or "consisting of."

In the present disclosure, the following terminology will be used in accordance with the definitions set out below.

5.2 Definitions

As used herein, the following terms are intended to have the following meanings:

"Protein," "polypeptide" and "peptide" are used interchangeably to denote a polymer of at least two amino acids covalently linked by an amide bond, regardless of length or post-translational modification (e.g., glycosylation, phosphorylation, lipidation, myristilation, ubiquitination, etc). Included within this definition are D- and L-amino acids, and mixtures of D- and L-amino acids.

"Native sequence" or "wild type" as used herein refers to a polynucleotide or polypeptide isolated from a naturally occurring source. Included within "native sequence" are recombinant forms of a native polypeptide or polynucleotide which have a sequence identical to the native form.

"Recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide.

"Recombinant host cell" refers to a cell that comprises a recombinant nucleic acid molecule. Thus, for example, recombinant host cells can express genes that are not found within the native (non-recombinant) form of the cell.

"Mutant," "evolvant" or "variant" as used herein refer to an amino acid or polynucleotide sequence which has been altered by substitution, insertion, and/or deletion. For purposes of the present disclosure, a mutant, evolvant or variant is not limited to a particular method by which it is generated. In some embodiments, a mutant, evolvant or variant sequence can have increased, decreased, or substantially similar activities or properties in comparison to the parental sequence. In some embodiments, the polypeptide may contain one or more amino acid residues that have been mutated as compared to the amino acid sequence of the wild type polypeptide. In some embodiments, one or more amino acid residues of the polypeptide are held constant, are invariant, or are not mutated as compared to a parent polypeptide in the variant polypeptides comprising the plurality. In some embodiments, the parent polypeptide is robust to challenge with high and/or low temperature or high and/or low pH conditions, or with organic solvent. In some embodiments, the parent polypeptide is used as the basis for generating variants with improved robustness to challenge with at high and/or low temperature or high and/or low pH conditions, or with organic solvent. Variants having improved robustness may be used to populate a plurality, or they may be used as the basis for generating further variants with desirable activities or properties.

"Percentage of sequence identity" refers to comparisons among polynucleotides and comparisons among polypeptides, determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)). Examples of algorithms that are suitable for determining percent sequence identity and sequence similarity are the BLAST and BLAST 2.0 algorithms, which are described in Altschul et al. (1990) J. Mol. Biol. 215: 403-410 and Altschul et al. (1977) Nucleic Acids Res. 3389-3402, respectively. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89:10915 (1989)).

While all of the above mentioned algorithms and programs are suitable for a determination of sequence alignment and % sequence identity, for purposes of the disclosure herein, determination of % sequence identity will typically be performed using the BESTFIT or GAP programs in the GCG Wisconsin Software package (Accelrys, Madison Wis.), using default parameters provided.

"Substantial identity" refers to a polynucleotide or polypeptide sequence that has at least 80 percent sequence identity, at least 85 percent identity and 89 to 95 percent sequence identity, more usually at least 99 percent sequence identity as compared to a reference sequence over a comparison window of at least 20 residue positions, frequently over a window of at least 30-50 residues, wherein the percentage of sequence identity is calculated by comparing the reference sequence to a sequence that includes deletions or additions which total 20 percent or less of the reference sequence over the window of comparison. In specific embodiments applied to polypeptides, the term "substantial identity" means that two polypeptide sequences, when optimally aligned, such as by the programs GAP or BESTFIT using default gap weights, share at least 80 percent sequence identity, at least 89 percent sequence identity, at least 95 percent sequence identity or more (e.g., 99 percent sequence identity). In some embodiments, residue positions which do not have identical amino acids differ by conservative amino acid substitutions.

"Substrate specificity" refers to the kind, class or identity of substrate upon which the enzyme or catalytic molecule reacts. Similarly, "ligand specificity" refers to the kind, class or identify of ligand to which a receptor binds. A ligand specifically binding to a receptor may act as an agonist or antagonist of the receptor.

As is known in the art, "receptor agonism" refers to the binding and activation of a cell receptor by a ligand, whereas "receptor antagonism" refers to the binding of a ligand to a cell receptor not resulting in activation of the receptor.

"Stereoselectivity" refers to the preferential formation in a chemical or enzymatic reaction of one stereoisomer over another. Stereoselectivity can be partial, where the formation of one stereoisomer is favored over the other, or it may be complete where only one stereoisomer is formed. When the stereoisomers are enantiomers, the stereoselectivity is referred to as enantioselectivity, the fraction (typically reported as a percentage) of one enantiomer in the sum of both. It is commonly reported in the art (typically as a percentage) as the enantiomeric excess (e.e.) calculated therefrom according to the formula [major enantiomer−minor enantiomer]/[major enantiomer+minor enantiomer]. Where the stereoisomers are diastereoisomers, the stereoselectivity is referred to as diastereoselectivity, the fraction (typically reported as a percentage) of one diastereomer in the sum with others. It may also be reported (typically as a percentage) as the diastereomeric excess (d.e.).

Stereospecificity refers to the preferential reaction, in a chemical or enzymatic reaction of one stereoisomer in a mixture of stereoisomers over another. Stereospecificity can be partial, where the reaction of one stereoisomer is favored over the other, or it may be complete where only one stereoisomer reacts. When the stereoisomers are enantiomers, as in a racemic mixture (a 1:1 mixture of enantiomers), stereospecificity is referred to as enantiospecificity. Enantiospecificity is commonly reported in the art as the enantiomeric ratio, E, which is the ratio of the rates of reaction (or rate constants) of the two enantiomers, with the rate of the greater reacting enantiomer in the numerator.

"Chemoselectivity" means the preferential reaction of a chemical reagent with one of two or more different functional groups. A reagent has a high chemoselectivity if reaction occurs with only a limited number of different functional groups. Chemoselectivity can also refer to reacting molecules or intermediates which exhibit selectivity toward chemically different reagents.

"Regioselectivity" means the preferential reaction of one of two or more similar or identical functional groups within a molecule.

"Position corresponding to" refers to a position of interest (i.e., nucleobase number or amino acid residue number) in a nucleic acid molecule or protein relative to the position in another reference nucleic acid molecule or protein. Corresponding positions can be determined by comparing and aligning sequences to maximize the number of matching nucleotides or residues, for example, such that identity between the sequences is greater than 95%, greater than 96%, greater than 97%, greater than 98% or greater than 99%. The position of interest is then given the number assigned in the reference nucleic acid molecule. For example, if a particular polymorphism in Gene-X occurs at nucleotide 2073 of a specified sequence, to identify the corresponding nucleotide in another allele or isolate, the sequences are aligned and then the position that lines up with 2073 is identified. Since various alleles may be of different length, the position designate 2073 may not be nucleotide 2073, but instead is at a position that "corresponds" to the position in the reference sequence.

"Fused," "joined" as used herein refers to linkage of heterologous amino acid or polynucleotide sequences. Thus, "fused" refers to any method known in the art for functionally connecting polypeptide and/or polynucleotide domains, including but not limited to recombinant fusion with or without intervening linking sequence, non-covalent association, and covalent bonding.

"Plurality of polypeptides" means a collection of polypeptides. A plurality can be a library of recombinant plasmid or phage vectors, a phage display library, a cell surface display library, an ordered array, a microarray, a panel, a pool or collection of host cell organisms, or any other library, array or collection known to skilled artisans. If the plurality is not an ordered collection of variants, overlapping subsets or matrices comprising members from the plurality can be screened for polypeptides having the desired activity and the data obtained from screening the subsets or matrices can be deconvoluted to identify single polypeptide variants, as is known to the skilled artisan. A plurality typically includes a majority of non-redundant, unique polypeptide variants related to a parent polypeptide, and may include one or more "control" polypeptides of known identity and chemical reactivity.

"Addressable" means that identifying characteristics and the physical location of each member of a plurality is known or is easily locatable. For example, in order to identify specific interactions between a candidate substrate or ligand and a constituent of the plurality, a plurality can be constructed such that the identity and location of every single constituent is known or controlled at the time the plurality is assembled or synthesized. Alternatively, in order to identify specific interactions between a candidate substrate or ligand and a constituent of the plurality, a plurality can be constructed such that every single constituent bears a tag or marker at the time the plurality is assembled or synthesized, such that any constituent later identified in a screen to have desired properties can be easily located or identified. Such pluralities are known as addressable pluralities.

Examples of "surfaces" onto which a plurality of variants can be placed include, but are not limited to, one or more microtiter plates, for example 96- or 384-well microtiter plates, one or more microchips, microparticles or beads. Such surfaces can be comprised of glass, plastic, silica or metal, or other material standard in the art.

"Enzyme candidate" refers to a polypeptide member of a plurality which is screened for activity with a substrate of interest and may or may not exhibit the desired activity for which it is being screened.

"Binding pocket," "binding site" or "active site" refer to the region of the polypeptide where recognition and binding of a substrate or ligand occurs. A binding pocket can be found at the surface of an enzyme or receptor, or it may be embedded in the protein structure. Structural and chemical properties (charge, hydrophobicity, steric hindrance) of the amino acid residues comprising the binding pocket influence substrate or ligand specificity and catalysis. Catalytic residues within the binding pocket may act as proton donors or acceptors. Alternatively, a binding pocket may be a region of the polypeptide that binds a coenzyme or cofactor such as Pyridoxal, Thiamine or NAD. In some embodiments, a substrate or ligand binds in one binding pocket, and a cofactor or coenzyme binds in another binding pocket. In some embodiments, a substrate or ligand binds in the same binding pocket as a cofactor or coenzyme binds.

"Ketoreductase" and "KRED" are used interchangeably herein to refer to a polypeptide that is capable of reducing a carbonyl group in a substrate to yield a hydroxyl group in a product. Some KREDs utilize a cofactor reduced nicotinamide adenine dinucleotide (NADH) or reduced nicotinamide adenine dinucleotide phosphate (NADPH) as the reducing agent. Ketoreductases as used herein include naturally occurring (wild type) ketoreductases as well as non-naturally occurring engineered polypeptides generated by human manipulation. Ketoreductases are alternatively known as alcohol dehydrogenases, or ADHs, in reference to the reverse reaction, oxidation of an alcohol group to a carbonyl group.

"Desired activity" means a measurable property exhibited by the polypeptide(s) for which a plurality may be screened. Examples of desired activities can include, but are not limited to, thermostability, pH stability, substrate specificity, chemoselectivity, stereoselectivity, stereoselectivity, enantioselectivity, stereospecificity, enantiospecificity, regioselectivity, ligand specificity, receptor agonism, receptor antagonism, conversion of a cofactor, and product selectivity, or any combination thereof. A plurality may also be screened to identify a polypeptide having improved, enhanced, diversified or expanded activity, such as an increased rate of product formation, an increase in percent conversion of a substrate to a product, acquisition of a new catalytic ability (such as an ability to react with a substrate with which a plurality's parent polypeptide does not react) or an increased affinity of a receptor for a ligand.

"Thermostable" as used herein refers to a polypeptide which is resistant to inactivation when subjected to the elevated temperatures for the time necessary to effect inactivation of a comparator polypeptide. Thermostable enzymes may be stable at high temperatures and/or may have improved robustness (longevity) at lower temperatures.

"Sequence of the polypeptide is known," "variant of known sequence," "preselected polypeptide" or "predetermined variant" mean that at least a portion of the amino acid sequence of the polypeptide is known at the time it is chosen as a member of the plurality. In some embodiments, the entirety of the amino acid sequence of the polypeptide is known. In some embodiments, the polypeptide has been characterized and found to have a particular activity. In some embodiments, a polypeptide is preselected to become a member of a plurality based on its sequence and/or its activity. In some embodiments, a polypeptide is a portion of the full length ancestral or parental polypeptide, comprising amino acid additions or deletions (i.e., gaps) as compared to the amino acid sequence of the full length ancestral or parental polypeptide, while still retaining functional activity (e.g., catalytic activity).

"Ancestral polypeptide" or "ancestor" is generally used to refer to the wild type polypeptide. "Parent polypeptide" or "parent enzyme" can refer to a wild type or a mutated/evolved polypeptide. In some embodiments, at least two members of the plurality are related to a parent polypeptide. In some embodiments, the ancestor or parent polypeptide is robust to extremes of temperature, pH and/or solvent conditions. In some embodiments, the ancestral polypeptide is not robust to extremes of temperature, pH and/or solvent conditions, and the ancestral polypeptide is evolved to make a robust parent polypeptide from which variants are generated and the plurality is populated. In some embodiments, the parent polypeptide is not robust to extremes of temperature, pH and/or solvent conditions, and the parent polypeptide is mutated to become an evolved parent polypeptide with improved robustness to extremes of temperature, pH and/or solvent conditions, and the evolved parent polypeptide is used as the basis for generating variants to populate the plurality. In some embodiments, the ancestral polypeptide is sufficiently robust to extremes of temperature, pH and/or solvent conditions that the ancestral polypeptide can serve as a parent polypeptide forming the basis for generating variants to populate the plurality.

"Backbone of the polypeptide," "polypeptide backbone," "peptide backbone," or "backbone" refers to the peptide linkages (amide bonds) along with the intervening amino acid alpha-carbon atoms of the polypeptide. The amino acid side chains are attached to the backbone at the alpha carbon atoms.

"Ligand of interest," "candidate substrate," "unknown substrate," "naïve substrate," or "new substrate" means that the chemical identity or sequence of the substrate or ligand used to screen the plurality is not known, or has not been previously shown to react with any member of the plurality being screened. In some embodiments, the sequence, chemical identity and/or chemical properties or characteristics of the substrate or ligand may be known. In some embodiments, members of a general class of substrates (for example, substrates comprising the same functional group transformed by an enzyme for a known substrate) or ligands maybe known to react with at least one polypeptide member of the plurality, but the ligand of interest or candidate substrate itself used to screen the plurality has not been previously demonstrated to react with any member of the plurality being screened.

"Detectable signal" means any measurable property or signal when a substrate or ligand reacts with an enzyme or receptor. Examples of kinds of signals produced can include, but are not limited to, detectable changes in: receptor aggregation, receptor phosphorylation, phosphorylation or dephosphorylation of an intracellular downstream effector, ligand-receptor complexation, conversion of substrate to product, substrate specificity, chemoselectivity, stereoselectivity, stereospecificity, regioselectivity, ligand specificity, receptor agonism, receptor antagonism, conversion of a cofactor, and product selectivity, or any combination thereof.

"Operable" or "functional" means that the polypeptide exhibits an activity. For example, a "robust" operable or functional enzyme retains its activity in harsh conditions, such as at non-physiological pH or temperature, and/or over a wide range of pH, temperature, or solvent conditions, or has pronounced longevity at more neutral conditions and ambient temperatures. In some embodiments, an enzyme may be considered to be robust if it can convert at least 20, 30, 40, 50% or more of its corresponding substrate to a product. A receptor is generally considered operable or functional if it can bind an agonist or antagonist.

"Pre-tuned" means that polypeptide variants used to populate a plurality have been prescreened and found to have desired activity characteristics and these variants containing specific amino acid residues or combinations of amino acid residues are selected to populate a plurality based on sequence-activity relationship information. "Fine-tuned" means that polypeptide variants used to populate a plurality have been selected based upon a screening of a pre-tuned plurality with a ligand of interest or candidate substrate, and the screening results from the pre-tuned variants have been used as a basis for design of new, more refined or "higher resolution" polypeptide variants for populating a fine-tuned plurality. A fine-tuned plurality of variants typically includes variants incorporating specific amino acid residues or combinations of amino acid residues that were identified based on sequence-activity relationships from the screen of the pre-tuned plurality. In some embodiments, a plurality is screened multiple times, each time with a different substrate.

5.2.1 Amino Acid Designations

"Hydrophilic Amino Acid or Residue" refers to an amino acid or residue having a side chain exhibiting a hydrophobicity of less than zero according to the normalized consensus hydrophobicity scale of Eisenberg et al., 1984, *J. Mol. Biol.* 179:125-142. Genetically encoded hydrophilic amino acids include L-Thr (T), L-Ser (S), L-His (H), L-Glu (E), L-Asn (N), L-Gln (O), L-Asp (D), L-Lys (K) and L-Arg (R).

"Acidic Amino Acid or Residue" refers to a hydrophilic amino acid or residue having a side chain exhibiting a pK value of less than about 6 when the amino acid is included in a peptide or polypeptide. Acidic amino acids typically have negatively charged side chains at physiological pH due to loss of a hydrogen ion. Genetically encoded acidic amino acids include L-Glu (E) and L-Asp (D).

"Basic Amino Acid or Residue" refers to a hydrophilic amino acid or residue having a side chain exhibiting a pK value of greater than about 6 when the amino acid is included in a peptide or polypeptide. Basic amino acids typically have positively charged side chains at physiological pH due to association with hydronium ion. Genetically encoded basic amino acids include L-His (H), L-Arg (R) and L-Lys (K).

"Polar Amino Acid or Residue" refers to a hydrophilic amino acid or residue having a side chain that is uncharged at physiological pH, but which has at least one bond in which the pair of electrons shared in common by two atoms is held more closely by one of the atoms. Genetically encoded polar amino acids include L-Asn (N), L-Gln (O), L-Ser (S) and L-Thr (T).

"Hydrophobic Amino Acid or Residue" refers to an amino acid or residue having a side chain exhibiting a hydrophobicity of greater than zero according to the normalized consensus hydrophobicity scale of Eisenberg et al., 1984, J. Mol. Biol. 179:125-142. Genetically encoded hydrophobic amino acids include L-Pro (P), L-Ile (I), L-Phe (F), L-Val (V), L-Leu (L), L-Trp (W), L-Met (M), L-Ala (A) and L-Tyr (Y).

"Aromatic Amino Acid or Residue" refers to a hydrophilic or hydrophobic amino acid or residue having a side chain that includes at least one aromatic or heteroaromatic ring. The aromatic or heteroaromatic ring may contain one or more substituents such as —OH, —OR", —SH, —SR", —CN, halogen (e.g., —F, —Cl, —Br, —I), —NO2, —NO, —NH2, —NHR", —NR"R", —C(O)R", —C(O)O—, —C(O)OH, —C(O)OR", —C(O)NH2, —C(O)NHR", —C(O)NR"R" and the like, where each R" is independently (C1-C6) alkyl, substituted (C1-C6) alkyl, (C2-C6) alkenyl, substituted (C2-C6) alkenyl, (C2-C6) alkynyl, substituted (C2-C6) alkynyl, (C5-C10) aryl, substituted (C5-C10) aryl, (C6-C16) arylalkyl, substituted (C6-C16) arylalkyl, 5-10 membered heteroaryl, substituted 5-10 membered heteroaryl, 6-16 membered heteroarylalkyl or substituted 6-16 membered heteroarylalkyl. Genetically encoded aromatic amino acids include L-Phe (F), L-Tyr (Y) and L-Trp (W). Although L-His (H) is classified above as a basic residue owing to the pKa of its heteroaromatic nitrogen atom, because its side chain includes a heteroaromatic ring, it may also be classified as an aromatic residue.

"Non-polar Amino Acid or Residue" refers to a hydrophobic amino acid or residue having a side chain that is uncharged at physiological pH and which has bonds in which the pair of electrons shared in common by two atoms is generally held equally by each of the two atoms (i.e., the side chain is not polar). Genetically encoded non-polar amino acids include L-Leu (L), L-Val (V), L-Ile (I), L-Met (M) and L-Ala (A).

"Aliphatic Amino Acid or Residue" refers to a hydrophobic amino acid or residue having an aliphatic hydrocarbon side chain. Genetically encoded aliphatic amino acids include L-Ala (A), L-Val (V), L-Leu (L) and L-Ile (I).

The amino acid L-Cys (C) is unusual in that it can form disulfide bridges with other L-Cys (C) amino acids or other sulfanyl- or sulfhydryl-containing amino acids. The "cysteine-like residues" include cysteine and other amino acids that contain sulfhydryl moieties that are available for formation of disulfide bridges. The ability of L-Cys (C) (and other amino acids with —SH containing side chains) to exist in a peptide in either the reduced free —SH or oxidized disulfide-bridged form affects whether L-Cys (C) contributes net hydrophobic or hydrophilic character to a peptide. While L-Cys (C) exhibits a hydrophobicity of 0.29 according to the normalized consensus scale of Eisenberg (Eisenberg et al., 1984, supra), it is to be understood that for purposes of the present disclosure L-Cys (C) is categorized as a polar hydrophilic amino acid, notwithstanding the general classifications defined above.

The amino acid Gly (G) is also unusual in that it bears no side chain on its α-carbon and, as a consequence, contributes only a peptide bond to a particular peptide sequence. Moreover, owing to the lack of a side chain, it is the only genetically-encoded amino acid having an achiral α-carbon. Although Gly (G) exhibits a hydrophobicity of 0.48 according to the normalized consensus scale of Eisenberg (Eisenberg et al., 1984, supra), for purposes of the present disclosure, Gly is categorized as an aliphatic amino acid or residue.

Owing in part to its conformationally constrained nature, the amino acid L-Pro (P) is also unusual. Although it is categorized herein as a hydrophobic amino acid or residue, it will typically occur in positions near the N- and/or C-termini so as not to deleteriously affect the structure of the polypeptides herein. However, as will be appreciated by skilled artisans, the polypeptides herein may include L-Pro (P) or other similar "conformationally constrained" residues at internal positions.

"Small Amino Acid or Residue" refers to an amino acid or residue having a side chain that is composed of a total three or fewer carbon and/or heteroatoms (excluding the α-carbon and hydrogens). The small amino acids or residues may be further categorized as aliphatic, non-polar, polar or acidic small amino acids or residues, in accordance with the above definitions. Genetically-encoded small amino acids include Gly, L-Ala (A), L-Val (V), L-Cys (C), L-Asn (N), L-Ser (S), L-Thr (T) and L-Asp (D).

"Hydroxyl-containing Amino Acid or Residue" refers to an amino acid or residue containing a hydroxyl (—OH) moiety. Genetically-encoded hydroxyl-containing amino acids include L-Ser (S) L-Thr (T) and L-Tyr (Y).

As will be appreciated by those of skill in the art, the above-defined categories are not mutually exclusive. Indeed, the delineated category of small amino acids includes amino acids from all of the other delineated categories except the aromatic category. Thus, amino acids having side chains exhibiting two or more physico-chemical properties can be included in multiple categories. As a specific example, amino acid side chains having heteroaromatic moieties that include ionizable heteroatoms, such as His, may exhibit both aromatic properties and basic properties, and can therefore be included in both the aromatic and basic categories. The appropriate classification of any amino acid or residue will be apparent to those of skill in the art, especially in light of the detailed disclosure provided herein.

While the above-defined categories have been exemplified in terms of the genetically encoded amino acids, the polypeptides described herein are not restricted to the genetically encoded amino acids. Indeed, in addition to the genetically encoded amino acids, the polypeptides described herein may be comprised, either in whole or in part, of naturally-occurring and/or synthetic non-encoded amino acids. Certain commonly encountered non-encoded amino acids of which the polypeptides described herein may be comprised include, but are not limited to: the D-enantiomers of the genetically-encoded amino acids; 2,3-diaminopropionic acid (Dpr); α-aminoisobutyric acid (Aib); ε-aminohexanoic acid (Aha); δ-aminovaleric acid (Ava); N-methylglycine or sarcosine (MeGly or Sar); ornithine (Orn); citrulline (Cit); t-butylalanine (Bua); t-butylglycine (Bug); N-methylisoleucine (MeIle); phenylglycine (Phg); cyclohexylalanine (Cha); norleucine (Nle); naphthylalanine (Nal); 2-chlorophenylalanine (Ocf); 3-chlorophenylalanine (Mcf); 4-chlorophenylalanine (Pcf); 2-fluorophenylalanine (Off); 3-fluorophenylalanine (Mff); 4-fluorophenylalanine (Pff); 2-bromophenylalanine (Obf); 3-bromophenylalanine (Mbf); 4-bromophenylalanine (Pbf); 2-methylphenylalanine (Omf); 3-methylphenylalanine (Mmf); 4-methylphenylalanine (Pmf); 2-nitrophenylalanine (Onf); 3-nitrophenylalanine (Mnf); 4-nitrophenylalanine (Pnf); 2-cyanophenylalanine (Ocf); 3-cyanophenylalanine (Mcf); 4-cyanophenylalanine (Pcf); 2-trifluoromethylphenylalanine (Otf); 3-trifluoromethylphenylalanine (Mtf); 4-trifluoromethylphenylalanine (Ptf); 4-aminophenylalanine (Paf); 4-iodophenylalanine (Pif); 4-aminomethylphenylalanine (Pamf); 2,4-dichlorophenylalanine (Opef); 3,4-dichlorophenylalanine (Mpcf); 2,4-difluorophenylalanine (Opff); 3,4-difluorophenylalanine (Mpff); pyrid-2-ylalanine (2pAla); pyrid-3-ylalanine (3pAla); pyrid-4-ylalanine (4pAla); naphth-1-ylalanine (1nAla); naphth-2-ylalanine (2nAla); thiazolylalanine (taAla); benzothienylalanine (bAla); thienylalanine (tAla); furylalanine (fAla); homophenylalanine (hPhe); homotyrosine (hTyr); homotryptophan (hTrp); pentafluorophenylalanine (5ff); styrylkalanine (sAla); authrylalanine (aAla); 3,3-diphenylalanine (Dfa); 3-amino-5-phenypentanoic acid (Afp); penicillamine (Pen); 1,2,3,4-tetrahydroisoquinoline-3-carboxylic acid (Tic); β-2-thienylalanine (Thi); methionine sulfoxide (Mso); N(w)-nitroarginine (nArg); homolysine (hLys); phosphonomethylphenylalanine (pmPhe); phosphoserine (pSer); phosphothreonine (pThr); homoaspartic acid (hAsp); homoglutanic acid (hGlu); 1-aminocyclopent-(2 or 3)-ene-4 carboxylic acid; pipecolic acid (PA), azetidine-3-carboxylic acid (ACA); 1-aminocyclopentane-3-carboxylic acid; allylglycine (aOly); propargylglycine (pgGly); homoalanine (hAla); norvaline (nVal); homoleucine (hLeu), homovaline (hVal); homoisolencine (hIle); homoarginine (hArg); N-acetyl lysine (AcLys); 2,4-diaminobutyric acid (Dbu); 2,3-diaminobutyric acid (Dab); N-methylvaline (MeVal); homocysteine (hCys); homoserine (hSer); hydroxyproline (Hyp) and homoproline (hPro). Additional non-encoded amino acids of which the polypeptides described herein may be comprised will be apparent to those of skill in the art (see, e.g., the various amino acids provided in Fasman, 1989, CRC Practical Handbook of Biochemistry and Molecular Biology, CRC Press, Boca Raton, Fla., at pp. 3-70 and the references cited therein, all of which are incorporated by reference). These amino acids may be in either the L- or D-configuration.

Those of skill in the art will recognize that amino acids or residues bearing side chain protecting groups may also comprise the polypeptides described herein. Non-limiting examples of such protected amino acids, which in this case belong to the aromatic category, include (protecting groups listed in parentheses), but are not limited to: Arg(tos), Cys (methylbenzyl), Cys (nitropyridinesulfenyl), Glu(δ-benzylester), Gln(xanthyl), Asn(N-δ-xanthyl), His(bom), His(benzyl), His(tos), Lys(fmoc), Lys(tos), Ser(O-benzyl), Thr (O-benzyl) and Tyr(O-benzyl).

Non-encoding amino acids that are conformationally constrained of which the polypeptides described herein may be composed include, but are not limited to, N-methyl amino acids (L-configuration); 1-aminocyclopent-(2 or 3)-ene-4-carboxylic acid; pipecolic acid; azetidine-3-carboxylic acid; homoproline (hPro); and 1-aminocyclopentane-3-carboxylic acid.

The classifications of the genetically encoded and certain common non-encoded amino acids according to the categories defined above are summarized in Table 1, below. It is to be understood that Table 1 is for illustrative purposes only and does not purport to be an exhaustive list of amino acids that can comprise the polypeptides described herein. Other amino acids not specifically mentioned herein can be readily categorized based on their observed physical and chemical properties in light of the definitions provided herein.

One or more linkages, but typically one linkage in the polypeptides described herein may also represent a linker. Such linkers may be useful in situations where the polypeptides, owing in part to their small size, are under significant conformational strain when composed wholly of amide linkages or the other linkages described above. Such linkers may be composed of virtually any combination of atoms suitable for linking two ends of a peptide or peptide analog together. Linkers can include flexible moieties such as saturated hydrocarbons and ethers or polyethers. In a specific embodiment, one linkage represents —C(O)—(CH2)m-NH—, —C(O)—(CH2)m-O—, —C(O)—(CH2)m-S—, —C(O)—(CH2-O—CH2)p-NH—, —C(O)—(CH2-O—CH2)p-O— or —C(O)—(CH2-O—CH2)p-S—, where m is an integer from 3 to 5 and p is an integer from 1 to 3. Other suitable linkers, as well as methods of synthesizing polypeptides including such linkers, will be apparent to those of skill in the art.

TABLE 1

Encoded and Certain Common Non-Encoded Amino Acid Classifications

| Classification | Encoded Amino Acids | Non-encoded Amino Acids |
|---|---|---|
| Hydrophobic | | |
| Aromatic | F, Y, W, H | f, y, w, h, Phg, Nal, Thi, Tic, Pcf, Off, Mff, Pff, hPhe |
| Non-Polar | L, V, I, M, G, A, P | l, v, i, m, g, a, p, Bua, Bug, MeIle, Nle, MeVal, Cha, MeGly, Aib |
| Aliphatic | A, V, L, I | a, v, l, i, Dpr, Aib, Aha, MeGly, Bua, Bug, Mele, Cha, Nle, MeVal |
| Hydrophilic | | |
| Acidic | D, E | d, e |
| Basic | H, K, R | h, k, r, Dpr, Orn, hArg, Paf, Dbu, Dab |
| Polar | C, Q, N, S, T | c, q, n, s, t, Cit, AcLys, Mso, hSer |
| Small | G, A, V, C, N, S, T, D | g, a, v, c, n, s, t, d |

In the polypeptides described herein, the symbol "~" between each specified residue X" designates a backbone constitutive linking moiety. In the polypeptides described herein, each "~" between the various X" represents an amide or peptide linkage of the following polarity: —C(O)—NH—. It is to be understood, however, that the polypeptides described herein may include analogs of peptides in which one or more amide or peptide linkages are replaced with a linkage other than an amide or peptide linkage, such as a substituted amide linkage, an isostere of an amide linkage, or a peptido or amide mimetic linkage. Thus, when used in connection with defining the various X" comprising the polypeptides described herein, the term "residue" refers to the $C_\alpha$ carbon and side chain moiety(ies) of the designated amino acid or class of amino acid. As a specific example, defining $X^1$ as being a "Gly residue" means that $X^1$ is $C_\alpha H_2$. Defining $X^1$ as being an "Ala residue" means that $X^1$ is $C_\alpha HCH_3$ in which the $C_\alpha$ carbon is in either the D- or L-configuration. Defining $X^1$ as being an "A residue" means that $X^1$ is $C_\alpha HCH_3$ in which the $C_\alpha$ carbon is in the L-configuration.

Substituted amide linkages that may be included in the polypeptides described herein include, but are not limited to, groups of the formula —C(O)NR2, where R2 is (C1-C6) alkyl, (C5-C10) aryl, substituted (C5-C10) aryl, (C6-C16) arylalkyl, substituted (C6-C16) arylalkyl, 5-10 membered heteroaryl, substituted 5-10 membered heteroaryl, 6-16 membered heteroarylalkyl or substituted 6-16 membered heteroarylalkyl.

Isosteres of amides that may be included in the polypeptides described herein generally include, but are not limited to, —NR3-SO—, —NR3-S(O)2-, —CH2-CH2-, —CH=CH— (cis and trans), —CH2-NH—, —CH2-S—, —CH2-O—, —C(O)—CH2-, —CH(OH)—CH2- and —CH2-S(O)$_2$—, where R3 is hydrogen or R2 and R2 is as previously defined. These interlinkages may be included in the polypeptides described herein in either the depicted polarity or in the reverse polarity. Peptide analogs including such non-amide linkages, as well as methods of synthesizing such analogs, are well-known. See, for example, Spatola, 1983, "Peptide Backbone Modifications," In: Chemistry and Biochemistry of Amino Acids, Peptides and Proteins, Weinstein, Ed., Marcel Dekker, New York, pp. 267-357 (general review); Morley, 1980, Trends Pharm. Sci. 1:463-468; Hudson et al., 1979, Int. J. Prot. Res. 14:177-185 (—CH2-NH—, —CH2-CH2); Spatola et al., 1986, Life Sci. 38:1243-1249; Spatola, 1983, "Peptide Backbone Modifications: the Ψ [CH2S] Moiety as an Amide Bond Replacement," In: Peptides: Structure and Function V, J. Hruby and D. H. Rich, Eds., Pierce Chemical Co., Rockford, Ill., pp. 341-344 (—CH2-S—); Hann, 1982, J. Chem. Soc. Parkin Trans. I. 1:307-314 (—CH=CH—, cis and trans); Almquist et al., 1980, J. Med. Chem. 23:1392-1398 (—C(O)—CH2-); European Patent Application EP 45665; Chemical Abstracts CA 97:39405 (—CH(OH)—CH2-); Holladay et al., 1983, Tetrahedron Lett. 24:4401-4404 (—CH(OH)—CH2-); and Hruby, 1982, Life Sci. 31:189-199 (—CH2-S—).

Alternatively, one or more amide linkages may be replaced with peptidomimetic and/or amide mimetic moieties. Non-limiting examples of such moieties are described in Olson et al., 1993, J. Med. Chem. 36:3039-3049; Ripka & Rich, 1998, Curr. Opin. Chem. Biol. 2:441-452; Borchardt et al., 1997, Adv. Drug. Deliv. Rev. 27:235-256 and the various references cited therein.

5.3 Detailed Description

5.3.1 Directed Evolution of Polypeptides

Methodologies for screening and identifying polypeptides for desired activities are useful in the preparation of new compounds such as modified enzymes and/or new pharmaceuticals. Directed evolution can be used to discover or enhance activity of polypeptides of commercial interest. For example, if the activity of a known catalyst is insufficient for a commercial process, directed evolution and/or other protein engineering technologies may be used to make appropriate improvements to the catalyst to improve activity on the substrate of interest. Current methodologies are often limited by time and cost factors. In some instances, it may take months or years, at great expense, to find a new polypeptide with the desired activity, if one is ever found. Furthermore, the number of polypeptide variants that must be screened is often cumbersome. Thus, there is a long felt need for compositions and methods used to identify novel polypeptide variants having a desired activity.

Many methodologies directed to the design and/or identification of polypeptides having particular characteristics are known in the art. For example, methods for high-throughput screening arrays of clones in a sequential manner are presented in PCT Publication No. WO 01/32858; an in vitro selection method of screening a library of catalyst molecules is disclosed in PCT Publication No. WO 00/11211; a screening method for identifying active peptides or proteins with improved performance is disclosed in PCT Publication No. WO 02/072876 and US Patent Application Publication No. 2004/0132039; a methods for creating and screening transgenic organisms having desirable traits are disclosed in U.S. Pat. No. 7,033,781; methods for making circularly permuted proteins and peptides having novel and/or enhanced functions with respect to a native protein or peptide are disclosed in PCT Publication No. WO 2006/086607; methods for preparing variants of a catalytic polypeptide are disclosed in US Patent Application Publication No. 2003/0073109; and methods for biopolymer engineering using a variant set to model sequence-activity relationships are disclosed in PCT Publication No. WO 2005/013090; each of which is incorporated herein by reference in its entirety.

In some aspects, the present disclosure provides a plurality of addressable polypeptides, a portion of each polypeptide having known amino acid sequence, wherein each polypeptide reacts with a substrate to produce a product, and wherein at least two members of the plurality are related to a parent polypeptide and react with differing levels of activity upon a given substrate. In some aspects, the present disclosure provides a plurality of addressable polypeptides, a portion of each polypeptide having known amino acid sequence, wherein each polypeptide reacts with a substrate to produce a product, and wherein at least two members of the plurality are related to a parent polypeptide and react with different substrates.

In some embodiments, each member of the plurality acts on a different substrate.

In some embodiments, some members of the plurality act on one substrate and other members of the plurality act on at least one other substrate.

In some embodiments, at least two members of the plurality differ with respect to one or more of the following properties: substrate specificity, chemoselectivity, regioselectivity, stereoselectivity, stereospecificity, ligand specificity, receptor agonism, receptor antagonism, conversion of a cofactor.

In some embodiments, the members of the plurality that act on the same substrate differ with respect to one or more of the following properties: rate of product formation, percent conversion of a substrate to a product, or percent conversion of a cofactor.

In some embodiments, at least two members of the plurality are operable over a broad pH range, such as for example, from about pH 2 to about pH 14, from about pH 2 to about pH 12, from about pH 3 to about pH 10, or from about pH 5 to about pH 10. Other pH ranges will be apparent to the skilled artisan.

In some embodiments, at least two members are operable over a broad range of temperatures, such as for example, a range of from about 4° C. to about 80° C., from about 4° C. to about 70° C., or from about 4° C. to about 60° C., or from about 4° C. to about 50° C. Other ranges will be apparent to the skilled artisan.

In some embodiments, at least two members are operable in a solution containing from about 10 to about 50% or more % organic solvent.

In some embodiments, each member of the plurality is an evolvant of the same ancestor or parent enzyme and contains at least one mutation as compared to the ancestor or parent enzyme. In some embodiments, a plurality comprises one or more "control" polypeptides as well as several "test" polypeptides. In some embodiments, the test polypeptides are all related to a parent polypeptide. In some embodiments, the control and the test polypeptides are all related to a parent polypeptide. The ancestor or parent enzyme need not have an amino acid sequence identical to the amino acid sequence of the wild type enzyme. In some embodiments, the ancestor or parent enzyme is the wild type enzyme. In some embodiments, the ancestor or parent enzyme has been mutated as compared to the wild type enzyme.

In some embodiments, the plurality comprises subsets of members in which each subset comprises evolvants from a separate ancestor or parent enzyme.

In some aspects, the present disclosure provides a plurality of pluralities in which each plurality acts on a different class of substrate.

In some aspects, all members of a plurality can undergo the same chemical reaction on a given class of substrates. In some aspects, all members of a plurality can undergo the same chemical reaction on a given substrate.

In some aspects, the present disclosure provides a plurality of enzyme candidates made by generating variants of at least one parent enzyme, wherein at least a portion of the amino acid sequence of each variant is known, and wherein each variant comprises at least one mutation known to affect reactivity with a substrate to produce a product, and selecting two or more variants wherein at least two of the selected variants react with differing levels of activity upon a given substrate. In some aspects, the present disclosure provides a plurality of enzyme candidates made by generating variants of at least one parent enzyme, wherein at least a portion of the amino acid sequence of each variant is known, and wherein each variant comprises at least one mutation known to affect reactivity with a substrate to produce a product, and selecting two or more variants wherein at least two of the selected variants react with different substrates.

In some embodiments, the selected variants can be placed onto a surface. In some embodiments, the surface comprises a microtiter plate. In some embodiments, the surface comprises a set of 2 to 4 microtiter plates. In some embodiments, the surface comprises a microchip. In some embodiments, the surface comprises glass. In some embodiments, the surface comprises plastic.

In some embodiments, the variants are expressed from polynucleotides. In some embodiments, the variants are chemically synthesized.

In some aspects, the present disclosure provides a plurality of addressable polypeptide variants made by a process of generating a plurality of polypeptide variants related to a parent polypeptide, each variant having a different amino acid sequence, wherein each variant comprises at least one mutation that enhances reactivity with a ligand as compared to the reactivity of the parent polypeptide with said ligand, and wherein at least two variants of the plurality react with differing levels of activity upon a given ligand; and assigning an address to each of the variants. In some aspects, the present disclosure provides a plurality of addressable polypeptide variants made by a process of generating a plurality of polypeptide variants related to a parent polypeptide, each variant having a different amino acid sequence, wherein each variant comprises at least one mutation that enhances reactivity with a ligand as compared to the reactivity of the parent polypeptide with said ligand, and wherein at least two variants of the plurality react with different ligands; and assigning an address to each of the variants.

In some aspects, the present disclosure provides a method useful for identifying at least one polypeptide having a desired activity, comprising screening a plurality of polypeptide variants against a ligand of interest, wherein each variant reacts with at least one ligand to produce a detectable signal, and wherein at least two members of the plurality are related to a parent polypeptide and react with differing levels of activity upon a given ligand, and identifying at least one variant that produces a signal upon reaction with the ligand of interest. In some aspects, the present disclosure provides a method useful for identifying at least one polypeptide having a desired activity, comprising screening a plurality of polypeptide variants against a ligand of interest, wherein each variant reacts with at least one ligand to produce a detectable signal, and wherein at least two members of the plurality are related to a parent polypeptide and react with different ligands; and identifying at least one variant that produces a signal upon reaction with the ligand of interest. In some embodiments, the method further comprises identifying at least a second variant that produces a signal of interest upon reaction with the ligand of interest; postulating a sequence-activity relationship between the amino acid residues within the identified variants and the ability of each variant to produce a detectable signal; generating a second plurality of polypeptide variants based on the sequence-activity relationship; screening the second plurality against the ligand of interest; and identifying at least one variant from the second plurality that produces an enhanced signal of interest as compared to the earlier identified variants from the first plurality.

In some embodiments, the identity of the ligand of interest is unknown. In some embodiments, the ligand of interest is of unknown composition or chemical identity.

In some embodiments, each variant is an enzyme and the ligand of interest is a candidate substrate for the enzyme. In some embodiments, each variant comprises a binding pocket of an enzyme and the ligand of interest is a candidate substrate for the enzyme.

In some embodiments, each variant is a receptor and the ligand of interest is a candidate ligand for the receptor. In some embodiments, each variant comprises a ligand binding site of a receptor and the ligand of interest is a candidate ligand for the receptor.

In some embodiments, two or more members of the plurality differ in the kind of signal produced. In some embodiments, the kind of signal produced is selected from a signal indicating substrate specificity, chemoselectivity, regioselectivity, stereoselectivity, stereospecificity, ligand specificity, receptor agonism, receptor antagonism, conversion of a cofactor, or any combination thereof.

In some embodiments, two or more members of the plurality differ in the level of signal produced. In some embodiments, the difference in level is a difference in rate of product formation, percent conversion of a substrate to a product, or percent conversion of a cofactor.

In some aspects, the present disclosure provides host cells which produce the variants identified in the methods described herein. In some aspects, the enzyme is recombinantly expressed by a host cell, and the host cell is a member of the plurality.

In some aspects, the present disclosure provides a plurality of host cell colonies or cultures, wherein each colony or culture expresses the at least one variant identified in the methods described herein.

In some aspects, the present disclosure provides a method of making a plurality of addressable polypeptide variants, comprising generating a plurality of polypeptide variants related to a parent polypeptide, a portion of each variant having known amino acid sequence, wherein each variant comprises at least one mutation that enhances reactivity with a substrate as compared to the reactivity of the parent polypeptide with said substrate, and wherein at least two members of the plurality react with differing levels of activity upon a given substrate; and assigning an address to each of the variants. In some aspects, the present disclosure provides a method of making a plurality of addressable polypeptide variants, comprising generating a plurality of polypeptide variants related to a parent polypeptide, a portion of each variant having known amino acid sequence, wherein each variant comprises at least one mutation that enhances reactivity with a substrate as compared to the reactivity of the parent polypeptide with said substrate, and wherein at least two members of the plurality react with different substrates; and assigning an address to each of the variants.

In some aspects, the present disclosure provides a method of making a plurality of addressable pluralities, comprising generating a first and a second addressable plurality of polypeptide variants, wherein the members of the first plurality are related to one parent polypeptide and the members of the second plurality are related to a second parent polypeptide, wherein at least a portion of the amino acid sequence of each variant is known, wherein each member of each plurality reacts with a substrate to produce a product, and wherein at least one member of the first plurality and at least one member of the second plurality react with different substrates. In some aspects, the present disclosure provides a method of making a plurality of addressable pluralities, comprising generating a first and a second addressable plurality of polypeptide variants, wherein the members of the first plurality are related to one parent polypeptide and the members of the second plurality are related to a second parent polypeptide, wherein at least a portion of the amino acid sequence of each variant is known, wherein each member of each plurality reacts with a substrate to produce a product, and wherein at least one member of the first plurality and at least one member of the second plurality react with differing levels of activity upon a given substrate In some aspects, the present disclosure provides a kit for identifying at least one polypeptide having a desired activity, comprising at least one plurality of polypeptides, wherein each member of each plurality reacts with at least one ligand to produce a detectable signal, and wherein at least two members of each plurality are related to a parent polypeptide and react with differing levels of activity upon a given substrate. In some aspects, the present disclosure provides a kit for identifying at least one polypeptide having a desired activity, comprising at least one plurality of polypeptides, wherein each member of each plurality reacts with at least one ligand to produce a detectable signal, and wherein at least two members of each plurality are related to a parent polypeptide and react with different ligands. In some embodiments, the kit includes instructions for use.

In some embodiments, the plurality of polypeptide variants includes a plurality of polypeptides having expanded diversity toward a variety of different substrates. In some embodiments, the plurality can comprise multiple pools, arrays, libraries, or microtiter plates, as described above.

In various embodiments, the plurality of polypeptides is "tunable" using methods of generating mutations based on sequence-activity relationship maps. A first, pre-tuned plurality can be screened to identify at least one polypeptide having enhanced activity for a candidate substrate. The one or more polypeptides identified from the first, pre-tuned plurality can then be used as the basis for generating a fine-tuned, higher resolution second plurality for screening the candidate substrate. These steps of screening and using the results to generate still finer-tuned, still higher resolution pluralities can be reiterated. In this way, novel polypeptides with a desired activity can be identified. A first plurality can be screened with a novel, unknown or naïve substrate or ligand and a second plurality populated with second generation variants is generated before testing with the novel, unknown or naïve substrate or ligand. In some embodiments, the first plurality screened is a pre-tuned plurality and the second plurality screened is a fine-tuned plurality.

In some embodiments, a sufficient number of variants of the pre-tuned plurality (e.g., greater than about ten variants) exhibit activity on a candidate substrate so that protein sequence activity relationship (ProSAR)-type algorithms may be used to predict beneficial and detrimental mutations among the active variants. The putative more beneficial mutations can then be combined in new variants in a fine-tuned plurality. ProSAR-type algorithms are described in U.S. Patent Application Publication Nos. 2004/0072245, 2004/0161796, and 2005/0084907, and 2006/0205003, each of which are incorporated herein by reference The number of variants per plurality can be at least 20, 40, 60, 100, 200, 300 or more. In theory, the number of variants can be up to the theoretical limit of possible variants of a given polypeptide of discrete length. For example, for a polypeptide of 100 amino acid residues, and considering only the 20 possible substitutions using naturally occurring amino acids at each residue position, the theoretical limit of possible variants is $100^{20}$.

At least some structural information about the starting polypeptide is often known. A polypeptide in the plurality can comprise a full length variant of the ancestral or parent polypeptide, or can comprise a truncated variant comprising the binding pocket of an enzyme or the binding site of a receptor. Each polypeptide member of a plurality may or may not act as an enzyme or receptor with any given substrate or ligand of interest.

In some embodiments, the binding pocket of a wild type or an ancestral enzyme is predicted or has been demonstrated to be malleable (tolerant of mutations while retaining activity). One or multiple amino acids can be substituted in the variant as compared to the ancestor or parent enzyme.

In some embodiments, the polynucleotide encoding the wild type or ancestral polypeptide has been determined to be expressed at high levels. In some embodiments, the polynucleotide encoding the parent polypeptide has been engineered to be expressed at high levels, for example by codon optimization. In some embodiments, the parent polypeptide has been engineered so that a polynucleotide encoding it is expressed at high levels. In some embodiments, the wild type or ancestral polypeptide has been engineered to generate an evolved parent polypeptide that is more robust to pH, temperature and/or solvent conditions than is the wild type or ancestral polypeptide. In some embodiments, the parent polypeptide has been determined or engineered to be easily manufactured for large scale production.

Enzymes suitable for use in the compositions and methods described herein, whether naturally occurring or non-naturally occurring, can be readily identified by those having ordinary skill in the art. Non-naturally enzymes can be generated using known methods, including, for example, mutagenesis, directed evolution, and the like.

In some embodiments, generation of the plurality of polypeptides can be based on: libraries incorporating mutations previously identified in the literature which affect substrate specificity, selectivity or stability; structural modeling; computationally predicted improvements of protein folding pattern (packing the interior residues of a protein to make it more solid inside); ligand binding and docking studies; libraries designed to optimize subunit interactions; family shuffling between multiple diverse homologs; semi-synthetic shuffling using diversity from homologs; gene synthesis; site-directed mutagenesis; saturating random mutagenesis of the binding pocket; semi-synthetic combinatorial libraries of residues within the binding pocket; directed evolution; and recursive sequence recombination (RSR) (see, eg., US Patent Application No. 2006/0223143, incorporated by reference herein in its entirety).

In some embodiments, the plurality of variants can be made by subjecting an ancestral polypeptide, which may or may not be a wild type enzyme) to a variety of mutagenesis techniques used in the art for generating variants (e.g., modified) polypeptides, such as in vitro mutagenesis or directed evolution to generate an evolved parent enzyme, which can be used as the basis for generating variants to populate the plurality. In some embodiments, directed evolution is an attractive method for generating such enzymes or polypeptides because of the relative ease of generating mutations throughout the whole of the gene coding for the polypeptide, as well as providing the ability to take previously mutated polynucleotides and subjecting them to additional cycles of mutagenesis and/or recombination to obtain further improvements in a selected enzyme property. Subjecting the whole gene to mutagenesis can reduce the bias that may result from restricting the changes to a limited region of the gene. It can also enhance generation of enzymes affected in different enzyme properties since distantly spaced parts of the enzyme may play a role in various aspects of enzyme function. Mutagenesis and directed evolution techniques useful for the purposes herein are amply described in the literature: Ling, et al., 1997, "Approaches to DNA mutagenesis: an overview," *Anal. Biochem.* 254(2):157-78; Dale et al., 1996, "Oligonucleotide-directed random mutagenesis using the phosphorothioate method," *Methods Mol. Biol.* 57:369-74; Smith, 1985, "In vitro mutagenesis," *Ann. Rev. Genet.* 19:423-462; Botstein et al., 1985, "Strategies and applications of in vitro mutagenesis," *Science* 229:1193-1201; Carter, 1986, "Site-directed mutagenesis," *Biochem. J.* 237:1-7; Kramer et al., 1984, "Point Mismatch Repair," *Cell,* 38:879-887; Wells et al., 1985, "Cassette mutagenesis: an efficient method for generation of multiple mutations at defined sites," *Gene* 34:315-323; Wise et al., 2004, "Understanding the Importance of Protein Structure to Nature's Routes for Divergent Evolution in TIM Barrel Enzymes," *Accounts of Chemical Research* 37(3):149-158; James et al., 2003, "Conformational diversity and protein evolution—a 60-year-old hypothesis revisited," *Trends Biochem Sci* 28(7):361-368; Aharoni et al., 2005, "The 'evolvability' of promiscuous protein functions," *Nature Genetics* 37(1):73-76; O'Brien et al., 1999, "Catalytic promiscuity and the evolution of new enzymatic activities," *Chemistry and Biology* 6(4):R91-R105; Copley, 2003, "Enzymes with extra talents: moonlighting functions and catalytic promiscuity," *Curr Opin Chem Biol* 7:265-272; Yoshikuni et al., 2006, "Designed divergent evolution of enzyme function," *Nature* 440(7087):1078-82; Nowlan et al., 2006, "Resolution of Chiral Phosphate, Phosphonate, and Phosphinate Esters by an Enantioselective Enzyme Library," *J Am Chem Soc* 128(49):15892-902; Yazbeck et al., 2003, "Automated Enzyme Screening Methods for the Preparation of Enantiopure Pharmaceutical Intermediates," *Adv Synth Catal* 345(4):524-32; Minshull et al., 1999, "Protein evolution by molecular breeding," *Curr Opin Chem Biol* 3:284-290; Christians et al., 1999, "Directed evolution of thymidine kinase for AZT phosphorylation using DNA family shuffling," *Nature Biotech* 17:259-264; Crameri et al., 1998, "DNA shuffling of a family of genes from diverse species accelerates directed evolution," *Nature* 391:288-291; Crameri et al., 1997, "Molecular evolution of an arsenate detoxification pathway by DNA shuffling," *Nature Biotech* 15:436-438; Zhang et al., 1997, "Directed evolution of an effective fructosidase from a galactosidase by DNA shuffling and screening," *Proc Natl Acad Sci USA* 94:45-4-4509; Crameri et al., 1996, "Improved green fluorescent protein by molecular evolution using DNA shuffling,' *Nature Biotech* 14:315-319; Stemmer, 1994, "Rapid evolution of a protein in vitro by DNA shuffling," *Nature* 370:389-391; Stemmer, 1994, "DNA shuffling by random fragmentation and reassembly: In vitro recombination for molecular evolution," *Proc Natl Acad Sci USA* 91:10747-10751; PCT Publications WO 95/22625; WO 97/0078; WO 97/35966; WO 98/27230; WO 00/42651; WO 01/75767; and U.S. Pat. Nos. 6,537,746, 7,098,010 and 7,115,403. All publications are incorporated herein by reference.

Candidate enzymes useful in the compositions and methods described herein may be capable of catalyzing an enantioselective reduction reaction, for example. Such enzymes can be used to make intermediates useful in the synthesis of pharmaceutical compounds. For example, certain halohydrin dehalogenase and ketoreductase enzymes are useful in carrying out reactions that generate intermediate compounds useful in the synthesis of cholesterol lowering HMG-CoA reductase inhibitors ("statins") (see, e.g., U.S. Pat. Nos. 7,125,693, and 7,132,267). Such enzymes have been engineered using laboratory evolution technologies, such as DNA shuffling, to yield non-naturally occurring engineered enzymes with improved properties as compared to the naturally-occurring wild type enzyme obtained from organisms such as *Saccharomyces cerevisiae,* for example.

A representative list of families or classes of enzymes which may be mutagenized in accordance with the aspects of the present disclosure, includes the following enzymes and their functions:

1. Lipases/Esterases
    a. Enantioselective hydrolysis of esters (lipids)/thioesters
        1) Resolution of racemic mixtures
        2) Synthesis of optically active acids or alcohols from meso-diesters
    b. Selective synthesis
        1) Regiospecific hydrolysis of carbohydrate esters
        2) Selective hydrolysis of cyclic secondary alcohols
    c. Synthesis of optically active esters, lactones, acids, alcohols
        1) Transesterification of activated/nonactivated esters
        2) Interesterification
        3) Optically active lactones from hydroxyesters
        4) Regio- and enantioselective ring opening of anhydrides
    d. Detergents
    e. Fat/Oil conversion
    f. Cheese ripening 2. Proteases
   a. Ester/amide synthesis
   b. Peptide synthesis
   c. Resolution of racemic mixtures of amino acid esters
   d. Synthesis of non-natural amino acids
   e. Detergents/protein hydrolysis
3. Glycosidases/Glycosyl Transferases
   a. Sugar/polymer synthesis
   b. Cleavage of glycosidic linkages to form mono, di- and oligosaccharides
   c. Synthesis of complex oligosaccharides
   d. Glycoside synthesis using UDP-galactosyl transferase
   e. Transglycosylation of disaccharides, glycosyl fluorides, aryl galactosides
   f. Glycosyl transfer in oligosaccharide synthesis
   g. Diastereoselective cleavage of beta-glucosylsulfoxides
   h. Asymmetric glycosylations
   i. Food processing
   j. Paper processing
4. Phosphatases/Kinases and dephosphorylases
   a. Synthesis/hydrolysis of phosphate esters
      1) Regio-, enantioselective phosphorylation
      2) Introduction of phosphate esters
      3) Synthesize phospholipid precursors
      4) Controlled polynucleotide synthesis
   b. Activate biological molecule
   c. Selective phosphate bond formation without protecting groups
5. Mono/Dioxygenases
   a. Direct oxyfunctionalization of unactivated organic substrates
   b. Hydroxylation of alkane, aromatics, steroids
   c. Epoxidation of alkenes
   d. Enantioselective sulphoxidation
   e. Regio- and stereoselective Bayer-Villiger oxidations
6. Haloperoxidases
   a. Oxidative addition of halide ion to nucleophilic sites
   b. Addition of hypohalous acids to olefinic bonds
   c. Ring cleavage of cyclopropanes
   d. Activated aromatic substrates converted to ortho and para derivatives
   e. 1.3 diketones converted to 2-halo-derivatives
   f. Heteroatom oxidation of sulfur and nitrogen containing substrates
   g. Oxidation of enol acetates, alkynes and activated aromatic rings
7. Lignin Peroxidase/Diarylpropane Peroxidases
   a. Oxidative cleavage of C—C bonds
   b. Oxidation of benzylic alcohols to aldehydes
   c. Hydroxylation of benzylic carbons
   d. Phenol dimerization
   e. Hydroxylation of double bonds to form diols
   f. Cleavage of lignin aldehydes
8. Epoxide Hydrolases
   a. Synthesis of enantiomerically pure bioactive compounds
   b. Regio- and enantioselective hydrolysis of epoxide
   c. Aromatic and olefinic epoxidation by monooxygenases to form epoxides
   d. Resolution of racemic epoxides
   e. Hydrolysis of steroid epoxides
9. Nitrile Hydratase/Nitrilases
   a. Hydrolysis of aliphatic nitrites to carboxamides
   b. Hydrolysis of aromatic, heterocyclic, unsaturated aliphatic nitrites to corresponding acids
   c. Hydrolysis of acrylonitrile
   d. Production of aromatic and carboxamides, carboxylic acids (nicotinamide, picolinamide, isonicotinamide)
   e. Regioselective hydrolysis of acrylic dinitrile
   f. alpha.-amino acids from .alpha.-hydroxynitriles
10. Transaminases
    a. Transfer of amino groups into oxo-acids to produce amino acids.
    b. Transfer of amino groups to ketones to produce chiral amines.
    c. Resolution of chiral amines by transfer of amino groups to ketones.
11. Amidases/Acylases
    a. Hydrolysis of amides, amidines, and other C—N bonds
    b. Non-natural amino acid resolution and synthesis
    c. Formation of amide bonds from amines and carboxylic acids, esters, and amides.
12. Ketoreductases
    a. Reduction of ketones to chiral alcohols
    b. Resolution of chiral alcohols by oxidation to ketones or aldehydes.
13. Enone Reductases
    a. Reduction of C=C double bonds in conjugation with an electron withdrawing group, e.g. carboxylic acid ester, nitrile, nitro, keto, and the like.

This list, while illustrating certain specific aspects of the possible enzymes of the disclosure, is not considered exhaustive and does not portray the limitations or circumscribe the scope of the disclosure.

Examples of cellular receptors (and their corresponding ligands) are well-known in the art. Exemplary receptors include, among others, steroid receptors, cytokine receptors, growth factor receptors, intracellular kinases, tyrosine receptor kinases, metabotropic receptors, G-protein coupled receptors (e.g., seven transmembrane receptors), transcription factors, etc.

5.3.2 Chemical Synthesis of Peptides

Polypeptide compounds may be prepared using standard techniques of organic synthesis. For example, polypeptides may be prepared using conventional step-wise solution or solid phase synthesis (see, e.g., *Chemical Approaches to the Synthesis of Peptides and Proteins*, Williams et al., Eds., 1997, CRC Press, Boca Raton Fla., and references cited therein; *FMOC Solid Phase Peptide Synthesis: A Practical Approach*, Chan & White, Eds., 2000, IRL Press, Oxford, England, and references cited therein).

Alternatively, polypeptide compounds may be prepared by way of segment condensation, as described, for example, in Liu et al., 1996, Tetrahedron Lett. 37(7):933-936; Baca et al., 1995, J. Am. Chem. Soc. 117:1881-1887; Tam et al., 1995, Int. J. Peptide Protein Res. 45:209-216; Schnolzer and Kent, 1992, Science 256:221-225; Liu and Tam, 1994, J. Am. Chem. Soc. 116(10):4149-4153; Liu and Tam, 1994, Proc. Natl. Acad. Sci. USA 91:6584-6588; Yamashiro and Li, 1988, Int. J. Peptide Protein Res. 31:322-334. The condensation technique is particularly useful for synthesizing polypeptides comprising Gly residues. Other methods useful for synthesizing polypeptides are described in Nakagawa et al., 1985, J. Am. Chem. Soc. 107:7087-7092. Polypeptides that are peptide analogs may be synthesized using the various methods described in the references cited in connection with amide isosteres and amide and peptidomimetics, supra.

Polypeptide compounds containing N- and/or C-terminal blocking groups can be prepared using standard techniques of organic chemistry. For example, methods for acylating the N-terminus of a peptide or amidating or esterifying the C-terminus of a peptide are well-known in the art. Modes of carrying other modifications at the N- and/or C-terminus will be apparent to those of skill in the art, as will modes of protecting any side-chain functionalities as may be necessary to attach terminal blocking groups.

Formation of disulfide linkages, if desired, is generally conducted in the presence of mild oxidizing agents. Chemical oxidizing agents may be used, or the compounds may simply be exposed to atmospheric oxygen to effect these linkages. Various methods are known in the art, including those described, for example, by Tam et al., 1979, Synthesis 955-957; Stewart et al., 1984, Solid Phase Peptide Synthesis, 2d Ed., Pierce Chemical Company Rockford, Ill.; Ahmed et al., 1975, J. Biol. Chem. 250:8477-8482; and Pennington et al., 1991 Peptides 1990 164-166, Giralt and Andreu, Eds., ESCOM Leiden, The Netherlands. An additional alternative is described by Kamber et al., 1980, Helv. Chim. Acta 63:899-915. A method conducted on solid supports is described by Albericio, 1985, Int. J. Peptide Protein Res. 26:92-97. Any of these methods may be used to form disulfide linkages in the polypeptides described herein.

Cyclic peptides may be prepared or may result from the formation of single or multiple disulfide bonds, other sidechains or head-to-tail cyclizations, either directly or by way of an optional linker. The cyclic peptides may be prepared using any art-known techniques for the preparation of cyclic peptides and cyclic peptide analogs. For example, the peptide or peptide analog may be prepared in linear or non-cyclized form using conventional solution or solid phase peptide and/or peptide analog syntheses and cyclized using standard chemistries. The linear polypeptides can be cyclized with a linking group between the two termini, between one terminus and the side chain of an amino acid in the peptide or peptide derivative, or between the side chains to two amino acids in the peptide or peptide derivative. Suitable procedures for synthesizing the peptide and peptide analogs described herein, as well as suitable chemistries for cyclizing such compounds, are well known in the art. For references related to synthesis of cyclic peptides the reader is referred to Tam et al., 2000, Biopolymers 52:311-332; Camamero et al, 1998, Angew. Chem. Intl. Ed. 37: 347-349; Tam et al., 1998, Prot. Sci. 7:1583-1592; Jackson et al., 1995, J. Am. Chem. Soc. 117:819-820; Dong et al., 1995, J. Am. Chem. Soc. 117:2726-2731; Ishida et al., 1995, J. Org. Chem. 60:5374-5375; WO 95/33765, published Jun. 6, 1995; Xue and DeGrado, 1994, J. Org. Chem. 60(4):946-952; Jacquier et al., 1991, In: Peptides 1990 221-222, Giralt and Andreu, Eds., ESCOM Leiden, The Netherlands; Schmidt and Neubert, 1991, In: Peptides 1990 214-215, Giralt and Andreu, Eds., ESCOM Leiden, The Netherlands; Toniolo, 1990, Int. J. Peptide Protein Res. 35:287-300; Ulysse et al., 1995, J. Am. Chem. Soc. 117:8466-8467; Durr et al., 1991, Peptides 1990 216-218, Giralt and Andreu, Eds., ESCOM Leiden, The Netherlands; Lender et al., 1993, Int. J. Peptide Protein Res. 42:509-517; Boger and Yohannes, 1990, J. Org. Chem. 55:6000-6017; Brady et al., 1979, J. Org. Chem. 4(18):3101-3105; Spatola et al., 1986, J. Am. Chem. Soc. 108:825-831; Seidel et al., 1991, In: Peptides 1990 236-237, Giralt and Andreu, Eds., ESCOM Leiden, The Netherlands; Tanizawa et al., 1986, Chem. Phar, Bull. 34(10):4001-4011; Goldenburg & Creighton, 1983, J. Mol. Biol. 165:407-413; WO 92/00995 and WO 94/15958. These methods may be routinely adapted to synthesize the polypeptides described herein and are incorporated into this application by reference.

5.3.3 Recombinant Synthesis of Polypeptides

If the polypeptide described herein is composed entirely of genetically-encoded amino acids, or a portion of it is so composed, the peptide or the relevant portion may also be synthesized using conventional recombinant genetic engineering techniques.

For recombinant production, a polynucleotide sequence encoding the peptide is inserted into an appropriate expression vehicle, i.e., a vector which contains the necessary elements for the transcription and translation of the inserted coding sequence, or in the case of an RNA viral vector, the necessary elements for replication and translation. The expression vehicle is then transfected into a suitable target cell which will express the peptide. Depending on the expression system used, the expressed peptide is then isolated by procedures well-established in the art. Methods for recombinant protein and peptide production are well known in the art (see, e.g., Sambrook et al., 1989, Molecular Cloning A Laboratory Manual, Cold Spring Harbor Laboratory, N.Y.; and Ausubel et al., 1989, Current Protocols in Molecular Biology, Greene Publishing Associates and Wiley Interscience, N.Y. each of which is incorporated by reference herein in its entirety.)

To increase efficiency of production, the polynucleotide can be designed to encode multiple units of the peptide separated by enzymatic cleavage sites; either homopolymers (repeating peptide units) or heteropolymers (different peptides strung together) can be engineered in this way. The resulting polypeptide can be cleaved (e.g., by treatment with the appropriate enzyme) in order to recover the peptide units. This can increase the yield of peptides driven by a single promoter. A polycistronic polynucleotide can be designed so that a single mRNA is transcribed which encodes multiple peptides (i.e., homopolymers or heteropolymers) each coding region operatively linked to a cap-independent translation control sequence; e.g., an internal ribosome entry site (IRES). When used in appropriate viral expression systems, the translation of each peptide encoded by the mRNA is directed internally in the transcript; e.g., by the IRES. Thus, the polycistronic construct directs the transcription of a single, large polycistronic mRNA which, in turn, directs the translation of multiple, individual peptides. This approach eliminates the production and enzymatic processing of polyproteins and may significantly increase yield of peptide driven by a single promoter.

Polynucleotides capable of generating or expressing certain cyclic polypeptides may be prepared in vitro and/or in vivo. Polypeptides may be prepared from polynucleotides to generate or express the cyclic polypeptides utilizing the trans splicing ability of split inteins. Methods for making such polynucleotides to yield cyclic peptides are known in the art and are described, for example, in WO 01/66565, WO 00/36093; U.S. Patent Application No. 60/358,827, entitled "Cyclic Peptides and Analogs Useful to Treat Allergies," the disclosures of which are incorporated herein by reference.

A variety of host-expression vector systems may be utilized to express the polypeptides described herein. These include, but are not limited to, microorganisms such as bacteria transformed with recombinant bacteriophage DNA or plasmid DNA expression vectors containing an appropriate coding sequence; yeast or filamentous fungi transformed with recombinant yeast or fungi expression vectors containing an appropriate coding sequence; insect cell systems infected with recombinant plasmid or virus expression vectors (e.g., baculovirus) containing an appropriate coding sequence; plant cell systems infected with recombinant virus expression vectors (e.g., cauliflower mosaic virus or tobacco mosaic virus) or transformed with recombinant plasmid expression vectors (e.g., Ti plasmid) containing an appropriate coding sequence; animal cell systems. Cell-free in vitro polypeptide synthesis systems may also be utilized to express the polypeptides described herein.

The expression elements of the expression systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage lambda, plac, ptrp, ptac (ptrp-lac hybrid promoter) and the like may be used; when cloning in insect cell systems, promoters such as the baculovirus polyhedron promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5 K promoter) may be used; when generating cell lines that contain multiple copies of expression product, SV40-, BPV- and EBV-based vectors may be used with an appropriate selectable marker.

In cases where plant expression vectors are used, the expression of sequences encoding the polypeptides described herein may be driven by any of a number of promoters. For example, viral promoters such as the 35S RNA and 19S RNA promoters of CaMV (Brisson et al., 1984, Nature 310:511-514), or the coat protein promoter of TMV (Takamatsu et al., 1987, EMBO J. 6:307-311) may be used; alternatively, plant promoters such as the small subunit of RUBISCO (Coruzzi et al., 1984, EMBO J. 3:1671-1680; Broglie et al., 1984, Science 224:838-843) or heat shock promoters, e.g., soybean hsp17.5-E or hsp17.3-B (Gurley et al., 1986, Mol. Cell. Biol. 6:559-565) may be used. These constructs can be introduced into plant cells using Ti plasmids, Ri plasmids, plant virus vectors, direct DNA transformation, microinjection, electroporation, etc. For reviews of such techniques see, e.g., Weissbach & Weissbach, 1988, Methods for Plant Molecular Biology, Academic Press, N.Y., Section VIII, pp. 421-463; and Grierson & Corey, 1988, Plant Molecular Biology, 2d Ed., Blackie, London, Ch. 7-9.

In one insect expression system that may be used to produce the polypeptides described herein, *Autographa californica*, nuclear polyhidrosis virus (AcNPV) is used as a vector to express the foreign genes. The virus grows in *Spodoptera frugiperda* cells. A coding sequence may be cloned into non-essential regions (for example the polyhedron gene) of the virus and placed under control of an AcNPV promoter (for example, the polyhedron promoter). Successful insertion of a coding sequence will result in inactivation of the polyhedron gene and production of non-occluded recombinant virus (i.e., virus lacking the proteinaceous coat coded for by the polyhedron gene). These recombinant viruses are then used to infect *Spodoptera frugiperda* cells in which the inserted gene is expressed (e.g., see Smith et al., 1983, J. Virol. 46:584; U.S. Pat. No. 4,215,051). Further examples of this expression system may be found in Current Protocols in Molecular Biology, Vol. 2, Ausubel et al., eds., Greene Publish. Assoc. & Wiley Interscience.

In mammalian host cells, a number of viral based expression systems may be utilized. In cases where an adenovirus is used as an expression vector, a coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing peptide in infected hosts. (e.g., see Logan & Shenk, 1984, Proc. Natl. Acad. Sci. USA 81:3655-3659). Alternatively, the vaccinia 7.5 K promoter may be used, (see, e.g., Mackett et al., 1982, Proc. Natl. Acad. Sci. USA 79:7415-7419; Mackett et al., 1984, J. Virol. 49:857-864; Panicali et al., 1982, Proc. Natl. Acad. Sci. USA 79:4927-4931).

In cell-free polypeptide production systems, components from cellular expression systems are obtained through lysis of cells (eukarya, eubacteria or archaea) and extraction of important transcription, translation and energy-generating components, and/or, addition of recombinant synthesized constituents (e.g., see Shimizu et al. Methods. 2005 July; 36(3):299-304; Swartz et al. 2004. Methods in Molecular Biology 267:169-182). Thus, cell-free systems can be composed of any combination of extracted or synthesized components to which polynucleotides can be added for transcription and/or translation into polypeptides.

Other expression systems for producing polypeptides described herein will be apparent to those having skill in the art.

The polypeptides described herein can be purified by art-known techniques such as reverse phase chromatography high performance liquid chromatography, ion exchange chromatography, gel electrophoresis, affinity chromatography and the like. The actual conditions used to purify a particular compound will depend, in part, on synthesis strategy and on factors such as net charge, hydrophobicity, hydrophilicity, etc., and will be apparent to those having skill in the art.

5.3.4 Arrays

A plurality can be an ordered or unordered array of polypeptides, recombinant host cells, or wells or vessels serving as reaction chambers. Using such an addressable technology enables the determination of the nature and location of the library constituents during screening. A combinatorial complex carbohydrate library comprising a plurality of addressable complex carbohydrate structures is taught in U.S. Pat. No. 6,994,966. A method for conducting chemical or biochemical reactions on a substrate surface in which the reactions take place in an enclosed chamber between components of a fluid and molecular moieties present on an interior surface of the chamber is provided in U.S. Pat. No. 7,045,287. In U.S. Pat. No. 6,917,882, a method for "in silico" nucleic acid recombination methods, related integrated systems utilizing genetic operators and libraries made by in silico shuffling methods is disclosed. U.S. Pat. Nos. 6,811,969 and 6,579,719 provide methods of retentate chromatography for resolving analytes in a sample. Specific examples of methods for synthesizing a plurality of proteins or oligonucleotides in parallel are found in U.S. Pat. Nos. 5,643,738; 5,681,484; and 5,585,069.

"Surface," "Support," "Solid Support," "Solid Substrate," "Solid Carrier," or "Resin" are interchangeable terms and refer to any solid phase material. Surface also encompasses terms such as "solid phase" and/or "membrane." A surface or solid support can be composed of organic polymers such as polystyrene, polyethylene, polypropylene, polyfluoroethylene, polyethyleneoxy, and polyacrylamide, as well as co-polymers and grafts thereof. A solid support can also be inorganic, such as glass, silica, controlled pore glass (CPG), reverse phase silica or metal, such as gold or platinum. The configuration of a substrate can be in the form of beads, spheres, particles, granules, a gel, a membrane or a surface. Surfaces can be planar, substantially planar, or non-planar. Solid supports can be porous or non-porous, and can have swelling or non-swelling characteristics. A solid support can be configured in the form of a well, depression, or other container, vessel, feature, or location. A plurality of supports can be configured on an array at various locations, addressable for robotic delivery of reagents, or by detection methods and/or instruments.

Variants in the arrays can be in the form of lyophilized powders, clarified or crude lysates, immobilized enzymes, colonies of microorganisms, isolated proteins or recombinant DNA expression vectors.

Variants can be pooled and/or combined with additional enzymes or cofactors to enable coupled enzyme reactions.

5.3.5 Methods of Screening

"Detect" and "detection" have their standard meaning, and are intended to encompass detection, measurement and/or characterization of a selected enzyme or enzyme activity. For example, enzyme activity may be "detected" in the course of detecting, screening for, or characterizing candidate or unknown ligands, as well as inhibitors, activators, and modulators of enzyme activity.

"Spectrally Resolvable" means, in reference to a set of fluorescent dyes, that the fluorescence emission bands of the respective dyes are sufficiently distinct, i.e., sufficiently non-overlapping, that the dyes, either alone or when conjugated to other molecules or substances, are distinguishable from one another on the basis of their fluorescence signals using standard photodetection systems such as photodetectors employing a series of band pass filters and photomultiplier tubes, charged-coupled devices (CCD), spectrographs, etc., as exemplified by the systems described in U.S. Pat. Nos. 4,230,558 and 4,811,218 or in Wheeless et al., 1985, Flow Cytometry: Instrumentation and Data Analysis, pp. 21-76, Academic Press, New York. All of the dyes comprising a spectrally resolvable set of dyes may be excitable by a single light source, or may be excitable by multiple light sources.

"Mass spectrometry" encompasses any suitable mass spectrometric format known to those of skill in the art. Such formats include, but are not limited to, Matrix-Assisted Laser Desorption/Ionization, Time-of-Flight (MALDI-TOF), Electrospray (ES), IR-MALDI (see, e.g., PCT Application No. WO 99/57318 and U.S. Pat. No. 5,118,937) Ion Cyclotron Resonance (ICR), Fourier Transform and combinations thereof.

"Detectable label" refers to a moiety that, when attached to a moiety described herein, e.g., a polypeptide, renders such a moiety detectable using known detection methods, e.g., spectroscopic, photochemical, electrochemiluminescent, and electrophoretic methods. Exemplary labels include, but are not limited to, fluorophores and radioisotopes. Such labels allow direct detection of labeled compounds by a suitable detector, e.g., a fluorometer.

For such embodiments, the label may be a direct label, i.e., a label that itself is detectable or produces a detectable signal, or it may be an indirect label, i.e., a label that is detectable or produces a detectable signal in the presence of another compound. The method of detection will depend upon the labeled used, and will be apparent to those of skill in the art. Examples of suitable direct labels include radiolabels, fluorophores, chromophores, chelating agents, particles, chemiluminescent agents and the like.

Radioactive labels: Suitable radiolabels include, by way of example and not limitation, $^3H$, $^{14}C$, $^{32}P$, $^{35}S$, $^{36}Cl$, $^{57}CO$, $^{131}I$ and $^{186}Re$.

"Chromophore" refers to a moiety with absorption characteristics, i.e., are capable of excitation upon irradiation by any of a variety of photonic sources. Chromophores can be fluorescing or nonfluorescing, and includes, among others, dyes, fluorophores, luminescent, chemiluminescent, and electrochemiluminescent molecules.

Examples of suitable indirect labels include enzymes capable of reacting with or interacting with a substrate to produce a detectable signal (such as those used in ELISA and EMIT immunoassays), ligands capable of binding a labeled moiety, and the like. Suitable enzymes useful as indirect labels include, by way of example and not limitation, alkaline phosphatase, horseradish peroxidase, lysozyme, glucose-6-phosphate dehydrogenase, lactate dehydrogenase and urease. The use of these enzymes in ELISA and EMITimmunoassays is described in detail in Engvall, 1980, *Methods Enzym.* 70: 419-439 and U.S. Pat. No. 4,857,453.

"Capture tag" refers to a member of a binding pair that, when attached to another molecule herein, e.g., a polynucleotide, can be isolated (i.e., captured) by interaction with the other member of the binding pair. A capture tag may have one or more than one tag, including different types of capture tags. The polypeptides described herein can have one or more of the same or different tags. Exemplary capture tags include biotin, which can be incorporated into nucleic acids (Langer et al., 1981, *Proc Natl Acad Sci USA* 78:6633) and captured using streptavidin or biotin-specific antibodies; a hapten such as digoxigenin or dinitrophenol (Kerkhof, 1992, *Anal Biochem* 205:359-364), which can be captured using a corresponding antibody; and a fluorophore to which antibodies can be generated (e.g., Lucifer yellow, fluorescein, etc.). A capture tag can comprise a specific sequence, referred to as a "capture sequence," which can be captured using a "capture probe" having a sequence complementary to the capture sequence. A capture tag can comprise a peptide sequence that interacts with corresponding antibodies. Exemplary peptide tags include, among others, FLAG tag, c-myc tag, polyarginine tag, poly-His, HAT tag, calmodulin binding peptide, and S-fragment of RNase A (see, e.g., Terpe, K, 2003, *Appl Microbiol Biotechnol* 60:523-533). Other tags for use in labeling the polynucleotides described herein will be apparent to the skilled artisan.

Screening may be performed under a range of temperature, pH, and or solvent conditions.

5.3.6 Methods of Selecting an Optimized, Diverse Population of Polypeptide Variants In some embodiments, it is desirable to start with a diverse population of polypeptide variants optimized for various properties to increase the likelihood of identifying one or more polypeptides having the desired property. This can be useful, for instance where the property is a novel activity not observed with the corresponding naturally occurring polypeptide. Identification of a parent backbone sequence provides a starting point for further evolutions. In view of the foregoing, the present disclosure provides a method using a Pareto front determined for a population of polypeptide variants, and a fitness function to select out variants based on the number of nearest neighbors shared between variants in the Pareto front. By use of a descending Pareto front and nearest neighbor analysis for each variant on the descending Pareto front, variants that are similar to each other can be screened out, thereby resulting in a selected set of optimized, diverse polpeptide variants that can be used as a set for initial screening of a desired (e.g., or novel) property(s).

In some embodiments, the method for selecting a set of optimized, diverse population of variants comprises:

(a) selecting one or more objectives for optimization of a plurality of molecular variants, wherein each molecular variant in the plurality is described by two or more objective data;

(b) determining a first Pareto front membership for each of the plurality of molecule variants based on the objectives of optimization;

(c) setting optimization parameters, wherein the optimization parameters comprise:
  (i) number nvar of molecular variants to select;
  (ii) a molecular variant population size popSize;
  (iii) a crossover rate;
  (iv) a mutation rate;
  (v) a fitness function comprising a penalty fitness function and an overall fitness function, wherein the penalty fitness function is based on niche counting and the overall fitness function is based on location in a descending Pareto front divided by the number of shared number of molecular variants within each front; and
  (v) molecular variants to be included in the nvar of molecular variants; and (d) identifying a search space of acceptable variants;

(e) generating a random population of genomes from the search space of acceptable variants using a selection operator; and (f) selecting a first set of nvar variants by applying a crossover operator, a mutation operator, a repair operator, and a fitness operator to the random population of genomes. A flow diagram of the method is shown in FIG. 8

For each variant in the library or variant population, there is an associated objective data of properties, as described above. The objective data can include sequence information, which can be characterized in character strings, and/or other properties of the variant, such as activity data. Activity data may be obtained by assays or screens appropriately designed to measure activity, as discussed herein.

Once the objective data for the plurality of molecular variants are determined and inputted, a first Pareto front membership for each of the plurality of molecule variants is calculated based on the selected objectives of optimization. Generally, Pareto front optimization is a multi-objective evolutionary algorithm that simultaneously improves two or more desired objectives. The Pareto front is occupied by variants that are non-dominated by other molecular variants in at least one of two or more desired objectives. In other words, the solutions, typically represented by the numbered data points, that lie on the Pareto front represent trade-off solutions that are not "dominated" by any other solution. These non-dominated points are defined by the fact that no other solution exists in the hypothetical data set that is better than all solutions in both objectives. FIG. 9 shows a example of a Pareto front determined for a set of related enone reductase (ERED) enzymes having different values for their fold improvement in activity versus a positive control for two substrates (Dione and Phenyl Methacrylate). The Pareto front can be established by any number of ways known in the art. See US application publication Nos. 20040072245; 20060195204; 20060205003 and 20070208677. Other applications of Pareto fronts for purposes of multiobjective optimization are described in WO 02/075650; Shukla and Deb, 2007, *European Journal of Operational Research* 181(3): 1017-1724; and Elaoud and Loukil, 2007, *European Journal of Operational Research* 177(1):1703-1719; all references incorporated herein by reference.

A set of optimization parameters is defined, where the parameters comprise:
  (i) the number of variants nvar to be selected;
  (ii) a molecular variant population size popSize;
  (iii) a crossover rate;
  (iv) a mutation rate;
  (v) an fitness function; and
  (vi) molecular variants to be automatically included in the solution set nvar.

The number of molecular variants to be created, nvar, is a finite number defined by the user, and constrains the size of the final solution. The value can be set based on any number of criteria, such as the number of variants that can be efficiently screened for the various properties of the molecular variants. For example, a straightforward nvar can correspond to the number of samples in a selected number of 96 well plates that can be initially screened efficiently.

The population size popSize is simply the initial starting population of random genomes (e.g., number of molecular variants) chosen for processing for fitness and other operations.

The crossover rate is the probability of crossover between two members in the variant population and is applied by a crossover operator. A crossover operator generally pairs members of the population, and the different parts of a "gene" cross combined, resulting in a pair of offsprings, i.e., new pair of solutions. In the context of the present disclosure, the crossover rate is based on the [0,1] scale and refers to the absence or presence of the variant molecule in the population set, whether prior to or after application of any fitness operator.

The mutation rate is applied to a population by a mutation operator, and acts to create, with some defined probability, a change in the character strings of the "gene" (e.g., polypeptide) and functions to maintain diversity within the population.

The fitness function assesses the fitness of a particular variant and comprises a penalty fitness function and an overall fitness function. The penalty fitness function takes into account the number of nearest neighbors, and is based on the reasoning that variants similar to each other are less likely to show different behaviors or novel properties. Although variants could be scored solely based on membership within each Pareto front, and selected based on its isolation in the Pareto front, this type of selection is more useful for selecting a variant for further optimization of a defined property, as opposed to identification of a set of optimized, maximally diverse variants. As such, variants on the Pareto front are selected for fitness by penalizing variants which are similar to each other. The penalty fitness function can be determined using the concept of niche counting the number of nearest neighbor molecular variants. Generally, niche counting consists of formulating a distance metric in an n-dimensional space, where n is the number of objectives, and using the distance to define a local hypervolume and counting the number of nearest neighbor variants occupying the hypervolume. A nearest neighbor variant located further from a variant occupies a smaller fraction of the hypervolume space with respect to that variant. Solutions that contain variants with a higher number of nearest neighbors, i.e., large number of variants occupying the hypervolume space, are less fit solutions. Because the number nvar is finite, the algorithm tends to select one variant from the crowded of similar variants. The details of formulating the distance metric and niching are described in Deb, K., 1999, "Multiobjective genetic algorithms: problem difficulties and construction of test problems," *Evolutionary Computation* 7:205-230; incorporated herein by reference. Other niche techniques are described in Darwen et al., 1997, "Speciation as automatic categorical modularization," *IEEE Transactions on Evolutionary Computation* 1(2):101-108; Darwen et al., 1996, "Every niching method has its niche: fitness sharing and implicit sharing compared," *Proc. of Parallel Problem Solving from Nature* (PPSN) IV, Vol. 1141, Lecture Notes in Computer Science, pp. 398-407, Springer-Verlag; and Horn et al., 1994, "A niched pareto genetic algorithm for multiobjective optimization," In *Proceedings of the First IEEE Conference on Evolutionary Computation*, IEEE World Congress on Computational Computation, 1:82-87; all publications incorporated herein by reference.

A second aspect of the fitness function is the overall fitness function, which in the present disclosure can consist of assigning variants to descending Pareto fronts and dividing those fitnesses by the number of shared neighbors, as determined by the distance metric and niche count. Ever descending Pareto fronts represent lower fitness levels (e.g., less optimal). The overall fitness function can be used to drive the optimization to select the best subset of variants from the plurality of variants.

The variants to be automatically included in the solution nvar can comprise particular sets of molecular variants known to have predetermined characteristics useful for the objectives, such as expanded substrate specificity. There can also be zero variants to be included in the solution set.

Although the optimization parameters are described for genetic algorithms, it is to be understood that other strategies may be used, including, among others, tabu search, simulated annealing, etc.

To identify a search space for selecting a set of optimized diverse variants, descending Pareto fronts are used to identify variants less fit than those in the initial Pareto front but which can provide diversity for the selected size nvar. From this superset of variants, an initial random population of genomes of size popSize is generated by a selection operator. The genomes represent the solution set of molecular variants from which the set of optimized, diverse molecular variants are chosen.

To select a set of optimized diverse molecular variants from the initial population popSize, the random plurality of genomes is subjected to selection based on genetic operators that include crossover operator, mutation operator, fitness operator, and repair operator. These operators act to apply the corresponding optimization parameters discussed above to the random plurality of genomes. In the present disclosure, the repair operator is used to place constraints on the selection by limiting the size of the progeny genome to a user defined finite number nvar. If the progeny genome size is less than nvar, the repair operator enforces the constraint by turning bits on to generate additional molecular variants to satisfy nvar. If the progeny population greater than nvar, the repair operator enforces the constraint by turning bits off to reduce the number of molecular variants to satisfy nvar.

The set of molecular variants resulting from application of the optimization parameters and corresponding operators is evaluated for the desired properties as well as diversity. For purposes of illustration, a set of resulting polypeptide variants can be generated by recombinant techniques, and each variant expressed in an appropriate expression system, either in vitro or in vivo. The synthesized polypeptides are evaluated for the desired properties, such as activity, stability and other profiles. If it is desirable to obtain additional optimized, diverse sets of molecular variants, the process of applying the optimization parameters can be reiterated to generate a second set of nvar. As such, the nvar number of variants can be combined with all the candidates from the original superset in order to create a single subset nvar. In this way, the overall diversity comparing all variants against each other will be maximized. Continued reiteration for a number of generations nGen allows evaluation of a number of different solutions sets of molecular variants for further evaluation, in silico or in the laboratory.

The method herein can be used alone or in conjunction with other methods, such as methods of creating an optimized diverse population of molecules. In other words, an initial optimized diverse set of variant polypeptides could be generated and tested using the methods described herein, and based on the initial sets of identified mutations, additional polypeptide variants created to further evolve other variants to screen for the desired properties. Methods for creating additional variants in silico for screening are described in the following section. Other methods for generating polypeptide variants are described in US application publications 20040072245, 20060195204, 20060205003, and 20070208677, all of which are incorporated herein by reference.

The method can also be implement in the form of a computer software, and/or as an internet based client-server system, where the client can provide user defined parameters, such as the initial population of variants, the objective data set representing the various properties of a polypeptide, and user definable optimization parameters, The server can provide the hardware and software for carrying out one or more steps described above, such as calculation of the initial Pareto front and the application of fitness operators.

5.3.7 Methods of Creating and Optimized Diverse Set of Polypeptide Variants

After identification of polypeptides with the desired activities and their corresponding mutations, it is also desirable to use the information gleaned from the mutations to generate additional variants that can be evolved and screened to optimize the desired properties of the polypeptides. In this process, limiting the number of variants to be screened provides for efficiency while diversity can enhance the probability of identifying a set of variants having the additional desired properties (e.g., robustness of activity). Thus, the present disclosure also provides a method of creating an optimized, diverse set of polypeptide variants from a defined set of mutations. The approach herein employs multi-objective optimization procedures, particularly the subfield devoted to evolutionary algorithms (Deb, K., 1999, Multi-objective genetic algorithms: problem difficulties and construction of test problems," *Evolutionary computation* 7, 205-230; incorporated herein by reference). The goal of the methods herein is to create a set of variants that are optimized and maximally diverse. Similar approaches of multi-objective optimization have been shown to work successfully in fields such as software testing, where antirandom tests are written to be as maximally different from each other as possible (Malaiya, Y. K., 1995, Antirandom testing: getting the most out of blackbox testing. Proceedings of the International Symposium on Software Reliability Engineering, ISSRE). Additional preferences to target the frequency of specific mutations believed to confer properties of interest (e.g., a penalty function) can be included in the algorithm.

Generally, the method for creating an optimized, maximally diverse library of molecular variants comprises the steps of:
 (a) inputting a desired set of mutations;
 (b) setting optimization parameters, wherein the optimization parameters comprise:
  (i) number nvar of bio-molecule variants to create;
  (ii) molecular variant population size popSize;
  (iii) crossover probability crossrate;
  (iv) mutation rate mutrate;

(v) repair operator,
(vi) primary fitness function;
(vii) penalty fitness function; and
(c) generating a random plurality of genomes of the population size popSize;
(d) creating a first generation of genomes of the size nvar by applying a selection operator, a crossover operator, a mutation operator, a repair operator, a primary fitness operator, and penalty function operator on the plurality of random genomes.

The first generation of genomes, also referred to a progeny genome, can be evaluated for the desired level of diversity and optimization. In some embodiments, the method comprises repeating step (d) for the first generation of genomes to generate a second generation of genomes for purposes of additional diversity and optimization. Reiterative use of step (d) for a number of generations nGen can be used to create additional genome subsets. A flow diagram of the method is illustrated in FIG. 10.

The molecules for performing the method can be any molecule where variations can be defined as an descriptor or objective data set, such as a character string. These include polynucleotides or polypeptides.

When applied to polypeptides, the desired set of mutations can be chosen for any number of criteria, including but not limited to, frequency of occurrence in a data set, association of the mutation with a particular polypeptide property, and occurrence in a particular region of the polypeptide (for example, a substrate binding pocket). In some embodiments, mutations are associated with changes in one or more polypeptide properties, such as enzyme activity, stereospecificity, stereoselectivity, thermal stability, solvent stability, inhibitor resistance, can all be inputted as a data set.

Once a data set of mutations is created, a set of optimization parameters is defined, which parameters will operate on the mutation data set for generating a new set of molecular variants having maximal information content, e.g., optimized properties and maximal diversity. The parameters for optimization are as follows, and follows those described above in the preceding section.

The first parameter is the number of molecular variants to be created, nvar. This, as discussed above, is a finite number set by the user, and constrains the size of the final solution. The value can be set based on any number of criteria, such as the number that can be efficiently screened for the various properties of the molecular variants.

The second parameter is the population size popSize, which is simply the initial starting population of random genomes (e.g., combinations number of mutation sets) chosen for processing for fitness and other operations.

The third parameter is the crossover probability rate, which is applied to the population by a crossover operator. A crossover operator generally pairs members of the population, and the different parts of the "gene" cross-combined, resulting in a pair of offspring, i.e., new pair of possible solutions. A variety of crossover operators that have been developed in the field of genetic algorithms can be used, such as, for example, one point, multipoint, uniform, and arithmetic, each offering different performance (in terms of convergence, or the exploration/exploitation tradeoff) under different conditions, and the probability. In some embodiments, the crossover event can be set at a fixed rate.

The fourth parameter is the mutation rate mutrate, which is applied to the population by a mutation operator. The mutation operator acts on the member of the population to create, with some defined probability, a change in the character strings of the "gene" (e.g., polypeptide) and acts to maintain diversity within the populations. The crossover rate and mutation are used to mate and breed genomes for creating the progeny genome.

The fifth parameter is the fitness function, which comprises at least a primary fitness function, and optionally a penalty fitness function. The primary fitness is used as part of a selection process to generate a genome subset from a population popSize by selecting out molecular variants that are similar to each other. Variants which are similar to each other are hypothesized to be less likely to display different properties. In some embodiments, in order to penalize the fitness of variants which are similar to each other, niche counting can be used for determining the primary fitness, as described above. Niche counting can comprise formulating a distance metric in an n-dimensional space (where n is the number of positions being mutated). This distance metric, which is essentially the Euclidean distance generalized to n-dimensions, can then be used to define a local hypervolume where the number of nearest neighbors in that space can be counted. Those variants with many neighbors are considered less fit variants as they tend to occupy nearby regions of sequence-function space. The details of formulating the distance metric and niching are described by Deb, supra. The primary fitness function for a candidate solution (set of variants to create) is calculated by summing the inverse of the number of nearby neighbors for every variant in proposed set. Other niche techniques are described in the references cited above.

It is to be understood that other types of primary fitness functions can be applied to maximize the diversity of the progeny genome. In some embodiments, the fitness function can be based on D-optimality, A-optimality or other information-based criteria that can be used to construct a matrix of variants containing the maximum information content for an objective data set. As is known in the art, D-optimal designs are straight optimizations based on a chosen optimality criterion and the model that will be fit. The optimality criterion used in generating D-optimal designs is one of maximizing $|X'X|$, the determinant of the information matrix $X'X$. A-optimality is based on the sum of the variances of the estimated parameters for the model, which is the same as the sum of the diagonal elements, or trace, of $(X'X)^{-1}$. Descriptions and applications of D-optimality and A-optimality can be found in Atkinson and Donev, 1992, *Optimal Experimental Designs*, Oxford University Press; Silvey, 1990, *Optimal Design*, Chapman and Hall; Pukelsheim, 1995, *Optimal Design of Experiments*, Chapman and Hall; all publications incorporated herein by reference.

In addition to the primary fitness function, in some embodiments, additional fitness penalties can be ascribed by the user to target other parameters, such as the average number of mutations per variant and/or the frequency a given mutation should be seen within the set of variants. These additional penalties can be weighted with higher or lower penalty weights, allowing the user to drive the solution set in preferred directions. For example, the average number of mutations can be restricted to a lower average number of mutations if a higher average number of mutations lead to a significant proportion of the progeny genome being non-active molecules. Similarly, weights given to the frequency of a particular mutation can be adjusted, for example, if a particular mutation adds to the thermal stability of a polypeptide variant independent of other mutations or if a particular amino acid residue is critical to the binding of a ligand and is conserved or invariant when compared to other members of the enzyme family. Other strategies such as tabu search, simulated annealing, etc can be used in place of genetic algorithms.

Upon setting of the optimization parameters, a random plurality of genomes of population size popSize is generated, generally, by a selection operator. This involves picking at random a mutation set and pairing with another mutation set. To create a new population set from the popSize, i.e., the first generation of genomes or the progeny genomes, the random plurality of genomes is subjected to selection based on genetic operators that include crossover operator, mutation operator, primary fitness operator, and when present, the penalty fitness operator. These operators function to apply the optimization parameters described above to the random population of genomes. In the present disclosure, the method applies a repair operator, discussed above, to place constraints on the selection by limiting the size of the progeny genome to a user defined finite number nvar.

The progeny genome resulting from application of the optimization parameters and corresponding operators is evaluated for the desired properties as well as diversity. For purposes of illustration, a progeny genome of polypeptides can be generated by recombinant techniques, and each variant expressed in a appropriate expression system, either in vitro or in vivo. The synthesized polypeptides are evaluated for the desired properties, such as activity, stability and other profiles. If it is desirable to obtain additional optimization and diversification, the process of creating progeny genomes can be reiterated to generate a second generation of genomes. Continued reiteration for a number of generations nGen allows evaluation of a number of different solutions sets for optimization and diversity of properties.

6. EXAMPLES

Aspects of the present disclosure may be further understood in light of the following examples, which should not be construed as limiting the scope of the present disclosure in any way.

Example 1

Construction of a Plurality of Genetically Divergent, Functionally Diverse Polypeptides for Identifying Sequence-Activity Relationships This Example illustrates the generation of a plurality of robust polypeptides (in this case, enzymes), each of which reacts with a substrate to produce a product, and wherein at least two members of the plurality react with different substrates or react with differing levels of activity upon a given substrate. In some embodiments, the composition and methods described herein include a plurality of polypeptides, each of which reacts with a substrate to produce a product, and wherein at least two members of the plurality react with differing levels of activity upon a given substrate. In some embodiments, the composition and methods described herein include a plurality of polypeptides, each of which reacts with a substrate to produce a product, and wherein at least two members of the plurality react with different substrates.

(a) Identification of an Ancestral Enzyme:

One means of accelerating the identification and development of polypeptides having a desired activity, is to use information about previously-described microbes and/or enzymes catalyzing a reaction of choice for the selection of a starting (ancestral) polypeptide for design of evolved parent polypeptides which can be used to populate a pre-tuned plurality. An ancestral enzyme is used in the methods described herein as the basis for generating a plurality of polypeptide variants, which can then be screened for various desired activities on different substrates. In some embodiments, the polypeptide variants are used to populate a plurality which is screened for one or more desired activities. A suitable ancestral enzyme for development into a robust plurality of polypeptide variants is chosen based on the available information on enzymes that catalyze the type of reaction of interest, e.g. ketoreductases for reduction of ketones to chiral alcohols. Examples of sources of such information include, but are not limited to: previous experience with such enzymes; wild-type enzymes described in the literature; polypeptide variants described in the literature that incorporate one or more mutations previously demonstrated to affect activity, substrate specificity, selectivity or stability; structural modeling; and substrate binding and docking studies. One example of a suitable ancestral polypeptide includes, but is not limited to, an enzyme having a malleable substrate binding pocket (tolerant of mutations while retaining activity). Another example of a suitable ancestral polypeptide is an enzyme that is a member of a family of homologous enzymes with demonstrated functional diversity on different substrates.

Figure 1:
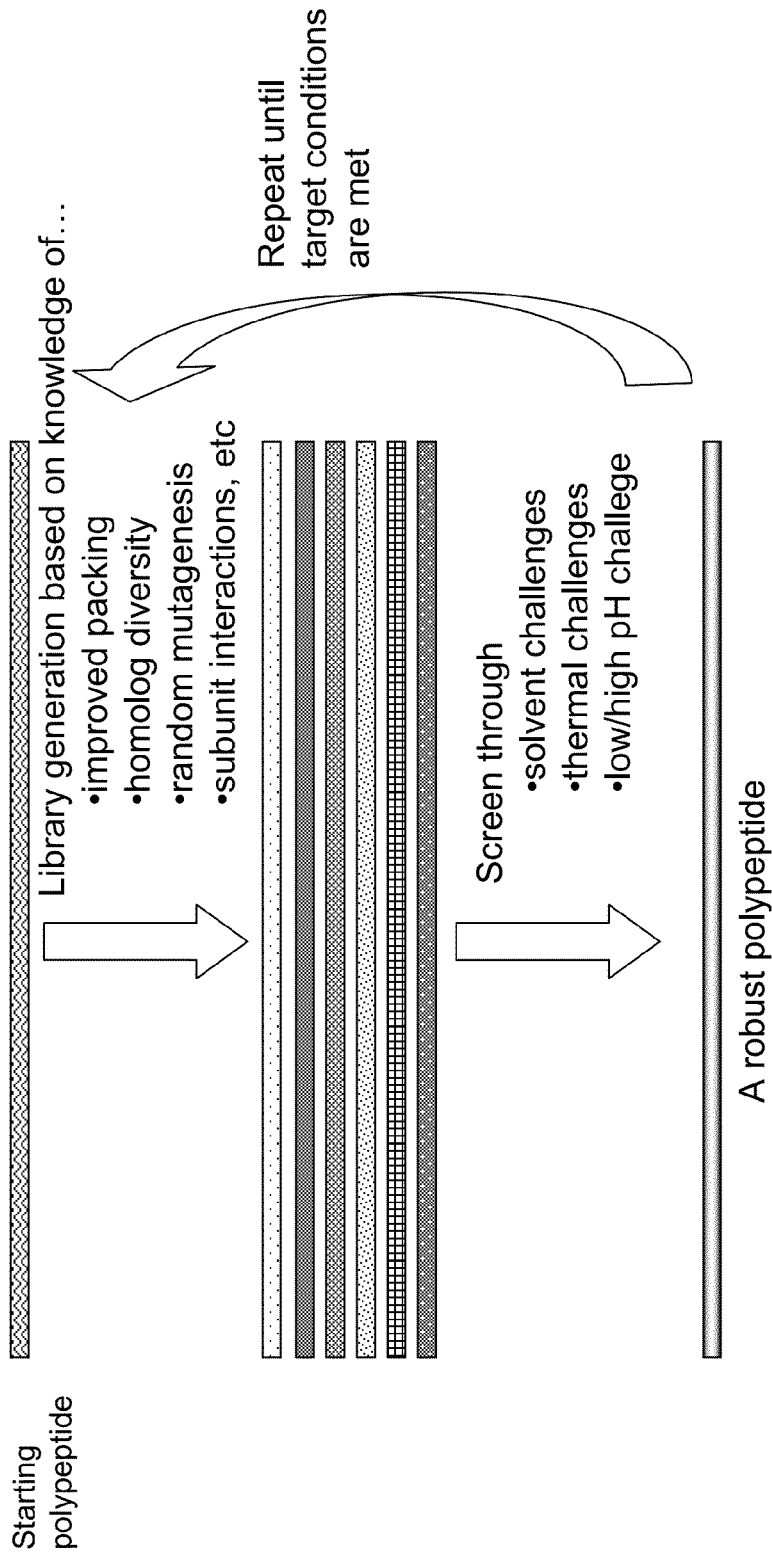
FIG. 1 illustrates a scheme for evolving polypeptide variants from an ancestral or parent starting enzyme.

(b) Identification of a Robust and Scaleable Parent Enzyme:

In some embodiments, the ancestral enzyme is not sufficiently robust to operate under desirable process conditions. In such instances, protein engineering, for example by directed evolution, can be used to obtain one or more variants of the ancestral enzyme having improved robustness to physical process conditions such as solvent (nature and concentration), temperature, and pH (as reviewed in M. Lehmann and M. Wyss, *Current Opinion in Biotechnology* 2001, 12:371-375; J. K. Song and J. S. Rhee, *Biochim Biophys Acta* 2001, 1547(2):370-8; and illustrated in FIG. 1). As one example, in the enzymatic reduction of ketones, isopropylalcohol can be used as reductant and is converted to acetone. Tolerance of the enzyme to both isopropylalcohol and acetone can be engineered in the enzyme to bolster its tolerance to chemical process conditions. In some embodiments, a protein engineering program may utilize computational analyses to identify mutations of amino acid residues that are likely to improve stability via enhanced packing of interior residues of a protein, or optimization of subunit interactions. Protein engineering can be used to generate a parent enzyme that is robust, or tolerant, to challenges of high or low temperatures, high or low pH, high levels of substrate and/or product, and/or high concentration of salt or organic solvent.

In some embodiments, a recombinant DNA vector encoding an ancestral polypeptide may exhibit low levels of expression. In such instances, the gene encoding the ancestral polypeptide can be subjected to directed evolution or protein engineering techniques to generate variants which may then be screened to identify variants with enhanced expression, suitable to serve as a parent gene and polypeptide used as the basis for generating polypeptide variants to be screened for a desired activity. In some embodiments, the ancestral polypeptide has been determined to be expressed at high levels. In some embodiments, the ancestral gene and its encoded polypeptide may be highly expressed and robust to function under process conditions, and can be used as a parent polypeptide, serving as the basis for generating polypeptide variants to be screened for a desired activity. In some embodiments, the wild type or ancestral polypeptide is engineered to generate an evolved parent polypeptide that is more robust to pH, temperature and/or solvents than is the wildtype or ancestral polypeptide. In some embodiments, the parent polypeptide has been engineered to be expressed at high levels. In some embodiments, the parent polypeptide is easily manufacturable for large scale production. In some embodiments, the parent polypeptide has been engineered to be easily manufacturable for large scale production.

(c) Generation of Binding Pocket Diversity:

In some embodiments, a plurality of enzyme variants derived from a suitable parent enzyme (as described in (b)) is generated by diversification of amino acids that comprise the substrate binding pocket. Examples of methods used to generate mutations in polypeptides include, but are not limited to: semi-synthetic shuffling using diversity from homologs; gene synthesis; site-directed mutagenesis of recombinant DNA; chemical synthesis of peptide fragments; saturation mutagenesis of the binding pocket; semi-synthetic combinatorial libraries of residues within the binding pocket; error prone PCR; gene shuffling; directed evolution; and recursive sequence recombination (RSR) (see US Patent Application No. 2006/0223143, for example).

In some embodiments, one or more mutations may be included in a polypeptide (e.g., enzyme) variant as compared to the wild type or ancestral polypeptide (e.g., enzyme) such that the mutations generate binding pocket diversity, as illustrated in FIG. 2. Without being bound by theory, polypeptide variants may be generated by making single or multiple amino acid substitutions, additions or deletions at positions known or predicted to comprise the binding pocket, that have been previously reported in the literature to result in a variant that retains activity, or that have been identified or predicted to influence substrate specificity.

Figure 3:
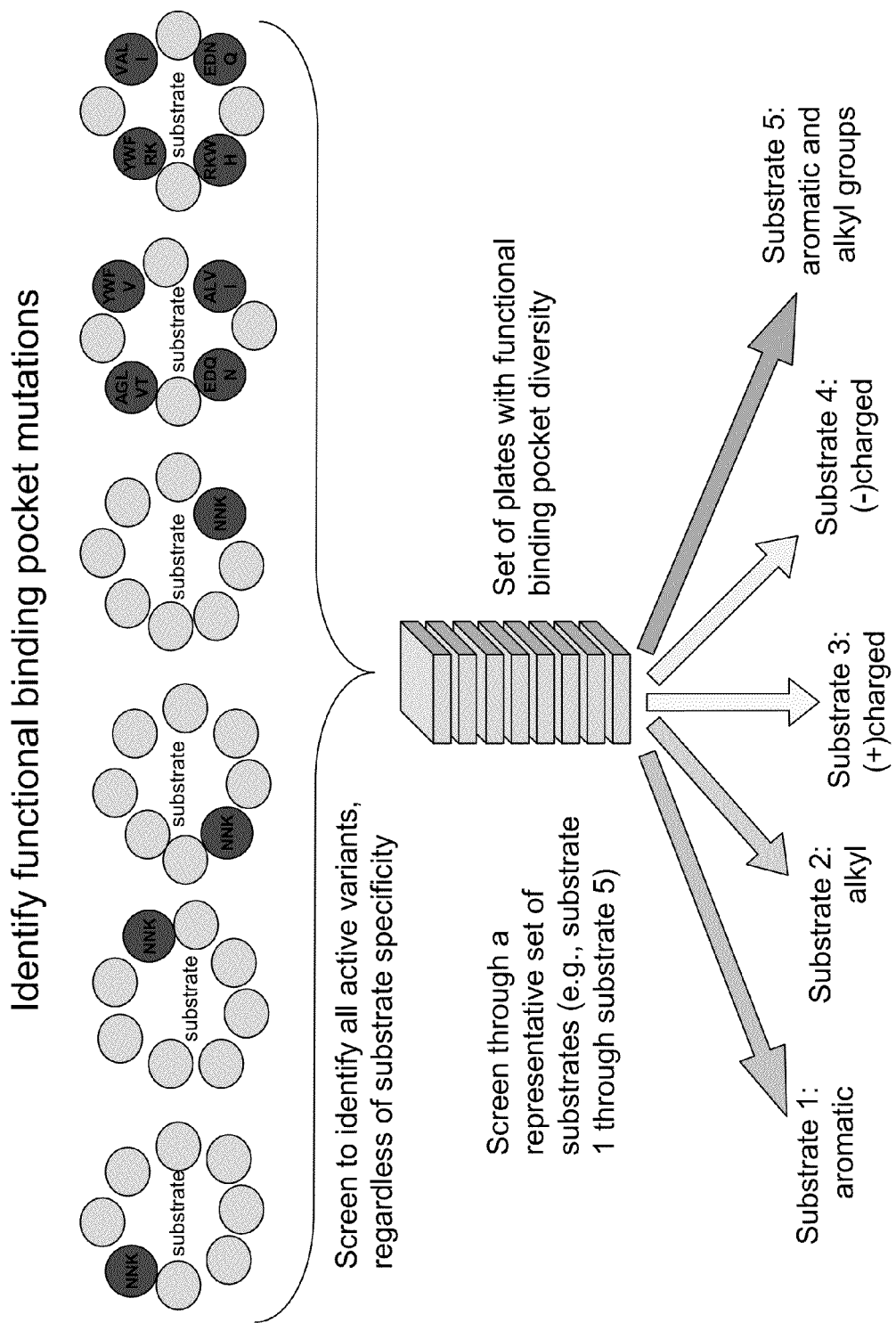
FIG. 3 illustrates a scheme for generating and screening a plurality of polypeptide variants and selection of active variants able to react with different substrates.

One or more substrates may be used to determine if the polypeptides so diversified and representing individual binding pocket variants are viable, functional enzymes. Polypeptide variants with binding pocket diversity exhibiting activity (e.g., functioning enzymes) may be consolidated into a plurality which can then be screened with multiple substrates for the class of enzyme, e.g. different ketones can be used as substrates to screen a plurality of ketoreductase variants. The screening and identification of functional, diversified binding pocket variants is illustrated in FIG. 3.

(d) Generating Sequence-Activity Relationships:

The activity characteristics of enzyme variants within a plurality representing functional binding pocket diversity, as described under (c) are determined using a selection of different substrates for the class of enzyme to screen the plurality. For example, in some embodiments, ketones having alkyl, aryl or heterocyclic substituents to the carbonyl carbon are used to screen the plurality. In some embodiments, ketones having 0, 1 or 2 substituents to the carbonyl carbon are used to screen the plurality. In some embodiments, the substituents are bulky. Activity characteristics that may be determined using different substrates can include, but are not limited to, conversion, stereoselectivities, stereospecificities, regiospecificities, and the like. Such activity data is then used together with the amino acid sequence of the polypeptides to generate sequence-activity relationships for each substrate.

Figure 4:
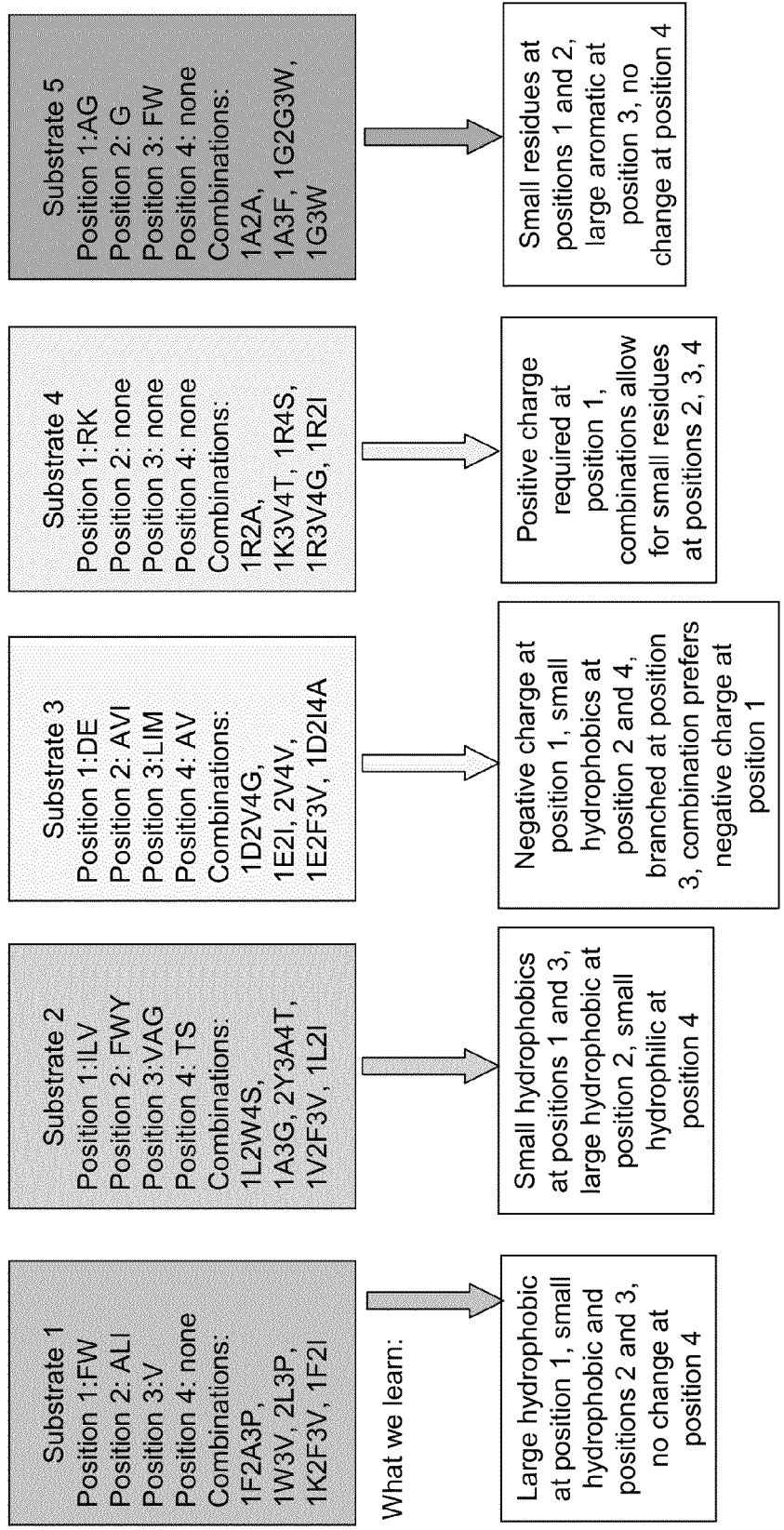
FIG. 4 illustrates an exemplary sequence-activity map relating the various mutations in the binding pocket of several polypeptide variants.

An exemplary sequence-activity map relating to various mutations (as compared to the ancestral or parent enzyme) in the binding pocket of several polypeptide variants is illustrated in FIG. 4. In the example illustrated in FIG. 4, single mutations at position 1 that represent diverse functional activity include amino acids F, W, I, L, V, D, E, R, K, A and G. Single mutations at position 2 that represent diverse functional activity include amino acids A, L, I, F, W, Y, A, V, I and G. Single mutations at position 3 that represent diverse functional activity include amino acids V, A, G, L, I, M, F and W. Single mutations at position 4 that represent diverse functional activity include amino acids T, S, A, and V. Examples of several possible combinations of mutations that also have diverse functional activity may include, but are not limited to combinations such as 1F2A3P, 1W3V, 2L3P, 1K2F3V, 1F2I, 1L2W4S, 1A3G, 2Y3A4T, 1V2F3V, 1L2I, 1D2V4G, 1E2I, 2V4V, 1E2F3V, 1D2I4A, 1R2A, 1K3V4T, 1R4S, 1R3V4G, 1R2I, 1A2A, 1A3F, 1G2G3W, and 1G3W. The combinations that represent diverse functional activity are not limited to combinations of single mutations identified as active in a screen, but can include additional mutations based on structural modeling or computational predictions, for example.

(e) Populate the "Low Resolution" or "Pre-Tuned" Plurality.

The information in the sequence-activity relationship is then used to populate a pre-tuned plurality of enzyme variants. The objective is to optimize the representation of enzymes in the plurality that exhibit both functional (activity/selectivity/specificity) diversity from all substrates tested and the genetic diversity from the binding pocket mutations. Enzyme variants that incorporate the important single and combinatorial mutations identified based on the previously defined sequence-activity relationships (as described in (d)) may be chosen. In some embodiments, the variants of the pre-tuned plurality maintain the same pattern of activity for each substrate as was observed in the larger plurality of single mutations with functional binding pocket diversity. In some embodiments, to reduce the number of members of a plurality, a representative member is selected from a subset of functional variants having single amino acid mutations of a similar character at a particular position (e.g., two variants where either R or K is substituted at a particular position, or two variants where either E or D is substituted at a particular position, or two variants where either V or I is substituted at a particular position, etc.). In some embodiments, one or more computer algorithms is applied to reduce the size of the plurality of the polypeptides for the pre-tuned plurality. For example, a genetic algorithm may be employed with a fitness function that assigns weights to maximize the functional (activity and selectivity on all substrates) and genetic diversity. This algorithm is then used to optimally select a population of enzymes with a wide range of functional and genetic diversity. In some embodiments, a multi-objective optimization algorithm can be used, in which separate dimensions are defined for the activities and selectivities for the various substrates, as well as for genetic diversity. The output of the multi-objective optimization algorithm is then used to help select a diverse set of variants to populate the plurality.

In some embodiments, the number of polypeptide variants in the plurality is reduced by selecting one representative member from a subset of members having very similar activity patterns.

In some embodiments, the plurality comprises representatives of all identified activity patterns and influential mutations.

In some embodiments, the plurality is populated so that each variant is addressable. For example, in some embodiments, the plurality is populated on a multiwell microtiter plate, wherein the address of each well is represented by its coordinates on the plate, such that at least a portion of the amino acid sequence of each variant located at each address is known. In some embodiments, an approximately equal amount of each polypeptide variant is used to populate each well.

Example 2

Use of a Plurality of Genetically Divergent, Functionally Diverse Enzymes for Identification of Enzymes Having Desired Activities on Different Substrates This example illustrates the use of a plurality of robust enzymes, each of which reacts with a substrate to produce a product, and wherein at least two members of the plurality react with different substrates or react with differing levels of activity upon a given substrate. The plurality so-generated is constructed in a manner similar to that described in Example 1, and is used to design, diagnose and identify an enzyme with activity on a substrate not used in establishing the pre-tuned plurality of enzymes. In some embodiments, the plurality is addressable, as described above.

(a) Use of the Pre-Tuned Plurality.

Figure 5:
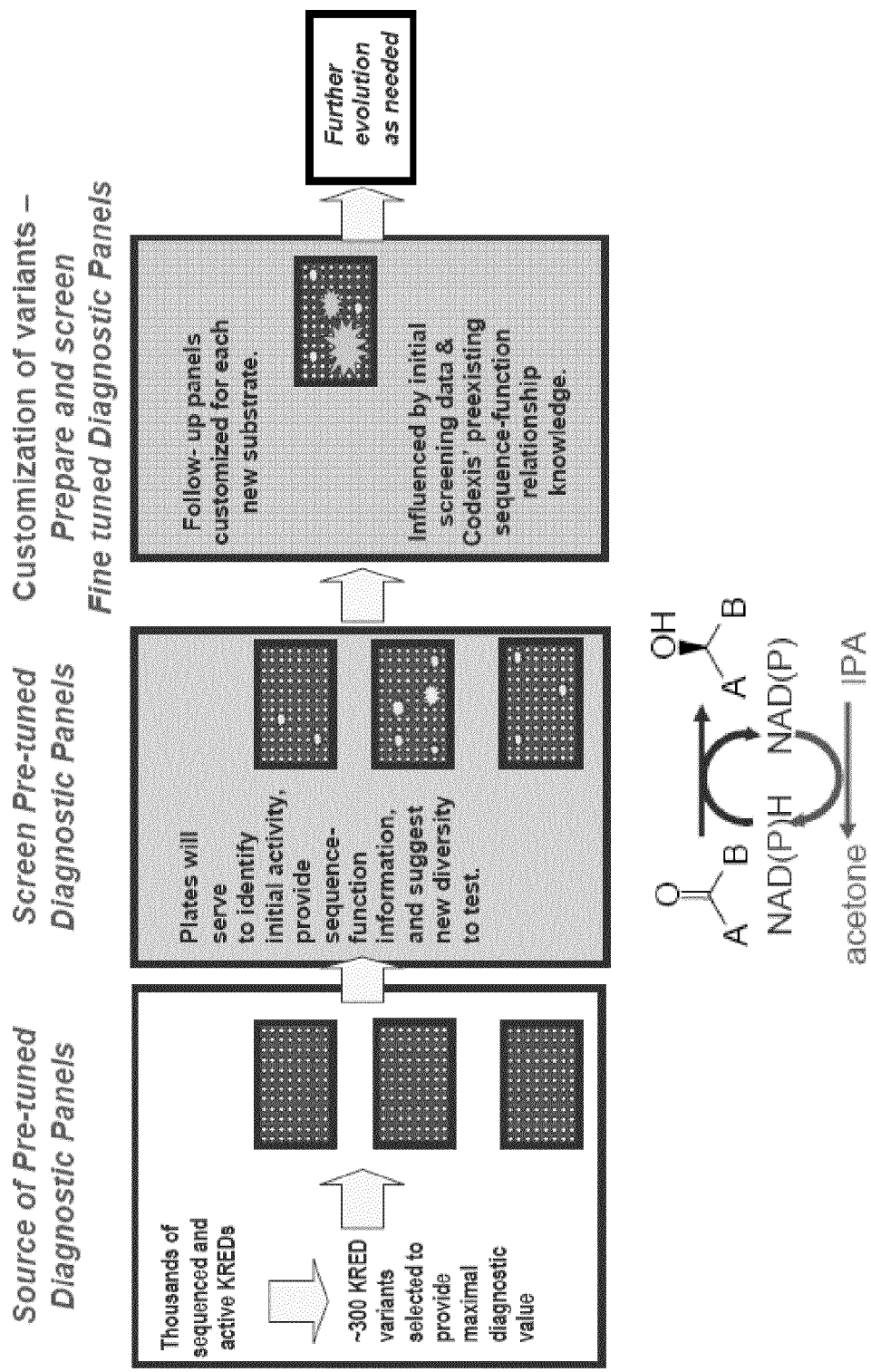
FIG. 5 illustrates an example of a method of screening a plurality of active polypeptide variants with a substrate of interest to identify those variants active on the substrate of interest, and the preparation and screening of a second plurality of polypeptide variants to identify a polypeptide variant with enhanced properties.

In some embodiments, a pre-tuned plurality is screened to identify active variants and provide sequence-activity relational information, and this information is used for diversification and customization of new variants for populating a fine-tuned plurality, which can then be screened with one or more substrates. (See FIG. 5). In some embodiments, the pre-tuned plurality is subjected to screening with substrates that have not previously been tested (i.e., naïve substrates). In some embodiments, a previously non-reactive or unproductive substrate can be used to screen the plurality. In some embodiments, a substrate of unknown physical or chemical identity can be used to screen the plurality. In some embodiments, multiple substrates from a class can be used to screen the plurality. In some embodiments, multiple and/or diverse classes of substrates are used to screen the plurality. The screening involves measurement of one or more activity parameters of interest, e.g. conversion, stereoselectivities, stereospecificities, regiospecificities, and the like. For each new substrate, this screening may result in none, some, or all members of the plurality exhibiting activity.

(b) Generation of a "Higher Resolution" or "Fine-Tuned" Plurality.

The activities, selectivities, or specificities of variants identified among the pre-tuned plurality when screened with a new substrate may not be sufficient for the desired use of the enzymatic reaction of the substrate. If only one variant is identified to have the desired activity upon the substrate, a sequence-activity relationship similar to that used to generate the pre-tuned plurality (as described above) may be assessed, using the identified active variant as a parent polypeptide to generate a refined, second-tier or second-generation plurality which is fine-tuned for activity upon the new substrate. If a small number of members of the pre-tuned plurality show activity (e.g., equal or less than ten variants), the member with the highest activity or selectivity may be chosen as the parent polypeptide for generation of a fine-tuned plurality. Combinations of the mutations in the variants of the pre-tuned plurality which exhibited activity are then incorporated into new "combinatorial" variants to create the fine-tuned plurality. Additionally, new mutations predicted based on the original sequence-activity map, as well as additional residue options at positions shown to be important for this substrate may be included. If a larger number of variants of the pre-tuned plurality (e.g., greater than about ten variants) exhibit activity upon a substrate, ProSAR-type algorithms may be used to predict beneficial and detrimental mutations among the active variants. The putative beneficial mutations can then be combined in new variants in a fine-tuned plurality.

In some embodiments, the pre-tuned plurality of polypeptide variants is screened and used to derive sequence-activity relationships, and mutations among the variants that exhibit a beneficial relationship to a desired activity are selected and are combinatorially recombined in second-generation variants that are used to populate a second-generation, fine-tuned plurality, which is then screened for one or more desired activities. In some embodiments, the fine-tuned plurality is populated by selecting one or more amino acid mutations from two or more polypeptides of the pre-tuned (low resolution) panel, which two or more polypeptides exhibited enhanced activity upon screening with the substrate or ligand, and combining these mutations to design second generation combinatorial variant polypeptides.

(c) Use of the Fine-Tuned Plurality.

From the pre-tuned variants, sequence-activity relationships can be determined and used to design and populate a new fine-tuned plurality, which can be screened under the same or different (e.g., more stringent) conditions, as in (b) of this example.

Example 3

Construction of a Plurality of Genetically Divergent, Functionally Diverse Ketoreductases for Identifying Sequence-Activity Relationships in Enzymes that Reduce Ketones to Chiral Alcohols This Example illustrates the generation of a plurality of robust and genetically divergent enzymes, each of which reacts with a substrate to produce a product, and wherein at least two members of the plurality react with different substrates or react with differing levels of activity upon a given substrate.

(a) Identification and Characterization of an Ancestral Ketoreductase.

In this example, the wild-type ketoreductase of *Lactobacillus kefir* (ADH-LK), whose native gene (Genbank Acc. No.: AAP94029.1) and amino acid sequence (SEQ ID NO:9 in U.S. Pat. No. 6,037,158, and SEQ ID NO:4 of U.S. Provisional Patent Application No. 60/900,430, incorporated in its entirety herein) and activity for the reduction of acetophenone to R-1-phenethyl alcohol have been reported, was chosen as the ancestral enzyme for development into a robust plurality of genetically divergent, functionally diverse ketoreductases.

The amino acid sequences of natural homologs of this ketoreductase have been reported, and the crystal structure of the wild-type homolog from *Lactobacillus kefir* (ADH-LB) having 88.5% sequence identity to ADH-LK has been reported (SEQ ID NO:8 in U.S. Pat. No. 6,037,158; *J. Mol. Biol.* 327:317-28 (2003); *J. Mol. Biol.* 349:801-13 (2005)).

A gene encoding the ancestral ketoreductase was designed for expression in *E. coli* based on the reported amino acid sequence and a codon optimization algorithm (SEQ ID NO:3 in U.S. Provisional Patent Application No. 60/900,430). Using standard methods, the gene was synthesized and cloned into an expression vector, and the resulting plasmid was transformed into an *E. coli* strain. Cells from a colony of this *E. coli* strain harboring the plasmid were grown in a liquid culture medium containing an antibiotic for which the expression vector provides resistance, and the cells were induced to produce the ketoreductase. The cells were harvested, suspended in buffer and lysed, and the cell debris were removed. The activity of the ketoreductase in the lysate for the reduction of acetophenone to R-1-phenethyl alcohol in the presence of NADPH cofactor, using isopropanol as reductant (being oxidized to acetone) was confirmed. See Examples 1 through 5 of U.S. Provisional Patent Application No. 60/900, 430.

The ancestral ketoreductase was determined to be not sufficiently robust to desired ketone reduction process reaction conditions. The desired reaction conditions change over the course of the reaction and comprise an aqueous solution of the ketoreductase containing several fold excess of isopropanol as reductant with a stoichiometric amount being converted to acetone coproduct, in contact with a high concentration of substrate, either dissolved or in a separate phase, being converted to product, likewise either dissolved or in a separate phase. For some substrates, it is desirable to use a cosolvent (e.g. tetrahydrofuran) to increase the solubility of the substrate in the aqueous solution. For some ketone reductions, it is desirable to conduct the reaction at elevated temperatures (e.g. 30-70° C.). In this example, the ancestral ketoreductase was not robust to these various desired process conditions, being negatively affected by the presence of high levels of the organics (substrate, product, isopropanol, acetone, cosolvent) and increased temperature. The ancestral ketoreductase loses activity over the course of the conversion of the ketone, prolonging the reaction time which results in further activity loss and further prolongation of the reaction time. Under some desired process conditions, the desired initial load of the ancestral ketoreductase loses all activity prior to complete conversion of the ketone; thus, the generation and identification of a robust enzyme able to withstand the desired process conditions was desired.

Additionally, the recombinant expression vector encoding the ancestral ketoreductase provided a lower level of expression than that desired for scaleable production of the ketoreductase. Thus, it was desired to enhance the expression levels of the ketoreductase.

(b) Identification of a Robust and Scaleable Parent Ketoreductase.

Directed evolution was used to obtain variants of the ancestral enzyme having sufficiently improved robustness to desired process conditions, making these variants more suitable for use as a parent enzymes from which variants are generated to populate the ketoreductase plurality. Mutations were introduced into the gene encoding the ancestral ketoreductase using one or a combination of the following techniques: error-prone PCR; site saturation mutagenesis; family shuffling of homologs; semi-synthetic shuffling introducing amino acid diversity present in wild-type homologs of the ancestral ketoreductase; and site directed mutagenesis at sites identified as likely to affect stability based on the packing of interior residues of a protein or optimization of subunit interactions as discerned from the crystal structure.

The mutant libraries derived from the ancestral ketoreductase were screened for the activity of the ketoreductase variants in cell lysates. To screen for more robust variants, the variants were screened for activity for the reduction of NADP by isopropanol after prolonged exposure of the variants in the aqueous lysates to isopropanol and to isopropanol-acetone mixtures prior to initiating the screening reaction with the addition of NADP. The increase in fluorescence of NADPH was monitored. In one such challenge screen, the variants were exposed overnight to a mixture of isopropanol and acetone prior to the addition of NADP to initiate the reaction. In another such screen, tetrahydrofuran was included in the mixture prior to initiating the reaction. In another such screen, the screening mixture was incubated at elevated temperature for several hours.

Variants that exhibit increased activity for NADP reduction by isopropanol as compared to the ancestral ketoreductase after such challenges to their robustness were subjected to further directed evolution by DNA shuffling to generate and screen libraries that comprise new combinations of the mutations present among the improved variants identified in the initial libraries. In parallel, additional new beneficial mutations were identified by the methods described above and are included in additional DNA-shuffled combinatorial libraries.

The directed evolution screens compared the ketoreductase activities in the cell lysates, and thereby resulted in the identification of variants that are produced in greater amounts (their encoding genes are better expressed) alongside those variants having higher intrinsic activity, as well as variants with combinations of increase expression and higher intrinsic activity.

The directed evolution program identified variants of the ancestral ketoreductase that are produced at high levels (e.g. >20% of the cell protein) and are sufficiently robust to the various desired process conditions to be suitable parent ketoreductases for functional diversification. The amino acid sequence of the selected parent ketoreductases were determined by nucleotide sequencing and translation of their encoding genes. Examples of more highly produced and robust ketoreductase variants of ADH-LK are disclosed in U.S. Provisional Patent Application Nos. 60/900,430, 60/900,494, 60/957,974, 60/972,058, 60/976,345, and 60/976,555, each of which is incorporated by reference in its entirety herein.

(c) Generation of Binding Pocket Diversity.

A plurality of ketoreductase variants derived from the selected parent ketoreductases was generated by diversification of amino acids that comprise the substrate binding pocket, as identified by by homology of the ancestral ketoreductase, ADH-LK, to the reported crystal structure of ADH-LB. Binding pocket mutations were introduced in the gene encoding the parent ketoreductase by one of the methods described above. Additionally, specific desired mutations were identified in silico by docking studies of diverse ketone substrate structures in the active site of the homology model of the ancestral ketoreductase and were introduced in vitro by site directed mutagenesis. These include mutations that were predicted to change the stereoselectivity from R-selective to S-selective, with acetophenone as the reference prochiral substrate.

Reductions of NADP and diverse ketone substrates by isopropanol were used to determine which variants among the binding-pocket variants are viable, functional ketoreductases. The amino acid sequences of the variants with functional binding pocket diversity were determined by nucleotide sequencing and translation of their encoding genes. The diverse ketone substrates and the functional diversity of amino acid sequences derived from the sequence of the ancestral ADH-LK and the parent ADH-LK variants, and specific mutations conferring such functional diversity, include the substrates, sequences, and mutations disclosed in U.S. Provisional Patent Application Nos. 60/900,430, 60/900,494, 60/957,974, 60/972,058, 60/976,345, and 60/976,555. Selected diverse functional variants were consolidated into a plurality of addressable ketoreductases of known sequences and were individually populated into wells of multiwell microtiter plates, wherein the address of each well is its coordinates on a particular plate.

(d) Generation of Sequence-Activity Relationships.

The diverse activities and stereoselectivities of the ketoreductase variants in the plurality were characterized by screening the plurality against a diversity of ketone substrates, including the diverse ketone substrates used to identify individual functional variants. The ketone substrates included ones that differ in the nature and size of the two substituents bound to the carbon atom of the keto group. Ketones with alkyl, aryl, aralkyl or heterocyclic substituents to the carbonyl carbon are used, among which neither, one, or both of the substituents is bulky. The following ketones were used to determine the activity and stereoselectivity characteristics of the variants: acetophenone (see U.S. Provisional Patent Application No. 60/900,430), 3-ketothiolane (see U.S. Provisional Patent Application No. 60/957,974), a prochiral substituted acetophenone with two ortho-chloro substituents (2', 6'-dichloro-3'-fluoroacetophenone; see U.S. Provisional Patent Application No. 60/972,058); a prochiral methyl heteroaryloxymethyl ketone in which the heteroaryloxymethyl has mass 325 (the compound of structural formula (I) in U.S. Provisional Patent Application No. 60/900,494); a prochiral aryl aralkyl ketone in which the aryl group has mass 265 and the aralkyl group has mass 163 (2-[3-[3-[2-(7-chloro-2-quinolinyl)ethenyl]phenyl]-3-oxopropyl]benzoic acid methyl ester; see U.S. Provisional Patent Application No. 60/976,345); and a prochiral alkyl heteroaryl ketone in which the alkyl group has mass 72 and the heteroaryl group has mass 83. Additionally a racemic alpha-methyl aldehyde was used to determine the activity and stereospecificity characteristics of the variants for kinetic resolution of racemic alpha-chiral aldehydes.

Reduction of each ketone (and aldehyde) by isopropanol, in the presence of NADP, was used to determine the activity characteristics of the functional binding pocket variants. Activity characteristics determined for these different prochiral ketone substrates were the conversion of an amount of the ketone (or aldehyde) and the enantiopurity of the chiral alcohol product, measured by chiral gas or liquid chromatography. For each substrate, a range of conversions was found among the functional variants. For any given substrate, the percent conversion observed upon screening the plurality of variants ranged from none to complete conversion. For each prochiral ketone substrate, a range of enantioselectivities was found among the variants having activity on the ketone. Enantioselectivities ranged from >99.9% R-selective to >99.9% S-selective. For the racemic alpha-chiral aldehyde a range of enantiospecificities was found among the variants having activity on the aldehyde, some being S-specific and some being R-specific to varying degrees.

By combining the conversion and enantioselectivity (or enantiospecificity) data with the amino acid sequence information from the variants active on each substrate, sequence-activity relationships (including sequence-enantioselectivity or sequence-enantiospecificity relationships) for each substrate were generated using a protein sequence-activity relationship algorithm (ProSAR).

(e) Population of the Pre-Tuned Plurality.

The information from the sequence-activity relationships so generated was used to populate a pre-tuned plurality of ketoreductase variants for use in screening for activity and selectivity on additional substrates. The variants chosen for the pre-tuned plurality were selected to optimize the representation of variants in the pre-tuned plurality that exhibit both the functional (activity/selectivity/specificity) diversity over all the substrates previously tested and the genetic diversity from the binding pocket mutations. Variants were selected and new variants designed to incorporate and combine single mutations and/or combinations of mutations identified in the previous screen to be important based on the sequence-activity relationships. Variants were selected to maintain the same pattern of diversity of activities and selectivities (or specificities) for each substrate in the pre-tuned plurality as are seen in the larger plurality representing functional binding pocket diversity. To reduce the number of variants in the pre-tuned plurality, one representative member of a subset of variants having single amino acid mutations of a similar character (conservative mutations) at a particular position (e.g., a representative variant is selected from variants having R or K substituted at a particular position, variants having E or D substituted at a particular position, variants having V or I substituted at a particular position, etc.) while retaining activity, was selected.

A computer algorithm was also be applied to reduce the size of the plurality of the variants for the pre-tuned plurality. For example, a genetic algorithm with a fitness function that assigns weights to maximize the functional (activity and selectivity on all substrates) and genetic diversity. This algorithm can be used to optimally select a population of variants with a wide range of functional and genetic diversity.

The ketoreductase variants selected for the pre-tuned plurality were consolidated as a plurality of addressable ketoreductases and used to populate two 96-well microtiter plates, such that the amino acid sequence of the variant located at each address (plate identifier and well coordinates) was known.

Example 4

Screening a Pre-Tuned Plurality of Genetically Divergent, Functionally Diverse Ketoreductases with a Substrate that is a Known Substrate for Some Variants in the Plurality Sealed microtiter plates (2×96-deep well sterile plates; Costar #3960) populated with the pre-tuned plurality of ketoreductases of Example 3, in the form of frozen clarified lysates comprising the recombinantly expressed enzymes, were allowed to thaw at room temperature and then centrifuged (5 min, 4000 rpm, 4° C.). 50 µl of a solution containing 5 mg/mL nicotinamide adenine dinucleotide phosphate (NADP$^+$, Na salt), 2 mM MgSO$_4$ and 100 mM triethanolamine (chloride) buffer (pH 7.0) was added to each well, followed by 300 µl of isopropanol, and then 50 µl of 100 mg/mL acetophenone in tetrahydrofuran. The plate was resealed and shaken on an orbital shaker (850 rpm, room temperature) for 24 hours. To work up the samples, 1 mL of methyl t-butyl ether was added to each well. The plate was resealed and shaken (850 rpm, room temperature) for 10 minutes, then was centrifuged for 2 min (4000 rpm, 4° C.). 50 µl of the organic phase in each well was transferred to a well of a 96-well round bottom shallow well microtiter plate (Costar #3365, polypropylene) containing 150 µl of methyl t-butyl ether. The resulting sample plates were sealed and stored frozen until analysis.

The samples were analyzed by normal phase HPLC on a 4.6×250 mm Chiralcel OD-H (Chiral Technologies Inc.) column at 40° C. using 95:5 heptane/ethanol as mobile phase with a flow rate of 1.5 mL min$^{-1}$, monitored at 215 nm.

FIG. 8 shows a plot of the % conversion of acetophenone and the % enantiomeric excess (e.e.) of the resulting 1-phenethanol. Positive e.e. values are predominantly R-1-phenethanol and negative e.e. values are predominantly S-1-phenethanol.

This example illustrates a plurality of polypeptides related to an ancestral polypeptide wherein different members of the plurality react with different levels of activity and different directions and levels of stereoselectivity on a given substrate.

Example 5

Screening a Pre-Tuned Plurality of Genetically Divergent, Functionally Diverse Ketoreductases with a Second Substrate that is a Known Substrate for Some Variants in the Plurality The procedure was identical to that of Example 4 with the exception that 50 µl of 50 mg/mL 3-ketothiolane in tetrahydrofuran was used instead of the acetophenone solution and the samples were analyzed by HPLC on a 4.6×150 mm Chiralpak IA (Chiral Technologies Inc.) column at 40° C.

using 97:3 heptane/ethanol as mobile phase with a flow rate of 1.5 mL min$^{-1}$, monitored at 210 nm.

FIG. 9 shows a plot of the % conversion of 3-ketothiolane and the % enantiomeric excess (e.e.) of the resulting 3-hydroxythiolane. Positive e.e. values are predominantly R-3-hydroxythiolane and negative e.e. values are S-3-hydroxythiolane.

This example illustrates a plurality of polypeptides related to an ancestral polypeptide wherein different members of the plurality react with different levels of activity and different directions and levels of stereoselectivity on a given substrate. By comparison to Example 4 (FIG. 8), this example further illustrates a plurality of polypeptides related to an ancestral polypeptide wherein members of the plurality react with different activities and different stereoselectivities on different substrates.

Example 6

Use of a Plurality of Genetically Divergent, Functionally Diverse Ketoreductases for Identification of One or More Ketoreductases Having Desired Activities on a Naïve Substrate This example illustrates the use of a pre-tuned plurality of ketoreductase polypeptides related to an ancestral polypeptide, wherein different members of the plurality react with different levels of activity and different levels of stereoselectivity on a new substrate not previously tested or used in constructing the pre-tuned plurality. It further illustrates the generation of a fine-tuned plurality of ketoreductase polypeptides based on sequence-activity relationships indicated and/or suggested by the activities and stereoselectivities of the members of the pre-tuned plurality on the new substrate, and the screening of the fine-tuned plurality on the new substrate to identify one or more members of the fine-tuned plurality having enhanced activity and/or stereoselectivity compared to the members of the pre-tuned plurality.

(a) Use of the Pre-Tuned Plurality.

The pre-tuned plurality of addressable ketoreductases of Example 3 was screened with an aryl alkyl ketone in which the aryl group had mass 96 and the alkyl group was substituted, had mass 233, and had a chiral carbon center of S-configuration six atoms removed from the keto group: (S)-1-(4-Fluoro-phenyl)-5-(2-oxo-4-phenyl-oxazolidin-3-yl)-pentane-1,5-dione.

The procedure was identical to that of Example 4 with the following exceptions: 125 µl of isopropanol containing 1 g/L (S)-1-(4-Fluoro-phenyl)-5-(2-oxo-4-phenyl-oxazolidin-3-yl)-pentane-1,5-dione was used instead of the 300 µl of isopropanol and the solution of acetophenone in tetrahydrofuran; the sealed reaction plate was shaken for 65 hours instead of 24 hours; 200 µl of the methyl t-butyl ether organic phase was transferred to the sample plates; and the samples were analyzed by normal phase HPLC on a 2.1×150 mm Chiralcel OD-H (Chiral Technologies Inc.) column at 40° C. using 80:20 hexane/ethanol as mobile phase with a flow rate of 1.0 mL min$^{-1}$, monitored at 215 nm.

Figure 6:
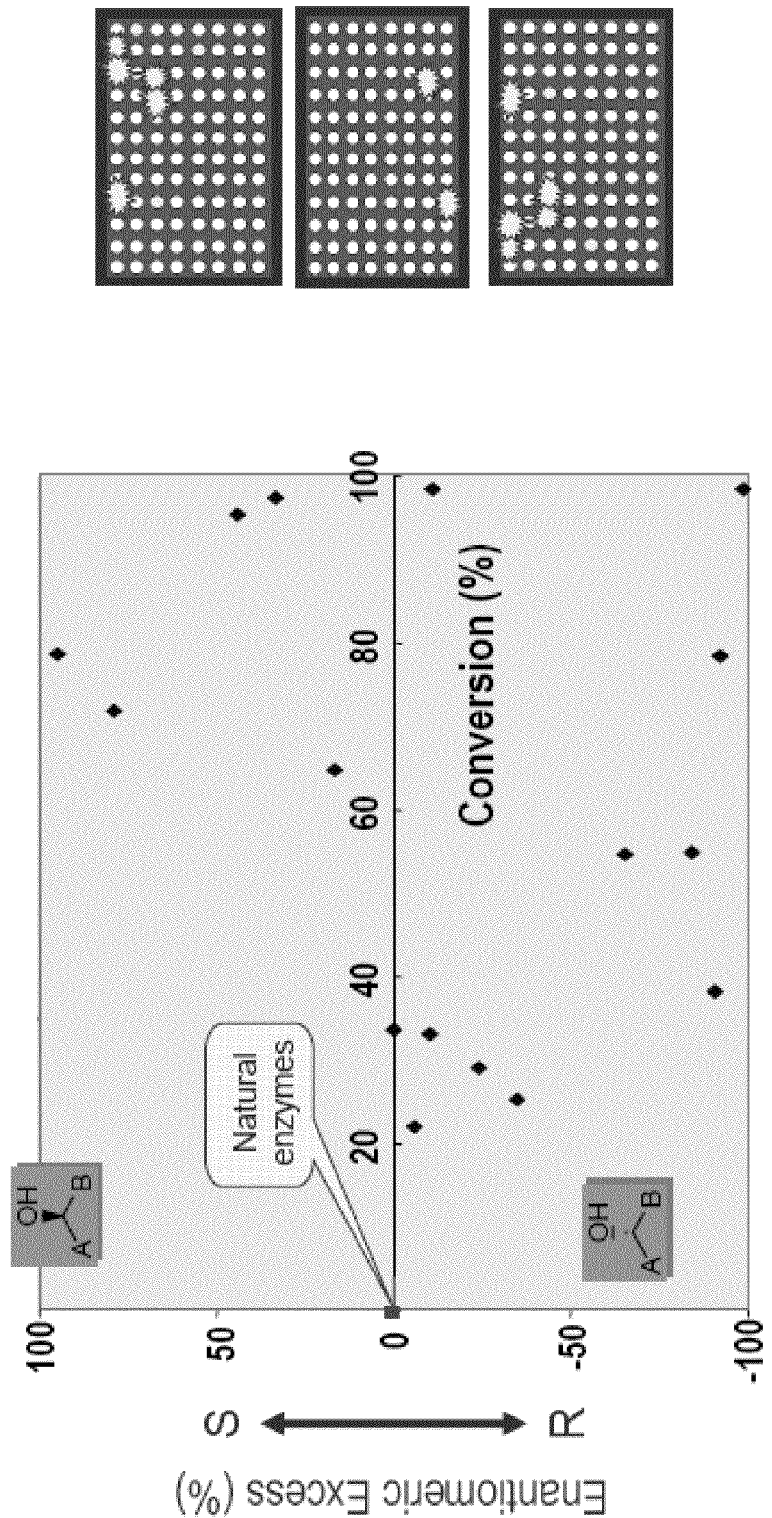
FIG. 6 illustrates an exemplary range of activities and enantioselectivities exhibited by a pre-tuned plurality of ketoreductase polypeptide evolvants on a new substrate, (S)-1-(4-Fluoro-phenyl)-5-(2-oxo-4-phenyl-oxazolidin-3-yl)-pentane-1,5-dione, not tested during the generation and compilation of the plurality. See Example 6.

A range of conversions and a range of diastereoselectivities were found among the pre-tuned plurality. Sixteen variants converted >20% of the ketone substrate. The conversion and diastereoselectivity data for these variants is illustrated in FIG. 6. The range of diastereoselectivities included both predominantly S-selective (giving the predominantly the desired S,S-diastereomer (positive stereomeric excess values in FIG. 6), and predominantly R-selective (giving predominantly the undesired R,S-diastereomer (negative stereomeric excess values in FIG. 6). The conversions ranged from 0 to 98.4% (for two variants, giving −11% d.e. and −98.5% d.e.). The highest conversions with +d.e. were 95.7% (+44% d.e.) and 97.4% (+33% d.e.). The highest +d.e. was 94.9% for a variant that yielded 78.8% conversion. An additional eleven variants convert between 10 and 20% of the ketone, with diastereoselectivities in the range from −11% to +76% d.e.

Separately, the ancestral (wild-type) ketoreductase was tested for its activity on the this new ketone substrate under the same conditions. It exhibited no detectable activity.

(b) Generation of a Fine-Tuned Plurality.

The activities and diastereoselectivities identified among the pre-tuned plurality of ketoreductase variants in part (a) were used to design a new plurality of ketoreductase variants, fine-tuned to identify variants with enhanced activity and diastereoselectivity for the new substrate. ProSAR analysis was used to develop sequence-activity and sequence-diastereoselectivity relationships for the mutations among the variants in the pre-tuned plurality exhibiting activity. The relationships were used to identify the mutations that were beneficial and detrimental, and to what degree, for each of the activities (conversion) of the variants and the diastereoselectivity (d.e.) of the variants. A fine-tuned plurality of eighty-four new variants, not present in the pre-tuned plurality, was designed, wherein the variants comprised new combinations of the mutations identified as beneficial for one or both of the conversion and the desired (+) diastereoselectivity, but no more than weakly detrimental for the other. Mutations not present in the pre-tuned plurality but predicted to be potentially beneficial (e.g. one or more conservative mutations from a mutation identified as beneficial among the pre-tuned variants) were also included in the combinations designed for the fine-tuned plurality.

Genes encoding the eighty four new variants were individually synthesized, their sequences were confirmed, and they were used to produce the eighty-four individual new variants. The fine-tuned plurality of addressable ketoreductase variants was consolidated, using them to populate a 96-well microtiter plate. Of the 96-well plate, 12 wells on the plate were populated with six negative control replicates and six positive control replicates. The positive control was the highest +d.e. variant from the pre-tuned plurality. The amino acid sequence of the variant located at each well address was known.

(c) Use of the Fine-Tuned Plurality.

The fine-tuned plurality was subjected to screening with the new ketone substrate used in part (a), but under more demanding conditions (more substrate and less reaction time). The procedure was identical to that of part (a) in this Example, with the exceptions that the 125 µl of isopropanol contained 2 g/L (S)-1-(4-Fluoro-phenyl)-5-(2-oxo-4-phenyl-oxazolidin-3-yl)-pentane-1,5-dione was used instead of 1 g/L and the sealed reaction plate was shaken for 16 hours instead of 65 hours.

The conversion and diastereoselectivity data from this screen of the fine-tuned plurality is illustrated in FIG. 7. Under these more demanding conditions, the variant used as positive control, which gave 78.8% conversion, +94.9% d.e. in the pre-tuned plurality screen, exhibited 24% average conversion, +94.4% average d.e. Among the fine tuned plurality, all the active variants but three exhibited +d.e. Twenty-two variants exhibited higher conversion than the positive control, all but one of them with +d.e., six of them with higher +d.e. than the positive control, and three of them with essentially >+99.9% d.e. (R,S-diastereomer was undetected). The variant giving the highest conversion, 98.1%, was one of the variants exhibiting >+99.9% d.e.

Example 7

Use of a Plurality of Genetically Divergent, Functionally Diverse Ketoreductases for Identification of One or More Ketoreductases Having Desired Activities on Another Naïve Substrate This example illustrates the use of a pre-tuned plurality of ketoreductase polypeptides related to an ancestral polypeptide, wherein different members of the plurality react with different levels of activity and different levels of stereoselectivity on a new substrate not previously tested or used in constructing the pre-tuned plurality. It further illustrates the generation of a fine-tuned plurality of ketoreductase polypeptides based on sequence-activity relationships indicated and/or suggested by the activities and stereoselectivities of the members of the pre-tuned plurality on the new substrate, and the screening of the fine-tuned plurality on the new substrate to identify one or more members of the fine-tuned plurality having enhanced activity and/or stereoselectivity compared to the members of the pre-tuned plurality.

(a) Use of the Pre-Tuned Plurality.

The pre-tuned plurality of addressable ketoreductases of Example 3 was screened with 3-butyn-2-one. The desired product was (S)-3-butyn-2-ol.

Sealed microtiter plates populated with the pre-tuned plurality of ketoreductases of Example 3, in the form of frozen clarified lysates comprising the recombinantly expressed enzymes, were allowed to thaw at room temperature and then centrifuged (5 min, 4000 rpm, 4° C.). 150 µl of a solution containing 167 mg/mL 3-butyn-2-one, 0.83 mg/mL nicotinamide adenine dinucleotide phosphate (NADP$^+$, Na salt), and 67% isopropanol (IPA) in 50 mM phosphate (sodium) buffer (pH 7.0) was added to each well. The final concentration of each component was as follows: 100 mg/mL 3-butyn-2-one, 0.5 mg/mL NADP$^+$, 40% IPA in 50 mM phosphate (sodium) buffer. The plate was resealed and shaken on an orbital shaker (850 rpm, room temperature) for 24 hours. To work up the samples, 1 mL of methyl t-butyl ether was added to each well. The plate was resealed and shaken (850 rpm, room temperature) for 10 minutes, then was centrifuged for 2 min (4000 rpm, 4° C.). 200 µl of the organic phase in each well was transferred to a well of a 96-well round bottom shallow well polypropylene microtiter plate. The resulting sample plates were sealed and stored frozen until analysis.

The samples were analyzed by GC-FID on a 30 m×0.25 mm (0.25 µM film) Chrompack CP-Chiralsil-Dex CB chiral column (Varian Inc.) using the following program: 15 psi, 70° C. for 7 min, 25° C./min up to 200° C., 200° C. for 3 min.

The conversion and enantioselectivity data for these variants is illustrated in FIG. 10. A range of conversions and enantioselectivities was observed. Positive e.e. values are predominantly (R)-3-butyn-2-ol and negative e.e. values are predominantly (S)-3-butyn-2-ol. No member of the plurality gave greater than 70% enantiomeric excess to the desired (S)-3-butyn-2-ol.

(b) Generation of a Fine-Tuned Plurality.

The activities and diastereoselectivities identified among the pre-tuned plurality of ketoreductase variants in part (a) were used to design a new plurality of ketoreductase variants, fine-tuned to identify variants with enhanced activity and enantioselectivity for the new substrate. ProSAR analysis was used to develop sequence-activity and sequence-enantioselectivity relationships for the mutations among the variants in the pre-tuned plurality exhibiting activity. A fine-tuned plurality of new variants, not present in the pre-tuned plurality, was designed, wherein the variants comprised new combinations of the mutations identified as beneficial for one or both of the conversion and the desired (S)-enantioselectivity. Mutations not present in the pre-tuned plurality but predicted to be potentially beneficial (e.g. one or more conservative mutations from a mutation identified as beneficial among the pre-tuned variants) were also included in the combinations designed for the fine-tuned plurality.

Genes encoding the new variants were individually synthesized, their sequences were confirmed, and they were used to produce the individual new variants. The fine-tuned plurality of addressable ketoreductase variants was consolidated, using them to populate a 96-well microtiter plate. The amino acid sequence of the variant located at each well address was known.

(c) Use of the Fine-Tuned Plurality.

The fine-tuned plurality was subjected to screening with 3-butyn-2-one. The procedure was identical to that in part (a) of this Example with the exception that a newly acquired supply of 3-butyn-2-one was used. The new material gave lower conversions with the member of the pre-tuned plurality, the parent variant, that was also used as a positive control on the microtiter plate populated with the fine-tuned plurality. In the screen of the pre-tuned plate, the parent ketoreductase gave 53% conversion. In the screen of the fine-tuned plate, the parent ketoreductase also on the microtiter plate, gave 26% conversion. Thus, with respect to conversion, the screen of the fine-tuned plurality was under more demanding conditions than the screen of the pre-tuned plurality.

The conversion and diastereoselectivity data from this screen of the fine-tuned plurality is illustrated in FIG. 11. Comparison of FIGS. 10 and 11 shows, especially in view of the more demanding conditions of the screen of the fine-tuned plurality, members of the fine having greater activity than any members of the pre-tuned plurality. Whereas the majority of the members of the pre-tuned plurality gave predominantly (R)-3-butyn-2-ol (positive e.e. values in the Figures), all the members of the fine-tuned plurality gave predominantly (S)-3-butyn-2-ol (negative e.e. values in the Figures). Whereas the most (S)-stereoselective member of the pre-tuned plurality gave <70% e.e. (S)-3-butyn-2-ol, several, eight members of the fine tuned plurality gave >90% e.e. (S)-3-butyn-2-ol.

Example 8

Construction of a Plurality of Genetically Divergent, Functionally Diverse Enone Reductases for Identifying Sequence-Activity Relationships in Enzymes that Reduce Carbon-Carbon Double Bonds Conjugated to a Carbonyl Group This Example illustrates the generation of a plurality of robust and genetically divergent enzymes, each of which reacts with a substrate to produce a product, and wherein at least two members of the plurality react with different substrates or react with differing levels of activity upon a given substrate.

(a) Selection of an Ancestral Enone Reductase.

In this example, variants of Old Yellow Enzyme (OYE1, OYE 2 and OYE3) were chosen as ancestral enzymes for development into a robust plurality of genetically divergent, functionally diverse enone reductases. The amino acid sequences of these natural homologs and others are reported and the crystal structure of the OYE 1 is available.

Genes encoding the ancestral OYEs were designed for expression in *E. coli* based on the reported amino acid sequences and a codon optimization algorithm. Using standard methods, the gene was synthesized and cloned into an expression vector, and the resulting plasmid was transformed into an *E. coli* strain. Cells from colonies of the transformed *E. coli* strain were grown and induced to produce the enzymes. The cells were harvested, suspended in buffer and lysed, and the cell debris were removed. The enzymes were well expressed and their activity in the lysate for the reduction of cyclohexenone to cyclohexanone by NADPH was confirmed.

The ancestral OYEs were determined to be not sufficiently robust to desired enone reduction process reaction conditions, and required improvements in thermal stability and stability to organic reactants and solvents such as isopropanol, acetone, and tetrahydrofuran. On incubation in neutral buffer solution at 50° C., OYE 1 loses all activity for reduction of cyclohexenone with one-half hour. Under the same conditions, OYE 2 and OYE 3 lose >95% of their activity by two hours, and all measurable activity within 3.5 hours.

(b) Identification of a Robust and Scaleable Parent Enone Reductase.

Directed evolution was used to obtain an OYE variant having sufficiently improved robustness to desired process conditions, making it more suitable for use as a parent enzyme from which variants were generated to populate the enone reductase plurality. The synthetic genes encoding OYE 1, OYE 2, and OYE were family DNA shuffled and the resulting shuffled library was screened for variants having improved thermal stability and stability to organic reactants and solvents such as isopropanol, acetone, and tetrahydrofuran. On incubation in neutral buffer solution at 50° C., the shuffled variant selected as parent ketoreductase for constructing the pre-tuned plurality retains >70% of its activity for cyclohexene reduction after one-half hour and after 1 hour, and >65% of its activity after 3.5 hours.

(c) Generation of Binding Pocket Diversity.

A plurality of enone reductase variants derived from the selected robust parent enone reductase was generated by diversification of amino acids that comprise the substrate binding pocket, as identified by the reported crystal structure of OYE 1. Binding pocket mutations were introduced in the gene encoding the parent enone reductase by one of the methods described in Example 3(b). Additionally, specific desired mutations were identified in silico by docking studies of diverse substrate structures in the active site of the crystal structure of the ancestral OYE 1 and were introduced in vitro by site directed mutagenesis. These include mutations that were predicted to change the stereoselectivity for prochiral substrates.

Reductions of diverse ketone substrates were used to determine which variants among the binding-pocket variants are viable, functionally diversified enone reductases. The amino acid sequences of the variants with functional binding pocket diversity were determined by nucleotide sequencing and translation of their encoding genes. Selected diverse functional variants were consolidated into a plurality of addressable enone reductases of known sequences and were individually populated into wells of multiwell microtiter plates, wherein the address of each well is its coordinates on a particular plate.

(d) Generation of Sequence-Activity Relationships.

The diverse activities and stereoselectivities of the enone reductase variants in the plurality were characterized by screening the plurality against a diversity of substrates, including the diverse substrates used to identify individual functional variants. Substrates used characterize the diversity included 3-methyl-cyclohexenone, S-carvone, (±)-8a-Methyl-3,4,8,8a-tetrahydro-1,6(2H,7H)-naphthalenedione, and phenyl methacrylate.

Reduction of each substrate by isopropanol, in the presence of NADP and an alcohol dehydrogenase and/or by glucose, in the presence of NADP and a glucose dehydrogenase, was used to determine the activity characteristics of the functional binding pocket variants. Activity characteristics determined for prochiral substrates were the conversion of an amount of the substrate and the direction and level of the stereoselectivity to the chiral product, measured by chiral gas or liquid chromatography. For each substrate, a range of conversions was found among the functional variants. For any given substrate, the percent conversion observed upon screening the plurality ranged from none to complete conversion. For each prochiral substrate, a range of stereoselectivities was found among the variants having activity on the substrate.

By combining the conversion and stereoselectivity data with the amino acid sequence information from the variants active on each substrate, sequence-activity relationships (including sequence-stereoselectivity relationships) for each substrate were generated using a protein sequence-activity relationship algorithm (ProSAR).

(e) Population of the Pre-Tuned Plurality.

The information from the sequence-activity relationships so generated was used to populate a pre-tuned plurality of enone reductase variants for use in screening for activity and selectivity on additional substrates. The variants chosen for the pre-tuned plurality were selected to optimize the representation of variants in the pre-tuned plurality that exhibit both the functional (activity/selectivity) diversity over all the substrates previously tested and the genetic diversity from the binding pocket mutations. Variants were selected and new variants designed to incorporate and combine single mutations and/or combinations of mutations identified in the previous screen to be important based on the sequence-activity relationships. Variants were selected to maintain the same pattern of diversity of activities and selectivities for each substrate in the pre-tuned plurality as are seen in the larger plurality representing functional binding pocket diversity. To reduce the number of variants in the pre-tuned plurality, one representative member of a subset of variants having single amino acid mutations of a similar character (conservative mutations) at a particular position while retaining activity, was selected.

A genetic algorithm with a fitness function that assigns weights to maximize the functional (activity and selectivity on all substrates) and genetic diversity was applied to reduce the size of the plurality of the variants for the pre-tuned plurality.

The enone reductase variants selected for the pre-tuned plurality were consolidated as a plurality of addressable enone reductases and used to populate one 96-well microtiter plate, such that the amino acid sequence of the variant located at each address (plate identifier and well coordinates) was known.

Example 9

Screening a Pre-Tuned Plurality of Genetically Divergent, Functionally Diverse Enone Reductases with a Substrate that is a Known Substrate for Some Variants in the Plurality A sealed microtiter plate populated with the pre-tuned plurality of enone reductase of Example 7, in the form of frozen clarified lysates comprising the recombinantly expressed enzymes, were allowed to thaw at room temperature and then centrifuged (5 min, 4000 rpm, 4° C.). 150 µl of a solution containing 8.3 mg/mL S-carvone, 0.83 mg/mL nicotinamide adenine dinucleotide phosphate (NADP+, Na salt), 3.3 mg/mL glucose dehydrogenase (GDH), 15 mg/mL D-glucose (1.5 equivalents), and 17% tetrahydrofuran in 100 mM phosphate (sodium) bugger (pH 7.5) was added to each well. The final concentration of each component was as follows: 5 mg/mL S-carvone, 0.5 mg/mL NADP+, 2 mg/mL GDH, 9 mg/mL D-glucose, 10% THF. The plate was resealed and shaken on an orbital shaker (850 rpm, room temperature) for 24 hours. To work up the samples, 1 mL of methyl t-butyl ether was added to each well. The plate was resealed and shaken (850 rpm, room temperature) for 10 minutes, then was centrifuged for 2 min (4000 rpm, 4° C.). 200 µl of the organic phase in each well was transferred to a well of a 96-well round bottom shallow well polypropylene microtiter plate. The resulting sample plates were sealed and stored frozen until analysis.

The samples were analyzed by GC-FID on a chiral 30 m×0.32 mm (0.25 µM film) HP-5 column (Agilent Technologies Inc.) at 20 psi, 125° C. for 3.25 min.

FIG. 12 shows a plot of the % conversion of S-carvone and the stereomeric excess (% d.e.) of the resulting (5S)-dihydrocarvone. Positive stereomeric excess values are predominantly (2R,5S)-cis-dihydrocarvone and negative stereomeric excess values are predominantly (2S,5S)-trans-dihydrocarvone.

This example illustrates a plurality of polypeptides related to an ancestral polypeptide wherein different members of the plurality react with different levels of activity and different directions and levels of stereoselectivity on a given substrate.

Example 10

Screening a Pre-Tuned Plurality of Genetically Divergent, Functionally Diverse Enone Reductases with a Second Substrate that is a Known Substrate for Some Variants in the Plurality The procedure was identical to that of Example 9 with the exceptions that the substrate solution contained 8.3 mg/mL 2-methyl-2-pentenal instead of the S-carvone and the samples were analyzed by GC-FID on a chiral 25 m×0.25 mm (0.25 µM film) Supelco Beta Dex-225 chiral column (Sigma-Aldrich) at 12 psi using the following temperature program: 80° C. for 9.5 min, 70° C./min up to 150° C., 150° C. for 2 min.

FIG. 12 shows a plot of the % conversion of 2-methyl-2-pentenal and the stereomeric excess (% e.e.) of the resulting 2-methyl-2-pentanal. Positive stereomeric excess values are predominantly R-2-methyl-2-pentanal and negative stereomeric excess values are predominantly S-2-methyl-2-pentanal.

This example illustrates a plurality of polypeptides related to a parent polypeptide wherein different members of the plurality react with different levels of activity and different directions and levels of stereoselectivity on a given substrate. By comparison to Example 9 (whose results are also shown in FIG. 12), this example further illustrates a plurality of polypeptides related to a parent polypeptide wherein members of the plurality react with different activities and different stereoselectivities on different substrates.

Example 11

Use of a Plurality of Genetically Divergent, Functionally Diverse Enone Reductases for Identification of One or More Ketoreductases Having Desired Activities on a Naïve Substrate This example illustrates the use of a pre-tuned plurality of enone reductase polypeptides related to a parent polypeptide, wherein different members of the plurality react with different levels of activity and different directions and levels of stereoselectivity on a new substrate not previously tested or used in constructing the pre-tuned plurality.

The procedure was identical to that of Example 9 with the exception that the substrate solution contained 8.3 mg/mL of R-carvone instead of the S-carvone.

FIG. 13 shows a plot of the % conversion of R-carvone and the stereomeric excess (% d.e.) of the resulting dihydrocarvone. Positive stereomeric excess values are predominantly (2S,5R)-cis-dihydrocarvone and negative stereomeric excess values are predominantly (2R,5R)-trans-dihydrocarvone.

Example 12

Use of a Plurality of Genetically Divergent, Functionally Diverse Enone Reductases for Identification of One or More Ketoreductases Having Desired Activities on Another Naïve Substrate This example illustrates the use of a pre-tuned plurality of enone reductase polypeptides related to a parent polypeptide, wherein different members of the plurality react with different levels of activity and different directions and levels of stereoselectivity on a another new substrate not previously tested or used in constructing the pre-tuned plurality.

The procedure was identical to that of Example 10 with the exceptions that the substrate solution contained 8.3 mg/mL 2-methyl-cyclopentenone instead of the 2-methyl-2-pentenal and the GC analysis was at 15 psi using the following temperature program: 120° C. for 10 min, 10° C./min up to 200° C., 200° C. for 2 min.

FIG. 13 shows a plot of the % conversion of 2-methyl-cyclopentenone and the stereomeric excess (% e.e.) of the resulting 2-methyl-cyclopentanone. Positive stereomeric excess values are predominantly S-2-methyl-cyclopentanone and negative stereomeric excess values are predominantly R-2-methyl-cyclopentanone.

By comparison to Example 11 (whose results are also shown in FIG. 13), this example further illustrates a pre-tuned plurality of polypeptides related to a parent polypeptide wherein members of the plurality react with different activities and different stereoselectivities on different naïve substrates, that is substrates not tested or used in constructing the pre-tuned plurality.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

We claim:

1. A method useful for identifying at least one polypeptide having a desired activity, comprising:
  (i) screening a plurality of polypeptide variants against a plurality of ligands of interest, wherein each variant reacts with at least one ligand to produce a detectable signal, and wherein at least two members of the plurality of polypeptide variants are related to a parent polypeptide and react with different ligands; and (ii) identifying at least one variant that produces a signal upon reaction with at least one ligand of interest, thereby identifying at least one polypeptide having a desired activity.

2. The method of claim 1, wherein the at least two members of the plurality of polypeptide variants are related to a parent polypeptide and react with differing levels of activity upon a given ligand.

3. The method of claim 1, further comprising: (iii) identifying at least one second variant that produces a signal upon reaction with the ligand of interest; (iv) postulating a sequence-activity relationship between the amino acid residues within the identified variants and the ability of each variant to produce a detectable signal; (v) generating a second plurality of polypeptide variants based on the sequence-activity relationship; (vi) screening the second plurality against the ligand of interest; and (vii) identifying at least one variant from the second plurality that produces an enhanced signal of interest as compared to the identified variants.

4. The method of claim 3, in which the identity of the ligand of interest is unknown.

5. The method of claim 3, in which each variant is an enzyme and the ligand of interest is a candidate substrate for the enzyme.

6. The method of claim 3, in which each variant is a receptor and the ligand of interest is a candidate ligand for the receptor.

7. The method of claim 3, in which two-or more members of the plurality of polypeptide variants differ in the signal produced.

8. The method of claim 7, in which the signal produced is selected from a signal indicating substrate specificity, chemoselectivity, regioselectivity, stereoselectivity, stereospecificity, ligand specificity, receptor agonism, receptor antagonism, conversion of a cofactor, or any combination thereof.

9. The method of claim 3, in which two or more-members of the plurality of polypeptide variants differ in the level of signal produced.

10. The method of claim 9, in which the difference in level is a difference in rate of product formation, percent conversion of a substrate to a product, or percent conversion of a cofactor.

11. The method of claim 1, in which the identity of the ligand of interest is unknown.

12. The method of claim 1, in which each variant is an enzyme and the ligand of interest is a candidate substrate for the enzyme.

13. The method of claim 1, in which each variant is a receptor and the ligand of interest is a candidate ligand for the receptor.

14. The method of claim 1, in which at least two or more members of the plurality of polypeptide variants differ in the signal produced.

15. The method of claim 14, in which the signal produced is selected from a signal indicating substrate specificity, chemoselectivity, regioselectivity, stereoselectivity, stereospecificity, ligand specificity, receptor agonism, receptor antagonism, conversion of a cofactor, or any combination thereof.

16. The method of claim 1, in which two or more members of the plurality of polypeptide variants differ in the level of signal produced.

17. The method of claim 16, in which the difference in level is a difference in rate of product formation, percent conversion of a substrate to a product, or percent conversion of a cofactor.

* * * * *